US005688936A

United States Patent [19]
Edwards

[11] Patent Number: 5,688,936
[45] Date of Patent: Nov. 18, 1997

[54] VESICLE MEMBRANE TRANSPORT PROTEINS

[75] Inventor: Robert H. Edwards, Los Angeles, Calif.

[73] Assignee: The Regents of the University of California, Oakland, Calif.

[21] Appl. No.: 63,552

[22] Filed: May 14, 1993

Related U.S. Application Data

[63] Continuation-in-part of Ser. No. 923,096, Jul. 30, 1992, abandoned, which is a continuation-in-part of Ser. No. 899,074, Jun. 11, 1992, abandoned.

[51] Int. Cl.⁶ .................... C07H 21/04; C07K 14/435
[52] U.S. Cl. .................... 536/23.5; 530/350; 530/827
[58] Field of Search ............................ 536/23.1, 23.5; 435/320.1, 240.2, 240.4, 252.3, 254.11, 254.2

[56] References Cited

U.S. PATENT DOCUMENTS

| | | | |
|---|---|---|---|
| 4,376,110 | 3/1983 | David et al. | 436/513 |
| 4,548,904 | 10/1985 | Kent et al. | 436/89 |
| 5,082,670 | 1/1992 | Gage et al. | 424/520 |

FOREIGN PATENT DOCUMENTS

WO9102788  3/1991  WIPO.

OTHER PUBLICATIONS

P.M. Burger et al., "GABA and Glycine in Synaptic Vesicles: Storage and Transport Characteristics," *Neuron* 7:287–293 (1991).

J.W. Hell et al., "Energy Dependence and Functional Reconstitution of the γ-Aminobutyric Acid Carrier from Synaptic Vesicles," *J. Biol. Chem.* 265:2111–2117 (1990).

P.R. Maycox et al., "Glutamate Uptake by Brain Synaptic Vesicles," *J. Biol. Chem.* 263:15423–15428 (1988).

B.W. Hicks et al., "Purification and Characterization of a Nonvesicular Vesamicol–Binding Protein from Electric Organ and Demonstration of a Related Protein in Mammalian Brain," *J. Neurochem.* 57:509–519 (1991).

P.E. Kish et al., "Active Transport of γ-Aminobutyric Acid and Glycine into Synaptic Vesicles," *Proc. Natl. Acad. Sci. USA* 86:3877–3881 (1989).

M.D. Carlson et al., "Characterization of the Solubilized and Reconstituted ATP–Dependent Vesicular Glutamate Uptake System," *J. Biol. Chem.* 264:7369–7376 (1989).

Y. Stern–Bach et al., "Identification and Purification of a Functional Amine Transporter from Bovine Chromaffin Granules," *J. Biol. Chem.* 265:3961–3966 (1990).

D.B. Calne & J.W. Langston, "Aetiology of Parkinson's Disease," *Lancet* 1457–1459 (Dec. 24/31, 1983).

J.W. Langston et al., "Chronic Parkinsonism in Humans Due to a Product of Meperidine–Analog Synthesis," *Science* 219:979–980 (1983).

R.S. Burns et al., "A Primate Model of Parkinsonism: Selective Destruction of Dopaminergic Neurons in the Pars Compacta of the Substantia Nigra by N–Methyl–4–Phenyl–1,2,3,6–Tetrahydropyridine," *Proc. Natl. Acad. Sci. USA* 80:4546–4550 (1983).

R.E. Heikkila et al., "Dopaminergic Neurotoxicity of 1–Methyl–4–Phenyl–1,2,5,6–Tetrahydropyridine in Mice," *Science* 224:1451–1453 (1984).

K. Chiba et al., "Metabolism of the Neurotoxic Tertiary Amine, MPTP, by Brain Monoamine Oxidase," *Biochem. Biophys. Res. Comm.* 120:574–578 (1984).

J.W. Langston et al., "Pargyline Prevents MPTP–Induced Parkinsonism in Primates," *Science* 225:1480–1482 (1984).

S.P. Markey et al., "Intraneuronal Generation of a Pyridinium Metabolite May Cause Drug–Induced Parkinsonism," *Nature* 311:464–467 (1984).

J.A. Javitch et al., "Parkinsonism–Inducing Neurotoxin, N–Methyl–4–Phenyl–1,2,3,6–Tetrahydropyridine: Uptake of the Metabolite N–Methyl–4–Phenylpyridine by Dopamine Neurons Explains Selective Toxicity," *Proc. Natl. Acad. Sci. USA* 82:2173–2177 (1985).

S.H. Snyder et al., "Selective Uptake of MPP⁺ by Dopamine Neurons is Required for MPTP Toxicity: Studies in Brain Synaptosomes and PC–12 Cells," *MPTP: A Neurotoxin Producing a Parkinsonian Syndrome* (S.P. Markey et al., eds., Academic Press, New York, 1986), pp. 191–201.

M.J. Krueger et al., "Evidence of the Blockade of Mitochondrial Respiration by the Neurotoxin 1–Methyl–4–Phenylpyridinium (MPP⁺) Involves Binding at the Same Site as the Respiratory Inhibitor, Rotenone," *Biochem. Biophys. Res. Comm.* 169:123–128 (1990).

R.R. Ramsay et al., "Interaction of 1–Methyl–4–Phenylpyridinium Ion (MPP⁺) and Its Analogs with the Rotenone/Piericidin Binding Site of NADH Dehydrogenase," *J. Neurochem.* 56:1184–1190 (1991).

Y. Mizuno et al., "Deficiencies in Complex I Subunits of the Respiratory Chain in Parkinson's Disease," *Biochem. Biophys. Res. Comm.* 163:1450–1455 (1989).

W.D. Parker, Jr. et al., "Abnormalities of the Electron Transport Chain in Idiopathic Parkinson's Disease," *Ann. Neurol.* 26:719–723 (1989).

(List continued on next page.)

*Primary Examiner*—Stephanie W. Zitomer
*Attorney, Agent, or Firm*—Merchant, Gould, Smith, Edell, Welter & Schmidt

[57] ABSTRACT

Complete cDNA and amino acid sequences are disclosed for rat adrenal-specific and brain-specific transport protein, as well as for human brain-specific transport protein. Methods for obtaining the genes encoding these proteins and for obtaining recombinantly produced protein are described. Antibodies and methods for isolating additional vesicle membrane transport proteins are also described. Methods for using the vesicle membrane transport proteins to identify compounds that selectively inhibit transport of toxic molecules into vesicles, and that prevent inhibition of transport of toxic molecules are also provided. The invention includes methods to treat and diagnose diseases associated with sequestration of toxic molecules in mammalian cells.

1 Claim, 52 Drawing Sheets

OTHER PUBLICATIONS

J.M. Shoffner et al., "Mitochondrial Oxidative Phosphorylation Defects in Parkinson's Disease," *Ann. Neurol.* 30:332–339 (1991).

The Parkinson's Study Group, "Effect of Deprenyl on the Progression of Disability in Early Parkinson's Disease," *New Engl. J. Med.* 321:1364–1371 (1989).

G. Cohen, "Monoamine Oxidase and Oxidative Stress at Dopaminergic Synapses," *J. Neural Transm. Suppl.* 32:229–238 (1990).

L. Turski et al., "Protection of Substantia Nigra from MPP+ Neurotoxicity by N–Methyl–D–Aspartate Antagonists," *Nature* 349:414–418 (1991).

C. Hyman et al., "BDNF is a Neurotrophic Factor for Dopaminergic Neurons of the Substantia Nigra," *Nature* 350:230–232 (1991).

J.F. Reinhard, Jr. et al., "Subcellular Compartmentalization of 1–Methyl–4–Phenylpyridinium with Catecholamines in Adrenal Medullary Chromaffin Vesicles may explain the lack of Toxicity to Adrenal Chromaffin Cells," *Natl. Acad. Sci. USA* 84:8160–8164 (1987).

L.A. Greene & G. Rein, "Release, Storage, and Uptake of Catecholamines by a Clonal Cell Line of Nerve Growth Factor (NGF) Responsive Pheochromocytoma Cells," *Brain Res.* 129:247–263 (1977).

T. Denton & B.D. Howard, "A Dopaminergic Cell Line Variant Resistant to the Neurotoxin 1–Methyl–4–Phenyl–1,2,3,6–Tetrahydropyridine," *J. Neurochem.* 49:622–630 (1987).

D.W. Choi & S.M. Rothman, "The Role of Glutamate Neurotoxicity in Hypoxic–Ischemic Neuronal Death," *Annu. Rev. Neurosci.* 13:171–182 (1990).

A. Carlsson, "Early Psychopharmacology and the Rise of Modern Brain Research," *J. Psychopharmacol.* 4:120–126 (1990).

R.J. Wyatt, "Schizophrenia, Just the Facts," *Schizophr. Res.* 1:3–18 (1988).

R.G. Johnson, Jr., "Accumulation of Biological Amines Into Chromaffin Granules: A Model for Hormone and Neurotransmitter Transport," *Physiol. Rev.* 68:232–307 (1988).

D.C. Anderson et al., "Proton Gradient Linkage to Active Uptake of [$^3$H] Acetylcholine by Torpedo Electric Organ Synaptic Vesicles," *Biochemistry* 21:3037–3043 (1982).

J.W. Hell et al., "Uptake of GABA by Rat Brain Synaptic Vesicles Isolated by a New Procedure," *EMBO J.* 7:3023–3029 (1988).

P.R. Maycox et al., "Bacteriorhodopsin Drives the Glutamate Transporter of Synaptic Vesicles After Co–reconstitution," *EMBO J.* 9:1465–1469 (1990).

J.W. Hell et al., "Functional Reconstitution of γ–Aminobutyric Acid Transporter from Synaptic Vesicles Using Artificial Ion Gradients," *Biochemistry* 30:11795–11800 (1991).

C. Chen & H. Okayama, "High–Efficiency Transformation of Mammalian Cells by Plasmid DNA," *Mol. Cell. Biol.* 7:2745–2752 (1987).

A. Aruffo & B. Seed, "Molecular Cloning of CD28 cDNA by a High–Efficiency COS Cell Expression System," *Proc. Natl. Acad. Sci. USA* 84:8573–8577 (1987).

A.T. Dobson et al., "A Latent Nonpathogenic HSV–1 Derived Vector Stably Expresses β–Galactosidase in Mouse Neurons," *Neuron* 5:353–360 (1990).

A.I. Geller & A. Freese, "Infection of Cultured Central Nervous System Neurons with a Defective Herpes Simplex Virus 1 Vector Results in Stable Expression of *Escherichia coli* β–Galactosidase," *Proc. Natl. Acad. Sci. USA* 87:1149–1153 (1990).

J.F. Reinhard, Jr. et al., "Mechanisms of Toxicity and Cellular Resistance to 1–Methyl–4–Phenyl–1,2,3,6–Tetrahydropyridine and 1–Methyl–4–Phenylpyridinium in Adrenomullary Chromaffin Cell Cultures," *J. Neurochem.* 55:311–320 (1990).

M. Kozak, "Compilation and Analysis of Sequences Upstream from the Translational Start Site in Eukaryotic mRNAs," *Nucl. Acids Res.* 12:857–872 (1984).

D. Eisenberg et al., "Analysis of Membrane and Surface Protein Sequences with the Hydrophobic Moment Plot," *J. Mol. Biol.* 179:125–142 (1984).

J. Guastella et al., "Cloning and Expression of a Rat Brain GABA Transporter," *Science* 249:1303–1306 (1990).

T. Pacholczyk et al., "Expression Cloning of a Cocaine–and Antidepressant–Sensitive Human Noradrenaline Transporter," *Nature* 350:350–354 (1991).

S. Shimada et al., "Cloning and Expression of a Cocaine––Sensitive Dopamine Transporter Complementary DNA," *Science* 254:576–578 (1991).

J.E. Kilty et al., "Cloning and Expression of a Cocaine–Sensitive Rat Dopamine Transporter," *Science* 254:578–579 (1991).

B.J. Hoffman et al., "Cloning of a Serotonin Transporter Affected by Anti–Depressants," *Science* 254:579–580 (1991).

W.G. Johnson et al., "Twin Studies and the Genetics of Parkinson's Disease—A Reappraisal," *Movement Disorders* 5:187–194 (1990).

R.R. Ramsay & T.P. Singer, "Energy–dependent Uptake of N–methyl–4–Phenylpyridinium, the Neurotoxic Metabolite of 1–Methyl–4–Phenyl–1,2,3,6–Tetrahydropyridine, by Mitochondria," *J. Biol. Chem.* 261:7585–7587 (1986).

M. Gribskov et al., "Profile Analysis: Detection of Distantly Related Proteins," *Proc. Nat. Acad. Sci. USA* 84:4355–4358 (1987).

J. Devereux et al., "A Comprehensive Set of Sequence Analysis Programs for the VAX," *Nucl. Acids Res.* 12:387–395 (1984).

R.G. Fowler et al., "Mutational Specificity of a Conditional *Escherichia coli* Mutator, mutD5," *Molec. Gen. Genet.* 133:179–184 (1974).

T.J. Silhavy et al., "Experiments with Gene Fusions" (Cold Spring Harbor Laboratory, Cold Spring Harbor, New York, 1984), pp. 75–78.

U. Gubler & B.J. Hoffman, "A Simple and Very Efficient Method for Generating cDNA Libraries," *Gene* 25:263–269 (1983).

W.J. Dower et al., "High Efficiency Transformation of *E. coli* by High Voltage Electroporation," *Nucl. Acids Res.* 16:6127–6145 (1988).

M.B. Hansen et al., "Re–examination and Further Development of a Precise and Rapid Dye Method for Measuring Cell Growth/Cell Kill," *J. Immunol. Meth.* 119:203–210 (1989).

J.D. de al Torre, "An Improved Approach to Histofluorescence Using the SPG Method for Tissue Monoamines," *J. Neurosci. Meth.* 3: 1–5 (1980).

K.M. Knigge et al., "Identification of Catecholamine and Luteinizing Hormone–Releasing Hormone (LHRH)–Containing Neurons in Primary Cultures of Dispersed Cells of the Basal Hypothalamus," *Brain Res.* 120:393–405 (1977).

D. Marchuk et al., "Construction of T–Vectors, a Rapid and General System for Direct Cloning of Unmodified PCR Products," *Nucl. Acids Res.* 19:1154 (1991).

C. Sternini et al., "Expression of Substance P/Neurokinin A–Encoding Preprotachykinin Messenger Ribonucleic Acids in the Rat Enteric Nervous System," *Gasteroenterology* 97:348–356 (1989).

T.G. Boulton et al., "ERKs: A Family of Protein–Serine/Threonine Kinases That Are Activated and Tyrosine Phosphorylated in Response to Insulin and NGF," *Cell* 65:663–675 (1991).

K.K. Kidd, "Trials and Tribulations in the Search for Genes Causing Neuropsychiatric Disorders," *Social Biol.* 38:163–178 (1991).

G.F. Koob & F.E. Bloom, "Cellular and Molecular Mechanisms of Drug Dependence," *Science* 242:715–723 (1988).

J. Axelrod et al. "Effect of Psychotropic Drugs on the Uptake of $H^3$–Norepinephrine by Tissues," *Science* 133:383–384 (1961).

T.B. Usdin et al., "Cloning of the Cocaine–Sensitive Bovine Dopamine Transporter," *Proc. Natl. Acad. Sci. USA* 88:11168–11171 (1991).

R.D. Blakely et al., "Cloning and Expression of a Functional Serotonin Transporter from Rat Brain," *Nature* 354:66–70 (1991).

G.R. Uhl, "Neurotransmitter Transporters (Plus): A Promising New Gene Family," *Trends Neurosci.* 15:265–268 (1992).

G. Pines et al., "Cloning and Expression of a Rat Brain L–Glutamate Transporter," *Nature* 360:464–467 (1992).

R.B. Kelly, "Secretary Granule and Synaptic Vesicle Formation," *Curr. Opin. Cell Biol.* 3:654–660 (1991).

W.S. Trimble et al., "Cellular and Molecular Biology of the Presynaptic Nerve Terminal," *Annu. Rev. Neurosci.* 14:93–12 (1991).

E.D. Freis, "Mental Depression in Hypertensive Patients Treated for Long Periods with Large Doses of Reserpine," *New Engl. J. Med.* 251:1006–1008 (1954).

F. McCormick et al., "Inducible Expression of Amplified Human Beta Interferon Genes in CHO Cells," *Mol. cell. Biol.* 4:166–172 (1984).

B.A. Hirayama et al., "Intestinal and Renal $Na^+$/Glucose Cotransporters Share Common Structures," *Am. J. Physiol.* 261:C296–C304 (1991).

K.H. Cox et al., "Detection of mRNAs in Sea Urchin Embryos by in Situ Hybridization Using Asymmetric RNA Probes," *Dev. Biol.* 101:485–502 (1984).

T. Mohandas et al., "Assignment of Human 3–Hydroxy–3–Methylglutaryl Coenzyme A Reductase Gene to q13→q23 Region of Chromosome 5," *Somatic Cell & Mol. Genet.* 12: 89–94 (1986).

M.E. Harper & G.F. Saunders, "Localization of Single Copy DNA Sequences on G–Banded Human Chromosomes by in Situ Hybridization," *Chromosoma* 83:4331–439 (1981).

L.A. Cannizzaro & B.S. Emanuel, "An Improved Method for G–Banding Chromosomes After in Situ Hybridization," *Cytogenet. & Cell. Genet.* 38:308–309 (1984).

R.S. Sparkes et al., "Human Genes Involved in Lipolysis of Plasma Lipoproteins: Mapping of Loci for Lipoprotein Lipase to 8p22 and Hepatic Lipase to 15q21," *Genomics* 1:138–144 (1987).

J. Hurst et al., "The Human Neurofilament Gene (NEFL) is Located on the Short Arm of Chromosome 8," *Cytogenet. Cell Genet.* 45: 30–32 (1987).

M.J. Somerville et al., "Localization of the 68,000–Da Human Neurofilament Gene (NF68) Using a Murine cDNA Probe," *Genome* 30:499–500 (1988).

S.E. Lux et al., "Hereditary Spherocytosis Associated with Deletion of Human Erythrocyte Ankryrin Gene on Chromosome 8," *Nature* 345:736–739 (1990).

D.A. Schwinn et al., "Molecular Cloning and Expression of the cDNA for a Novel $\alpha_1$–Adrenergic Receptor Subtype," *J. Biol. Chem.* 265:8183–8189 (1990).

K.H. Astrin et al., "Regional Assignment of the Human Uroporphyrinogen III Synthase (UROS) Gene to Chromosome 10q25.2→q26.3," *Hum. Genet.* 87:18–22 (1992).

J.A. Affholter et al., "Insulin–Degrading Enzyme: Stable Expression of the Human Complementary DNA, Characterization of Its Protein Product, and Chromosomal Mapping of the Human and Mouse Genes," *Mol. Endocrinol.* 4:1125–1135 (1990).

Y.–S. Fan et al., "Mapping cDNA Sequences by Fluorescence in Situ Hybridization Directly on Banded Metaphase Chromosomes," *Proc. Natl. Acad. Sci. USA* 87:6223–6227 (1990).

M. Lemieux et al., "A Simple Method for Simultaneous R–or G–Banding and Fluorescence in Situ Hybridization of Small Single–Copy Genes," *Cytogenet. Cell Genet.* 59:311–312 (1992).

C.K. Surratt et al., "A Human Synaptic Vesicle Monoamine Transporter cDNA Predicts Posttranslational Modifications, Reveals Chromosome 10 Gene Localization and Identifies TagI RFPLs," *FEBS Lett.* 318:325–330 (1993).

T.L. Yang–Feng et al., "Human Luteinizing Hormone–Releasing Hormone Gene (LHRH) Is Located on Short Arm of Chromosome 8 (Region 8p11.2→p21)," *Som. Cell. Mol. Genet.* 12:95–100 (1986).

T.L. Yang–Feng et al., "Chromosomal Organization of Adrenergic Receptor Genes," *Proc. Natl. Acad. Sci. USA* 87:1516–1520 (1990).

Liu et al., Cell 70:539–551 (Aug. 8, 1992).

FIG. IA

```
1    CCTCGAGATCCATTGTGCTCTAAAGTCAGCACATCCACTTTCAGAGAACAGAGTCTCTGC

61   TGTCTTGCCAACGGCTGCTCCTTCCTCTCTGAGTGCCTCACATCAAGATAAGCTAGAAGT

121  GAGCTTCACTGGACCAGGCAGACTTCTTCTCCTATAAAGGTGACAGAAGACCACATTTGT

181  CGAGGGGTCTTCCTAAGCCCTGGGAGGAGAAGCCCCCACCATCTCACTCCCTACCCAGCC

241  CAGCCTCCTGCAGCCCTTGCCATGCTCCAGGTTGTTCTGGGTGCTCCTCAGCGGTTGCTG
                       MetLeuGlnValValLeuGlyAlaProGlnArgLeuLeu

301  AAGGAAGGAAGGCAGTCCCGCAAGCTGGTGCTGGTGGTGGTGTTCGTGGCTCTGCTTCTG
14   LysGluGlyArgGlnSerArgLysLeuValLeuValValValPheValAlaLeuLeuLeu

361  GACAACATGCTGCTCACTGTGGTGGTGCCCATTGTGCCCACCTTCCTGTACGCGACAGAG
34   AspAsnMetLeuLeuThrValValValProIleValProThrPheLeuTyrAlaThrGlu

421  TTCAAAGACAGCAACTCTTCTCTGCATAGGGGTCCTTCTGTAAGCTCCCAGCAAGCTCTC
54   PheLysAspSerAsnSerSerLeuHisArgGlyProSerValSerSerGlnGlnAlaLeu
                       *

481  ACCTCTCCTGCCTTCTCTACCATATTCTCCTTCTTTGACAACACCACCACGACTGTAGAA
74   ThrSerProAlaPheSerThrIlePheSerPhePheAspAsnThrThrThrThrValGlu
                                                          *

541  GAACATGTACCCTTCCGTGTAACTTGGACAAATGGCACCATCCCTCCTCCAGTCACTGAA
94   GluHisValProPheArgValThrTrpThrAsnGlyThrIleProProProValThrGlu
                                         *

601  GCCAGCTCAGTACCAAAAAACAACTGCTTGCAAGGGATAGAGTTCTTAGAAGAAGAAAAC
114  AlaSerSerValProLysAsnAsnCysLeuGlnGlyIleGluPheLeuGluGluGluAsn

661  GTTCGGATTGGGATTCTATTTGCTTCAAAAGCTTTGATGCAACTTCTGGTCAACCCATTT
134  ValArgIleGlyIleLeuPheAlaSerLysAlaLeuMetGlnLeuLeuValAsnProPhe

721  GTAGGACCTCTTACTAACAGGATTGGCTATCACATCCCCATGTTTGTTGGCTTTATGATC
154  ValGlyProLeuThrAsnArgIleGlyTyrHisIleProMetPheValGlyPheMetIle

781  ATGTTTCTCTCCACACTAATGTTTGCTTTCTCTGGCACCTATGCCCTGCTATTTGTGGCC
174  MetPheLeuSerThrLeuMetPheAlaPheSerGlyThrTyrAlaLeuLeuPheValAla

841  CGAACTCTCCAAGGCATTGGATCTTCGTTTTCATCTGTTGCAGGACTTGGGATGCTGGCC
194  ArgThrLeuGlnGlyIleGlySerSerPheSerSerValAlaGlyLeuGlyMetLeuAla
```

FIG. IB

```
 901 AGTGTCTATACTGACAACTATGAGAGAGGGAGAGCCATGGGAATTGCTTTGGGGGGCCTG
 214 SerValTyrThrAspAsnTyrGluArgGlyArgAlaMetGlyIleAlaLeuGlyGlyLeu

961 GCCTTGGGACTTCTGGTGGGAGCACCTTTCGGAAGTGTGATGTATGAATTTGTGGGCAAG
 234 AlaLeuGlyLeuLeuValGlyAlaProPheGlySerValMetTyrGluPheValGlyLys

1021 TCCTCACCATTCCTCATCTTGGCCTTCTTGGCACTTCTGGATGGAGCTCTCCAACTTTGC
 254 SerSerProPheLeuIleLeuAlaPheLeuAlaLeuLeuAspGlyAlaLeuGlnLeuCys

1081 ATCCTATGGCCTTCGAAAGTGTCTCCTGAGAGTGCCATGGGGACTTCGCTTTTGACGCTT
 274 IleLeuTrpProSerLysValSerProGluSerAlaMetGlyThrSerLeuLeuThrLeu

1141 CTCAAAGACCCTTACATCCTGGTAGCAGCAGGTTCCATCTGCTTGGCCAACATGGGAGTC
 294 LeuLysAspProTyrIleLeuValAlaAlaGlySerIleCysLeuAlaAsnMetGlyVal

1201 GCCATACTAGAGCCCACGCTGCCCATCTGGATGATGCAGACCATGTGCTCCCCCGAGTGG
 314 AlaIleLeuGluProThrLeuProIleTrpMetMetGlnThrMetCysSerProGluTrp

1261 CAGCTAGGTCTGGCTTTCTTGCCTGCTAGTGTGGCCTACCTCATTGGCACGAACCTCTTT
 334 GlnLeuGlyLeuAlaPheLeuProAlaSerValAlaTyrLeuIleGlyThrAsnLeuPhe

1321 GGTGTGTTGGCTAACAAGATGGGTCGGTGGCTGTGCTCCCTTGTTGGGATGGTGGCAGTA
 354 GlyValLeuAlaAsnLysMetGlyArgTrpLeuCysSerLeuValGlyMetValAlaVal

1381 GGTATCAGCTTGCTCTGTGTACCTCTGGCTCACAATATTTTTGGTCTTATTGGCCCCAAT
 374 GlyIleSerLeuLeuCysValProLeuAlaHisAsnIlePheGlyLeuIleGlyProAsn

1441 GCAGGCCTTGGCTTTGCCATAGGAATGGTGGATTCCTCTCTGATGCCCATCATGGGATAC
 394 AlaGlyLeuGlyPheAlaIleGlyMetValAspSerSerLeuMetProIleMetGlyTyr

1501 CTGGTGGACTTACGCCACACCTCTGTGTATGGGAGTGTCTATGCCATCGCCGATGTGGCC
 414 LeuValAspLeuArgHisThrSerValTyrGlySerValTyrAlaIleAlaAspValAla

1561 TTTTGTGTGGGCTTTGCTATTGGCCCATCTACTGGGGGTGTTATCGTACAGGTCATTGGC
 434 PheCysValGlyPheAlaIleGlyProSerThrGlyGlyValIleValGlnValIleGly

1621 TTTCCTTGGCTCATGGTCATCATTGGTACCATCAACATCATTTATGCTCCTCTCTGCTGC
 454 PheProTrpLeuMetValIleIleGlyThrIleAsnIleIleTyrAlaProLeuCysCys
```

FIG. IC

```
1681 TTCCTGCAGAACCCGCCAGCTAAGGAGGAGAAGCGTGCAATTCTGAGCCAGGAATGCCCC
 474 PheLeuGlnAsnProProAlaLysGluGluLysArgAlaIleLeuSerGlnGluCysPro

1741 ACAGAGACCCAGATGTACACATTCCAGAAGCCCACAAAGGCGTTTCCACTAGGAGAGAAC
 494 ThrGluThrGlnMetTyrThrPheGlnLysProThrLysAlaPheProLeuGlyGluAsn

1801 AGCGATGATCCTAGCAGCGGGGAGTAACTGCGGAGGGCGATATCTGAGCCTCACATCTAC
 514 SerAspAspProSerSerGlyGlu   [ SEQ ID NO : 2 ]

1861 AGGGACCAGTCTACTACAGATTCAATAATTTTCACTTTCCTCTCCTCCAGGCCACTGCCT

1921 TCCTCCCTTCTTATTGATACCTTTCCTTTACTCACCTGTAAGTGCAACCCACCACTCTCC

1981 CTCTGTGCTTTGACACCACCCATGGCCCACTTTTTGTGGGAGGACAGTGCTATTTCCTGC

2041 CAGGCCAAAGCGAAGCTGATTAAAGCTGAGTTGTGACAAGTTCTGCAAGGGGTGACTCAC

2101 TTCCTGCAGGCAGGACTGAACAATGTGCCTGCGAAATCAGGGGGACAAATGACAAGCCTG

2161 CCTTTCTTCTCTGATTGTTTTTTTTTTTTTTTGACATATTACCAATATGTCCTAAAATT

2221 TGACTTGTGTCCTGTGAAATGCTTTCCCCTTATTTTTTCCAGTTTAGCTTCTATACATAC

2281 GGGTTTTTGCTTATTTTATGTGCTAAAATTGTTTACCTTCATTAAGTGAGGCCTTCCTAC

2341 TTTCTTCATCGCCCAATTGAGAGGAAATAAACAACTTTCTTAGGCTTGAAAAAAAACTTT

2401 AGAGCACAATGGATCTCGAGG   [ SEQ ID NO : 1 ]
```

FIG. 2A

```
1      GGGCGCACGGACAGAGACCCAGGCTGTGTGGCGCTATAACCGCGCAGTCACAGGCGAGC

60     CAGAGCAGAGCCATGGCCCTGAGCGATCTGGTGCTGCTGCGATGGCTGCGGGACAGCCGC
       [ SEQ ID NO : 4 ]  MetAlaLeuSerAspLeuValLeuLeuArgTrpLeuArgAspSerArg

119    CACTCGCGCAAACTGATCCTGTTCATCGTGTTCCTTGCGCTGCTGCTGGACAACATGCTG
17     HisSerArgLysLeuIleLeuPheIleValPheLeuAlaLeuLeuLeuAspAsnMetLeu

179    CTCACCGTCGTGGTTCCCATCATCCCCAGCTATCTGTACAGCATTAAGCATGAGAAAAAC
37     LeuThrValValValProIleIleProSerTyrLeuTyrSerIleLysHisGluLysAsn
                                                                *
239    TCTACGGAAATCCAGACCACCAGACCAGAGCTCGTGGTCTCCACCTCCGAAAGCATCTTC
57     SerThrGluIleGlnThrThrArgProGluLeuValValSerThrSerGluSerIlePhe

299    TCTTACTATAACAACTCTACTGTGTTGATCACCGGGAATGCCACTGGGACTCTTCCAGGA
77     SerTyrTyrAsnAsnSerThrValLeuIleThrGlyAsnAlaThrGlyThrLeuProGly
                  *                              *
359    GGGCAGTCACACAAGGCTACCAGCACACAGCACACTGTGGCTAACACCACTGTCCCTTCG
97     GlyGlnSerHisLysAlaThrSerThrGlnHisThrValAlaAsnThrThrValProSer
                                                                *
419    GACTGTCCCAGTGAAGACAGAGACCTTCTGAATGAGAATGTGCAAGTTGGGCTGCTGTTT
117    AspCysProSerGluAspArgAspLeuLeuAsnGluAsnValGlnValGlyLeuLeuPhe

479    GCCTCCAAAGCCACTGTCCAGCTCCTCACTAACCCATTCATAGGACTTCTGACCAACAGA
137    AlaSerLysAlaThrValGlnLeuLeuThrAsnProPheIleGlyLeuLeuThrAsnArg

539    ATTGGCTATCCAATTCCCATGTTTGCCGGCTTCTGCATCATGTTTATCTCAACAGTTATG
157    IleGlyTyrProIleProMetPheAlaGlyPheCysIleMetPheIleSerThrValMet

599    TTTGCCTTCTCCAGCAGCTATGCCTTCCTGCTGATCGCCAGGTCCCTTCAGGGAATTGGC
177    PheAlaPheSerSerSerTyrAlaPheLeuLeuIleAlaArgSerLeuGlnGlyIleGly

659    TCCTCCTGCTCATCCGTGGCTGGGATGGGTATGCTGGCCAGCGTGTACACAGATGATGAG
197    SerSerCysSerSerValAlaGlyMetGlyMetLeuAlaSerValTyrThrAspAspGlu

719    GAGAGGGGGAAGCCCATGGGCATTGCTTTGGGTGGCCTGGCCATGGGAGTCTTAGTGGGA
217    GluArgGlyLysProMetGlyIleAlaLeuGlyGlyLeuAlaMetGlyValLeuValGly

779    CCCCCCTTCGGGAGTGTGCTCTATGAGTTTGTGGGGAAGACAGCTCCCTTCCTGGTGCTA
237    ProProPheGlySerValLeuTyrGluPheValGlyLysThrAlaProPheLeuValLeu
```

FIG. 2B

```
 839  GCTGCCTTGGTGCTCTTGGATGGGGCTATTCAGCTCTTTGTGCTCCAGCCGTCCCGAGTA
 257  AlaAlaLeuValLeuLeuAspGlyAlaIleGlnLeuPheValLeuGlnProSerArgVal

899  CAGCCAGAGAGTCAGAAGGGGACACCTCTAACGACCTTGCTGAAGGATCCATACATCCTC
 277  GlnProGluSerGlnLysGlyThrProLeuThrThrLeuLeuLysAspProTyrIleLeu

959  ATCGCTGCAGGCTCCATCTGCTTTGCAAACATGGGGATAGCCATGCTGGAGCCCGCCCTG
 297  IleAlaAlaGlySerIleCysPheAlaAsnMetGlyIleAlaMetLeuGlyProAlaLeu

1019  CCCATCTGGATGATGGAGACCATGTGTTCCCGAAAGTGGCAGCTGGGCGTTGCTTTCCTC
 317  ProIleTrpMetMetGluThrMetCysSerArgLysTrpGlnLeuGlyValAlaPheLeu

1079  CCGGCGAGCATCTCTTATCTCATTGGAACCAATATTTTTGGGATACTTGCACACAAAATG
 337  ProAlaSerIleSerTyrLeuIleGlyThrAsnIlePheGlyIleLeuAlaHisLysMet

1139  GGAAGGTGGCTATGTGCTCTTCTGGGAATGGTAATTGTTGGAATCAGCATTTTATGCATC
 357  GlyArgTrpLeuCysAlaLeuLeuGlyMetValIleValGlyIleSerIleLeuCysIle

1199  CCCTTTGCAAAAAATATCTATGGACTCATCGCTCCCAACTTTGGAGTTGGTTTTGCAATT
 377  ProPheAlaLysAsnIleTyrGlyLeuIleAlaProAsnPheGlyValGlyPheAlaIle

1259  GGGATGGTGGACTCCTCTATGATGCCTATCATGGGCTACCTGGTTGACCTGCGGCATGTG
 397  GlyMetValAspSerSerMetMetProIleMetGlyTyrLeuValAspLeuArgHisVal

1319  TCTGTCTATGGGAGTGTTTATGCCATTGCAGACGTGGCCTTTTGTATGGGCTATGCTATC
 417  SerValTyrGlySerValTyrAlaIleAlaAspValAlaPheCysMetGlyTyrAlaIle

1379  GGTCCCTCTGCTGGTGGTGCCATCGCAAAGGCAATTGGCTTTCCTTGGCTTATGACAATT
 437  GlyProSerAlaGlyGlyAlaIleAlaLysAlaIleGlyPheProTrpLeuMetThrIle

1439  ATTGGGATAATTGATATCGCTTTTGCTCCACTCTGCTTTTTCCTTCGAAGTCCACCTGCT
 457  IleGlyIleIleAspIleAlaPheAlaProLeuCysPhePheLeuArgSerProProAla

1499  AAGGAGGAAAAAATGGCTATCCTCATGGACCACAACTGTCCCATTAAAAGAAAGATGTAC
 477  LysGluGluLysMetAlaIleLeuMetAspHisAsnCysProIleLysThrLysMetTyr

1559  ACTCAGAATAATGTCCAGTCATATCCCATCGGTGATGATGAAGAATCTGAAAGTGACTGA
 497  ThrGlnAsnAnsValGlnSerTyrProIleGlyAspAspGluGluSerGluSerAsp***

1619  GACCCTCTAACGTCGCCC  [ SEQ ID NO : 3 ]
```

FIG. 3A

```
1    GGCGCAAGCGACCCCGAGCGGAGCCCCGGAGCCATGGCCCTGAGCGAGCTGGCGCTGGTC
                                       MetAlaLeuSerGluLeuAlaLeuVal

61   CGCTGGCTGCAGGAGAGCCGCCGCTCGCGGAAGCTCATCCTGTTCATCGTGTTCCTGGCG
10   ArgTrpLeuGlnGluSerArgArgSerArgLysLeuIleLeuPheIleValPheLeuAla

121  CTGCTGCTGGACAACATGCTGCTCACTGTCGTGGTCCCCATCATCCCAAGTTATCTGTAC
30   LeuLeuLeuAspAsnMetLeuLeuThrValValValProIleIleProSerTyrLeuTyr

181  AGCATTAAGCATGAGAAGAATGCTACAGAAATCCAGACGGCCAGGCCAGTGCACACTGCC
50   SerIleLysHisGluLysAsnAlaThrGluIleGlnThrAlaArgProValHisThrAla
                                *

241  TCCATCTCAGACAGCTTCCAGAGCATCTTCTCCTATTATGATAACTCGACTATGGTCACC
70   SerIleSerAspSerPheGlnSerIlePheSerTyrTyrAspAsnSerThrMetValThr
                                                              *

301  GGGAATGCTACCAGAGACCTGACACTTCATCAGACCGCCACACAGCACATGGTGACCAAC
90   GlyAsnAlaThrArgAspLeuThrLeuHisGlnThrAlaThrGlnHisMetValThrAsn
          *                                                    *

361  GCGTCCGCTGTTCCTTCCGACTGTCCCAGTGAAGACAAAGACCTCCTGAATGAAAACGTG
110  AlaSerAlaValProSerAspCysProSerGluAspLysAspLeuLeuAsnGluAsnVal

421  CAAGTTGGTCTGTTGTTTGCCTCGAAAGCCACCGTCCAGCTCATCACCAACCCTTTCATA
130  GlnValGlyLeuLeuPheAlaSerLysAlaThrValGlnLeuIleThrAsnProPheIle

481  GGACTACTGACCAACAGAATTGGCTATCCAATTCCCATATTTGCGGGATTCTGCATCATG
150  GlyLeuLeuThrAsnArgIleGlyTyrProIleProIlePheAlaGlyPheCysIleMet

541  TTTGTCTCAACAATTATGTTTGCCTTCTCCAGCAGCTATGCCTTCCTGCTGATTGCCAGG
170  PheValSerThrIleMetPheAlaPheSerSerSerTyrAlaPheLeuLeuIleAlaArg

601  TCGCTGCAGGGCATCGGCTCGTCCTGCTCCTCTGTGGCTGGGATGGGCATGCTTGCCAGT
190  SerLeuGlnGlyIleGlySerSerCysSerSerValAlaGlyMetGlyMetLeuAlaSer

661  GTCTACACAGATGATGAAGAGAGAGGCAACGTCATGGGAATCGCCTTGGGAGGCCTGGCC
210  ValTyrThrAspAspGluGluArgGlyAsnValMetGlyIleAlaLeuGlyGlyLeuAla

721  ATGGGGGTCTTAGTGGGCCCCCCCTTCGGGAGTGTGCTCTATGAGTTTGTGGGGAAGACG
230  MetGlyValLeuValGlyProProPheGlySerValLeuTyrGluPheValGlyLysThr
```

FIG. 3B

```
781   GCTCCGTTCCTGGTGCTGGCCGCCCTGGTACTCTTGGATGGAGCTATTCAGCTCTTTGTG
250   AlaProPheLeuValLeuAlaAlaLeuValLeuLeuAspGlyAlaIleGlnLeuPheVal

841   CTCCAGCCGTCCCGGGTGCAGCCAGAGAGTCAGAAGGGGACACCCCTAACCACGCTGCTG
270   LeuGlnProSerArgValGlnProGluSerGlnLysGlyThrProLeuThrThrLeuLeu

901   AAGGACCCGTACATCCTCATTGCTGCAGGCTCCATCTCCTTTGCAAACATGGGCATCGCC
290   LysAspProTyrIleLeuIleAlaAlaGlySerIleCysPheAlaAsnMetGlyIleAla

961   ATGCTGGAGCCAGCCCTGCCCATCTGGATGATGGAGACCATGTGTTCCCGCAAGTGGCAG
310   MetLeuGluProAlaLeuProIleTrpMetMetGluThrMetCysSerArgLysTrpGln

1021  CTGGGCGTTGCCTTCTTGCCAGCTAGTATCTCTTATCTCATTGGAACCAATATTTTTGGG
330   LeuGlyValAlaPheLeuProAlaSerIleSerTyrLeuIleGlyThrAsnIlePheGly

1081  ATACTTGCACACACAATGGGGAGGTGGCTTTGTGCTCTTCTGGGAATGATAATTGTTGGA
350   IleLeuAlaHisLysMetGlyArgTrpLeuCysAlaLeuLeuGlyMetIleIleValGly

1141  GTCAGCATTTTATGTATTCCATTTCCAAAAAACATTTATGGACTCATAGCTCCGAACTTT
370   ValSerIleLeuCysIleProPheAlaLysAsnIleTyrGlyLeuIleAlaProAsnPhe

1201  GGAGTTGGTTTTGCAAATGGAATGGTGGATTCGTCAATGATGCCTATCATGGGCTACCTC
390   GlyValGlyPheAlaIleGlyMetValAspSerSerMetMetProIleMetGlyTyrLeu

1261  GTAGACCTGCGGCACGTGTCCGTCTATGGGAGTGTGTACGCCATTGCGGATGTGGCATTT
410   ValAspLeuArgHisValSerValTyrGlySerValTyrAlaIleAlaAspValAlaPhe

1321  TGTATGGGGTATGCTATAGGTCCTTCTGCTGGTGGTGCTATTGCAAAGGCAATTGGATTT
430   CysMetGlyTyrAlaIleGlyProSerAlaGlyGlyAlaIleAlaLysAlaIleGlyPhe

1381  CCATGGCTCATGACAATTATTGGGATAATTGATATTCTTTTTGCCCCTCTCTGCTTTTTT
450   ProTrpLeuMetThrIleIleGlyIleIleAspIleLeuPheAlaProLeuCysPhePhe

1441  CTTCGAAGTCCACCTGCCAAAGAAGAAAAAATGGCTATTCTCATGGATCACAACTGCCCT
470   LeuArgSerProProAlaLysGluGluLysMetAlaIleLeuMetAspHisAsnCysPro

1501  ATTAAAACAAAAATGTACACTCAGAATAATATCCAGTCATATCCGATAGGTGAAGATGAA
490   IleLysThrLysMetTyrThrGlnAsnAsnIleGlnSerTyrProIleGlyGluAspGlu
```

FIG. 3C

```
1561 GAATCTGAAAGTGACTGAGATGAGATCCTCAAAAATCATCAAAGTGTTTAATTGTATAAA
510  GluSerGluSerAsp***

1621 ACAGTGTTTCCAGTGACACAACTCATCCAGAACTGTCTTAGTCATACCATCCATCCCTGG

1681 TGAAAGAGTAAAACCAAAGGTTATTATTTCCTTTCCATGGTTATGGTCGATTGCCAACAG

1141 GTCAGCATTTTATGTATTCCATTTCCAAAAAACATTTATGGACTCATAGCTCCGAACTTT
370  ValSerIleLeuCysIleProPheAlaLysAsnIleTyrGlyLeuIleAlaProAsnPhe

1201 GGAGTTGGTTTTGCAAATGGAATGGTGGATTCGTCAATGATGCCTATCATGGGCTACCTC
390  GlyValGlyPheAlaIleGlyMetValAspSerSerMetMetProIleMetGlyTyrLeu

1261 GTAGACCTGCGGCACGTGTCCGTCTATGGGAGTGTGTACGCCATTGCGGATGTGGCATTT
410  ValAspLeuArgHisValSerValTyrGlySerValTyrAlaIleAlaAspValAlaPhe

1321 TGTATGGGGTATGCTATAGGTCCTTCTGCTGGTGGTGCTATTGCAAAGGCAATTGGATTT
430  CysMetGlyTyrAlaIleGlyProSerAlaGlyGlyAlaIleAlaLysAlaIleGlyPhe

1381 CCATGGCTCATGACAATTATTGGGATAATTGATATTCTTTTTGCCCCTCTCTGCTTTTTT
450  ProTrpLeuMetThrIleIleGlyIleIleAspIleLeuPheAlaProLeuCysPhePhe

1441 CTTCGAAGTCCACCTGCCAAAGAAGAAAAAATGGCTATTCTCATGGATCACAACTGCCCT
470  LeuArgSerProProAlaLysGluGluLysMetAlaIleLeuMetAspHisAsnCysPro

1501 ATTAAAACAAAAATGTACACTCAGAATAATATCCAGTCATATCCGATAGGTGAAGATGAA
490  IleLysThrLysMetTyrThrGlnAsnAsnIleGlnSerTyrProIleGlyGluAspGlu

1561 GAATCTGAAAGTGACTGAGATGAGATCCTCAAAAATCATCAAAGTGTTTAATTGTATAAA
510  GluSerGluSerAsp***  [ SEQ ID NO : 13 ]

1621 ACAGTGTTTCCAGTGACACAACTCATCCAGAACTGTCTTAGTCATACCATCCATCCCTGG

1681 TGAAAGAGTAAAACCAAAGGTTATTATTTCCTTTCCATGGTTATGGTCGATTGCCAACAG

1741 CCTTATAAAGAAAAGAAGCTTTTCTAGGGGTTTGTATAAATAGTGTTGAAACTTTATTT

1801 TATGTATTTAATTTTATTAAATATCATACAATATATTTTGATGAAATAGGTATTGTGTAA

1861 ATCTATAAATATTTGAATCCAAACCAAATATAATTTCC  [ SEQ ID NO : 12 ]
```

[ SEQ ID NO : 2 AND 4 ]

lumen

FIG. 5

```
1.3kb R1 h    CTGACTAAAGTAGTCTGCCCTACCTGTTGGTCAGTAGTCCTATGAAAGGGTTGGTGATGA
              GACTGATTTCATCAGACGGGATGGACAACCAGTCATCAGGATACTTTCCCAACCACTACT
              | | | | | | | | | | | | | | | | | | | | | | | | | | | | | |
17-3-5        | | | | | | | | | | | | | |520| | | | | |
[ 718 ]       | |<++T+G+ATA+++AATT++++++++++A++++++++++++T+++++A+++G++

120
                                                                     *
1.3kb R1 h    GCTGGACGGTGGCTTTCGAGGCAAACAACAGACCAACTTGCAGCTTTTCATTCAGGAGGT
              CGACCTGCCACCGAAAGCTCCGTTTGTTGTCTGGTTGAACGTCGAAAAGTAAGTCCTCCA
              | | | | | | | | | | | | | | | | | | | | | | | | | | | | | |
17-3-5        | | | | | |  480 | | | | | | | | | | | | | | | | |
[ 718 ]       <+++++++A++++++++G+++++++++++G+++C++++++++++CA++C+++++++A+++

180
                                                                     *
1.3kb R1 h    CTTTGTCTTCACTGGGACAGTCGGAAGGAAGACGGCAGGCCTTGGTCACCATGTGCTGTG
              GAAACAGAAGTGACCCTGTCAGCCTTCCTTCTGCCGTCCGGAACCAGTGGTACACGACAC
              | | | | | | | | | | | | | | | | | | | | | | | | | | | | | |
17-3-5        440| | | | | | | | | | | | | |400 | | | |
[ 718 ]       <++C+++++++++++++++++C+++++--+++A+-T++TG++A+C+++AG++++++++

240
                                                                     *
1.3kb R1 h    TGGCGGTCTGATGAAGTGTCAGGTCTCTGGTAGCATTCCCGGTGACCATAGTCGAGTTAT
              ACCGCCAGACTACTTCACAGTCCAGAGACCATCGTAAGGGCCACTGGTATCAGCTCAATA
              | | | | | | | | | | | | | | | | | | | | | | | | | | | | | |
                                          C
17-3-5        | | | | | | | | 360| | | | | | | | | | | |
[ 718 ]       <++CT+++AGCC+TGT+++A+T+CC++++++A++-+G+++A+++-G+++TCC++-++G++

300
                                                                     *
1.3kb R1 h    CATAATAGGAGAAGATGCTCTGGAAGCTGTCTGAGATGGAGGCCGTGTGCACTGGCCAGG
              GTATTATCCTCTTCTACGAGACCTTCGACAGACTCTACCTCCGGCACACGTGACCGGTCC
              | | | | | | | | | | | | | | | | | | | | | | | | | | | | | |
                           AGTAAGAGA
              | | | | | | | | | | | | | | | | | | | | | | | | | | | | | |
17-3-5        | 320 | | | | | | | | |280 | | | | |
[ 718 ]       <++AC+C++T++-++T++T+A+A++T+++T++G+++G+++++A++AC+A++T+++T+T++

1.3kb R1 h    CCGTCTGGATTTCTGTAGCATTCTTCTCATTG  [ SEQ ID NO : 5 ]
              GGCAGACCTAAAGACATCGTAAGAAGAGTAAC  [ SEQ ID NO : 3 ]
              | | | | | | | | | | | | | |
17-3-5        | | | | | 240 | | | |
[ 718 ]       <TG+++++++++++C++++AG++T++++++++
```

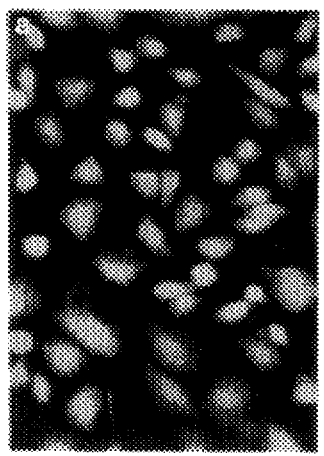 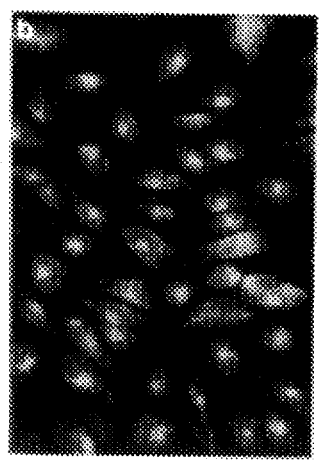 
FIG. 12 A  FIG. 12 B  FIG. 12 C

FIG. 17

```
                        11                                                          70 /
[SEQ ID NO:6]    Mmr    taevpaggrrdvpsgVkitaLatgfvmatLdVtVvnvagatigeSldttlt.........
[SEQ ID NO:7]    Tet pBR .......mksNnaLiViLgtvtLDavGIGLVmPVlPgLLrDivhSDsias..........
[SEQ ID NO:8]    Tet Tn10 .........mNsstkIaLvitLLDaMGIGLImPVlPTLLrEfiaSEdian..........
[SEQ ID NO:9]    BMR    ......mekkNitLtIlLtnLFiafLGIGLVIPVtPTiMnElhlSgt.............
[SEQ ID NO:10]   CGAT   rllkegrqsrklvLvVvFvaLLLDnMlltvVVPIvPTFLyatefkDsnsslhrgpsvssq /
[SEQ ID NO:11] Consensus ----------N--L-V-L--LLLD-MGIGLVVPV-PTLL-E---SD--------------
                                              └──────TM1──────┘

/131                                                        190
                 Mmr    ....qLtwivdgYvLtfasllmLaGgLanRiGaktVyLwGMgvffLasLacALapTaetL
                 Tet pBR ....hYGVLLAlYALMQFlcaPvlGaLsDRFGRrpVLLasLLgatidyaiMAttpvlwiL
                 Tet Tn10 ....hFGVLLAlYALMQvifaPWlGkMsDRFGRrpVLLlsLigasLdyLLLAFssalwML
                 BMR    ....avGyMvAcFAitQLivsPiaGrwvDRFGRkimiviGLLffsvseFLFgigkTveML
                 CGAT   /eenvriGILFAskALMQLlvnPPvGpLtnRiGyhipMFvGFMimfLstLMFAFsgTyaLL
                 Consensus ------GVLLA-YALMQL---P--G-L-DRFGR--VLL-GLL---L--LLFAF--T--ML
                              └──────TM2──────┘     └──────TM3──────┘

191                                                         250
                 Mmr    iaaRLvqGagaALfmpsslslLVfsfpEkrqRtRmLGlwSAivatssglGPtVGGLMvs.
                 Tet pBR YagRivaGItgA..tgAvagaYIADiTDgedRaRhFGlMSAcFgvGMVaGPvaGGLLga.
                 Tet Tn10 YlgRLLsGItgA..tgAvaasvIADtTsasqRvkwFGwLgAsFglGLIaGPiIGGFagE.
                 BMR    FitRMLgGIsapF.impgvtaFIADiTtiktRpkaLGyMSAaistGFIiGPgIGGFLaE.
                 CGAT   FvaRtLqGIgssFssvAglgmLasvyTDnyeRgRaMGialggLalGLlvGapfGsvMyEf
                 Consensus ---RLL-GI--AF---A----LIAD-TD---R-R--G-MSA-F--GLI-GP-IGG---E-
                              └──────TM4──────┘     └──────TM5──────┘

251                           290
                 Mmr    ...afgWesifLLNLpigaigMamtYryiaatEsratrla
                 Tet pBR IslhaPFLaAAvLNgLnllLgcFlMgEshkgerrpmplra
                 Tet Tn10 IsphsPFFiAALLNivtflvvMFwFREtkntrDntdtevg
                 BMR    VnsrlPFFfAAaFaLLaaiLsiLtLREpernpEngeikgq
                 CGAT   VgkssPFLilAFLaLLdgaLqLciLWpskvspEsamgtsl
                 Consensus ------PF--AALLNLL---L-MF-LRE-----E-------
                              └──────TM6──────┘
```

FIG. 21A

```
[SEQ ID NO:4]  hSVAT   MALSeLaL...vRWLqESRrSRKLILFIVFLALLLDNMLLTVVVPIIPSYLY.
[SEQ ID NO:2]  rSVAT   MALSdLVL...lRWLRdSRhSRKLILFIVFLALLLDNMLLTVVVPIIPSYLY.
[SEQ ID NO:13] rCGAT   mlqvVLgapqRlLKEgRqSRKLvLvvVFvALLLDNMLLTVVVPIIPSYLYa
                                                    └─────TM1─────┘ hSVAT   .IKHEKNaT    EIQTaRPv    htasiSdSfqSIFSYYDN  ST  mvTGNATrd
               rSVAT   .IKHEKNST    EIQTtRP     eLv vStS eSIFSYYnN  STvliTGNATgt
               rCGAT   tefkdsNSslhrgpsvssqqa    Lt  SpaFstIFSffDNttTtveeehvp..

hSVAT   L....TlhqTaTQHmVtNAsaVPSD  CPSEDkDLL  NENVQVGLLFASKATVQ
               rSVAT   LpggqshkaTsTQHTVAN.ttVPSD  CPSEDrDLL  NENVQVGLLFASKATVQ
               rCGAT   frvtwTngtipppvTeAss       VPknnC  lqgiefLeeENVriGILFASKAlmQ
                                                                    └─────TM2─ hSVAT   LiTNPFIGLLTNRIGYPIPiFAGFCIMFvSTIMFAFSSSYAFLLIARSLQGIG
               rSVAT   LLTNPFIGLLTNRIGYPIPMFAGFCIMFiSTVMFAFSSSYAFLLIARSLQGIG
               rCGAT   LLvNPFvGpLTNRIGYhIPMFvGFmIMFlSTLMFAFSgtYAlLfvARtLQGIG
                       ──────────┘   └──────TM3──────┘          └── hSVAT   SSCSSVAGMGMLASVYTDDEERGnvMGIALGGLAMGVLVGPPFGSVLYEFVGK
               rSVAT   SSCSSVAGMGMLASVYTDDEERGkpMGIALGGLAMGVLVGPPFGSVLYEFVGK
               rCGAT   SSfSSVAGLGMLASVYTDNyERGraMGIALGGLALGlLVGaPFGSVmYEFVGK
                       ──TM4──────┘           └──────TM5──────┘ hSVAT   TAPFLVLAALVLLDGAIQLFVLQPSRVQPESQKGTPLTTLLKDPYILIAAGSI
               rSVAT   TAPFLVLAALVLLDGAIQLFVLQPSRVQPESQKGTPLTTLLKDPYILIAAGSI
               rCGAT   ssPFLiLAfLaLLDGALQLciLwPSkVsPESamGTsLlTLLKDPYILvAAGSI
                       └──────TM6──────┘                        └──────TM7─ hSVAT   CFANMGIAMLEPALPIWMMETMCSRKWQLGVAFLPASISYLIGTNIFGILAHK
               rSVAT   CFANMGIAMLEPALPIWMMETMCSRKWQLGVAFLPASISYLIGTNIFGILAHK
               rCGAT   ClANMGvAiLEttLPIWMMqTMCSPeWQLGlAFLPASvaYLIGTNLFGvLAnK
                       ──────────┘          └──────TM8──────┘ hSVAT   MGRWLCALLGMiIVGvSILCIPFAKNIYGLIAPNFGVGFAIGMVDSSMMPIMG
               rSVAT   MGRWLCALLGMvIVGISILCIPFAKNIYGLIAPNFGVGFAIGMVDSSMMPIMG
               RCGAT   MGRWLCsLVGMVAVGISlLCvPlAhNIfGLIGPNaGlGFAIGMVDSSLMPIMG
                       └──────TM9──────┘      └──────TM10──
```

FIG. 21B

```
hSVAT    YLVDLRHVSVYGSVYAIADVAFCMGYAIGPSAGGAIAKAIGFPWLMTIIGIID
rSVAT    YLVDLRHVSVYGSVYAIADVAFCMGYAIGPSAGGAIAKAIGFPWLMTIIGIID
rCGAT    YLVDLRHtSVYGSVYAIADVAFCvGfAIGPStGGvIvqvIGFPqLMTIIGTIn
             └─┘   └────────TM11────────┘         └────────TM12- hSVAT    ILFAPLCFFLRSPPAKEEKMAILMDHNCPIKTKMYT QNNiQSYPIGEDEESESD*
rSVAT    IaFAPLCFFLRSPPAKEEKMAILMDHNCPIKTKMYT QNNvQSYPIGdDEESESD*
rCGAT    IiyAPLCcFLqnPPAKEEKrAIL  sqeCPteTqMYTfQkptkafPlGEnsddpSsge*
                  └─┘
```

FIG. 22A hsvatcDNA Folder Alig D Sequence

Sequence Range: 1 to 1898

```
                    10        20        30        40        50        60
[SEQ ID NO:12]       *         *         *         *         *         *
hsvatcDNA       GGCGCAAGCGACCCCGAGCGGAGCCCCGGAGCCATGGCCCTGAGCGAGCTGGCGCTGGTC 17-3-5 [SEQ ID NO:3]   50          60         70         80         90
[ 5008 ]        C+++++GT+ACAGG++++-CC+-GAG+A+++++++++++++++++++++T++++T++++C+G>
(rsvatcDNA)     |||||  |    ||||   |   |  |    |||||||||||||||||| ||||  ||||  |
hsvatcDNA       GGCGCAAGCGACCCCGAGCGGAGCCCCGGAGCCATGGCCCTGAGCGAGCTGGCGCTGGTC T         CA
[SEQ ID NO:1]                                                 |         |
5-6-1              240       250       260       270        280        |
[ 3040 ]        A+-C+C++--C+T+-CT+--C+++++TT--++++++CT++A+GTT+TT+G++T+++CC+G>
(rcgatcDNA)     | | ||  ||  | ||   |    ||     |||||  ||||| || |  | ||  ||| |
                GGCGCAAGCGACCCCGAGCGGAGCCCCGGAGCCATGGCCCTGAGCGAGCTGGCGCTGGTC 70        80        90       100       110       120
                    *         *         *         *         *         *
hsvatcDNA       CGCTGGCTGCAGGAGAGCCGCCGCTCGCGGAAGCTCATCCTGTTCATCGTGTTCCTGGCG 17-3-5           100       110        120       130        140       150
[ 5008 ]        ++A+++++++G+++C++++++++A++++++C++A++G++++++++++++++++++++T+++>
                || ||||||| ||| ||||||| ||||||| || || |||||||||||||||||||| |||
hsvatcDNA       CGCTGGCTGCAGGAGAGCCGCCGCTCGCGGAAGCTCATCCTGTTCATCGTGTTCCTGGCG 5-6-1              300       310       320        330       340       350
[ 3040 ]        ++G+T++++A++++AG+AA+G+AG++C++C+++++GG+G+++G+GG+G++++++G+++T>
                || | |||| |||| | ||  ||| ||  || ||||| |   | || |      |||| |
hsvatcDNA       CGCTGGCTGCAGGAGAGCCGCCGCTCGCGGAAGCTCATCCTGTTCATCGTGTTCCTGGCG
```

FIG. 22B

```
                   130       140.      150       160       170       180
                    *         *         *         *         *         *
hsvatcDNA   CTGCTGCTGGACAACATGCTGCTCACTGTCGTGGTCCCCATCATCCCAAGTTATCTGTAC 17-3-5      160       170       180       190       200       210
[ 5008 ]    +++++++++++++++++++++++++++C+++++++++T+++++++++++C++C+++++++++>
            |||||||||||||||||||||||||||  |||||||| |||||||||||  || |||||||||
hsvatcDNA   CTGCTGCTGGACAACATGCTGCTCACTGTCGTGGTCCCCATCATCCCAAGTTATCTGTAC 5-6-1       360       370       380       390       400       410
[ 3040 ]    +++++T+++++++++++++++++++++++G+++++G+++++TG+G++C+CC+TC+++++->
```

FIG. 22C

```
               |||||  ||||||||||||||||||||||||  |||||  |||||    |  ||  |    |  |||||
hsvatcDNA      CTGCTGCTGGACAACATGCTGCTCACTGTCGTGGTCCCCATCATCCCAAGTTATCTGTAC 190       200       210       220       230       240
                          *         *         *         *         *         *
hsvatcDNA      AGCATTAAGCATGAGAAGAATGCTACAGAAATCCAGACGGCCAGGCCAGTGCACACTGCC 17-3-5         220       230       240       250       260       270
[ 5008 ]       ++++++++++++++++++A++CT++++G+++++++++++CA+++A++++A++T+GTG+T+>
               |||||||||||||||||| || |||| |||||||||||  ||||  ||||  || |    | |
hsvatcDNA      AGCATTAAGCATGAGAAGAATGCTACAGAAATCCAGACGGCCAGGCCAGTGCACACTGCC CT            TA       CAA
                                                    |             |         |
5-6-1                    420       430       440|   450       460       470|
[ 3040 ]       C+-CGAC++AG+TCA++++CA++A++TCTTC+G++T+G++GTCCTT+T+A++T+C+A+G+>
                |   ||  |   ||||   ||  ||    ||| | ||       |||| | ||  |||||||
hsvatcDNA      AGCATTAAGCATGAGAAGAATGCTACAGAAATCCAGACGGCCAGGCCAGTGCACACTGCC
```

FIG. 22D

```
              250        260        270        280        290        300
               *          *          *          *          *          *
hsvatcDNA    TCCATCTCAGACAGCTTCCAGAGCATCTTCTCCTATTATGATAACTCGACTATGGTCACC
                          |
                          | T
                          | |
                      GCATCTTC
                      | | |
17-3-5       280      29300|   310        320        330        340
[ 5008 ]     ++++C+++C++A+T++A+T+T+A++A-C+++A++G+GT++++C+-C++GGA+-T+C+++T>
             |||| ||| || | || | | ||    ||| || |  |||| | ||  |  | | |||
hsvatcDNA    TCCATCTCAGACAGCTTCCAGAGCATCTTCTCCTATTATGATAACTCGACTATGGTCACC
                          |
              C           |                                GAC
              |           |                                 |
5-6-1        480         |490       500        510        520        530        540
[ 3040 ]     +T++C+++TCCTGC++++TCT+C+++A+++++++TC+T+++C+++A+C++C+CT++AGAA>
              | |  |||   ||||    |||| |||||||| | ||| ||| | || | ||  ||
hsvatcDNA    TCCATCTCAGACAGCTTCCAGAGCATCTTCTCCTATTATGATAACTCGACTATGGTCACC 310        320        330        340        350        360
               *          *          *          *          *          *
hsvatcDNA    GGGAATGCTACCAGAGACCTGACACTTCATCAGACCGCCACACAGCACATGGTGACCAAC

```
                        |
17-3-5        350       | 360      370       380       390       400
[ 5008 ]     ++++C-T++T++G+++GG+A+T+++ACA+GGCT+++AG++++++++++++CT+++G+T+-->
              ||||   || || |||   | | |||    |    |||  ||||||||||||| ||| | |
hsvatcDNA    GGGAATGCTACCAGAGACCTGACACTTCATCAGACCGCCACACAGCACATGGTGACCAAC TC
                                                         |
5-6-1         550       560       570       580       590       600
[ 3040 ]     +AAC++-G+++-CCTTC+G++TA++++GGA++A+TG++AC++TCC+T+CCA++C++TG+A>
              |   ||  |||      | || ||||    || | || || || | |  || ||  |
hsvatcDNA    GGGAATGCTACCAGAGACCTGACACTTCATCAGACCGCCACACAGCACATGGTGACCAAC 370       380       390       400       410       420
               *         *         *         *         *         *
hsvatcDNA    GCGTCCGCTGTTCCTTCCGACTGTCCCAGTGAAGACAAAGACCTCCTGAATGAAAACGTG 17-3-5        410       420       430       440       450       460
[ 5008 ]     A+-A++A++++C+++++G+++++++++++++++++++G++++++T++++++++G++T+++>
              |  || ||||| |||||  |||||||||||||||||||| |||||| ||||||||| || |||
hsvatcDNA    GCGTCCGCTGTTCCTTCCGACTGTCCCAGTGAAGACAAAGACCTCCTGAATGAAAACGTG TAGA
                                                         |
5-6-1         610       620       630       640          660
[ 3040 ]     ++CAG+T+A++A++AAAAA++AACTG+TTGC+++GG+T+++GT++TA++-A++++++++T>
              ||   |  | || ||    ||      |    |||  | |||  || ||  |||||||||
hsvatcDNA    GCGTCCGCTGTTCCTTCCGACTGTCCCAGTGAAGACAAAGACCTCCTGAATGAAAACGTG
```

FIG. 22F

```
               430        440        450        460        470        480
                *          *          *          *          *          *
hsvatcDNA    CAAGTTGGTCTGTTGTTTGCCTCGAAAGCCACCGTCCAGCTCATCACCAACCCTTTCATA 17-3-5         470        480        490        500        510        520
[ 5008 ]     ++++++++G+++C+++++++++++C++++++++T++++++++++C++++T+++++A++++++>
             ||||||||   ||| ||||||||||| ||||||||| |||||||||| |||| ||||| ||||||
hsvatcDNA    CAAGTTGGTCTGTTGTTTGCCTCGAAAGCCACCGTCCAGCTCATCACCAACCCTTTCATA 5-6-1          670        680        690        700        710        720
[ 3040 ]     +GGA++++GA+TC+A+++++T++A+++++TTTGA+G++A++TC+GGT++++++A++TG++>
             |   ||||  |  | | ||||||  ||||||     ||| ||  || ||  |||||| ||  ||
hsvatcDNA    CAAGTTGGTCTGTTGTTTGCCTCGAAAGCCACCGTCCAGCTCATCACCAACCCTTTCATA 490        500        510        520        530        540
```

FIG. 22G

```
                      *         *         *         *         *         *
hsvatcDNA    GGACTACTGACCAACAGAATTGGCTATCCAATTCCCATATTTGCGGGATTCTGCATCATG
                              |
17-3-5            530      540|    550       560       570       580
[ 5008 ]     +++++T+++++++++++++++++++++++++++++++++++G+++++C++C+++++++++++++>
             |||||  ||||||||||||||||||||||||||||||||||| ||||| || |||||||||||
hsvatcDNA    GGACTACTGACCAACAGAATTGGCTATCCAATTCCCATATTTGCGGGATTCTGCATCATG
                              |
5-6-1             730      740 |   750       760       770       780
[ 3040 ]     ++++CT++T++T+++++G++++++++++AC++C+++++G++++TT++C++TATG++++++>
             ||||  || || ||||| |||||||||| || ||||| |||| ||  ||   ||||||
hsvatcDNA    GGACTACTGACCAACAGAATTGGCTATCCAATTCCCATATTTGCGGGATTCTGCATCATG 550       560       570       580       590       600
                   *         *         *         *         *         *
hsvatcDNA    TTTGTCTCAACAATTATGTTTGCCTTCTCCAGCAGCTATGCCTTCCTGCTGATTGCCAGG 17-3-5            590       600       610       620       630       640
[ 5008 ]     +++A++++++++G+++++++++++++++++++++++++++++++++++++++++C++++++>
             |||  |||||||| |||||||||||||||||||||||||||||||||||||||| ||||||
hsvatcDNA    TTTGTCTCAACAATTATGTTTGCCTTCTCCAGCAGCTATGCCTTCCTGCTGATTGCCAGG 5-6-1             790       800       810       820       830       840
[ 3040 ]     +++C++++C+++C+A+++++++T+++++TG+++C+++++++C+G++AT+TG+G+++C+A>
             |||  ||||  ||| | |||||||||| ||| ||||||||| || || | | ||| |
hsvatcDNA    TTTGTCTCAACAATTATGTTTGCCTTCTCCAGCAGCTATGCCTTCCTGCTGATTGCCAGG 610       620       630       640       650       660
                   *         *         *         *         *         *
hsvatcDNA    TCGCTGCAGGGCATCGGCTCGTCCTGCTCCTCTGTGGCTGGGATGGGCATGCTTGCCAGT 17-3-5            650       660       670       680       690       700
[ 5008 ]     ++C++T+++++A++T+++++C+++++++++A++C+++++++++++++++T+++++G++++C>
             || || ||||| || ||||| |||||||| || ||||||||||||||||| ||||| |||||
hsvatcDNA    TCGCTGCAGGGCATCGGCTCGTCCTGCTCCTCTGTGGCTGGGATGGGCATGCTTGCCAGT
```

FIG. 22H

```
5-6-1            850       860       870       880       890       900
[ 3040 ]     A+T++C++A+++++T++A++T++G+TT++A+++++T++A++AC+T++G++++G++++++>
             | ||  || ||||||  ||  ||  ||  |   ||  ||||| ||  ||  |  ||  ||||| ||||||
hsvatcDNA    TCGCTGCAGGGCATCGGCTCGTCCTGCTCCTCTGTGGCTGGGATGGGCATGCTTGCCAGT 670       680       690       700       710       720
                          *         *         *         *         *         *
hsvatcDNA    GTCTACACAGATGATGAAGAGAGAGGCAACGTCATGGGAATCGCCTTGGGAGGCCTGGCC
```

FIG. 22I

```
17-3-5                710       720       730       740       750       760
[ 5008 ]       ++G+++++++++++++++G+++++G++G++GCC++++++C++T++T+++++T++++++++++>
                 ||  ||||||||||||||  |||||  ||  ||    ||||||  ||  ||  |||||  |||||||||
hsvatcDNA      GTCTACACAGATGATGAAGAGAGAGGCAACGTCATGGGAATCGCCTTGGGAGGCCTGGCC 5-6-1                 910       920       930       940       950       960
[ 3040 ]       +++++T++T++CA+CT+T++++++++G+GA+C+++++++++T++T+++++G+++++++++>
                 |||||  ||  ||   |   |  |||||||||   |   |||||||||  ||  |||||  |||||||||
hsvatcDNA      GTCTACACAGATGATGAAGAGAGAGGCAACGTCATGGGAATCGCCTTGGGAGGCCTGGCC 730       740       750       760       770       780
                        *         *         *         *         *         *
hsvatcDNA      ATGGGGGTCTTAGTGGGCCCCCCCTTCGGGAGTGTGCTCTATGAGTTTGTGGGGAAGACG
                                                 |
17-3-5                770       780       790|      800       810       820
[ 5008 ]       +++++A++++++++++++A+++++++++++++++++++++++++++++++++++++++A>
                 |||||  ||||||||||||  ||||||||||||||||||||||||||||||||||||||||||||
hsvatcDNA      ATGGGGGTCTTAGTGGGCCCCCCCTTCGGGAGTGTGCTCTATGAGTTTGTGGGGAAGACG
                                                 |
5-6-1                 970       980       990 |     1000      1010      1020
[ 3040 ]       T++++AC+TC+G+++++AG+A++T+++++A++++++A+G+++++A+++++++++C+++T+C>
                 ||||   |   |  ||||||   |  ||  ||||||  ||||||   |  |||||  ||||||||  |||  |
hsvatcDNA      ATGGGGGTCTTAGTGGGCCCCCCCTTCGGGAGTGTGCTCTATGAGTTTGTGGGGAAGACG
```

FIG. 22J

```
                 790       800       810       820       830       840
                  *         *         *         *         *         *
hsvatcDNA    GCTCCGTTCCTGGTGCTGGCCGCCCTGGTACTCTTGGATGGAGCTATTCAGCTCTTTGTG 17-3-5           830       840       850       860       870       880
[ 5008 ]     +++++C+++++++++++A++T+++T++++G++++++++++++G++++++++++++++++++>
             |||||  ||||||||||| ||  ||| ||||  ||||||||||| |||||||||||||||||||
hsvatcDNA    GCTCCGTTCCTGGTGCTGGCCGCCCTGGTACTCTTGGATGGAGCTATTCAGCTCTTTGTG 5-6-1           1030      1040      1050      1060      1070      1080
[ 3040 ]     T+A++A+++++CA+CT+++++TT+T+++C+++TC+++++++++++C+C++A++T+GCA+C>
              | ||  ||||||    |||||| | |||||  ||| |||||||||||| | || || |      |
hsvatcDNA    GCTCCGTTCCTGGTGCTGGCCGCCCTGGTACTCTTGGATGGAGCTATTCAGCTCTTTGTG 850       860       870       880       890       900
                  *         *         *         *         *         *
hsvatcDNA    CTCCAGCCGTCCCGGGTGCAGCCAGAGAGTCAGAAGGGGACACCCCTAACCACGCTGCTG 17-3-5           890       900       910       920       930       940
[ 5008 ]     ++++++++++++++A++A++++++++++++++++++++++++++T+++++G++CT+++++>
             |||||||||||||| || |||||||||||||||||||||||||||| ||||| ||  ||||||
```

FIG. 22K

```
hsvatcDNA    CTCCAGCCGTCCCGGGTGCAGCCAGAGAGTCAGAAGGGGACACCCCTAACCACGCTGCTG 5-6-1            1090      1100      1110      1120      1130      1140
[ 3040 ]     ++ATG+++T++GAAA+++TCT++T++++++GCC+T++++++TT+G++TTTG++++T++C>
             ||  ||| ||    |||    || |||||||  | |||||| | ||     ||||| ||
hsvatcDNA    CTCCAGCCGTCCCGGGTGCAGCCAGAGAGTCAGAAGGGGACACCCCTAACCACGCTGCTG 910       920       930       940       950       960
                   *         *         *         *         *         *
hsvatcDNA    AAGGACCCGTACATCCTCATTGCTGCAGGCTCCATCTGCTTTGCAAACATGGGCATCGCC 17-3-5           950       960       970       980       990      1000
[ 5008 ]     +++++T++A++++++++++++C++++++++++++++++++++++++++++G++A+++>
             |||||  || ||||||||||| ||||||||||||||||||||||||||||||  | |||
hsvatcDNA    AAGGACCCGTACATCCTCATTGCTGCAGGCTCCATCTGCTTTGCAAACATGGGCATCGCC 5-6-1           1150      1160      1170      1180      1190      1200
[ 3040 ]     ++A+++++T++++++++GG+A++A+++++T+++++++++++G++C+++++++AG+++++>
             || ||||| ||||||||   |  |     |           ||  |       ||
hsvatcDNA    AAGGACCCGTACATCCTCATTGCTGCAGGCTCCATCTGCTTTGCAAACATGGGCATCGCC
```

FIG. 22L

```
                970       980       990       1000      1010      1020
                 *         *         *         *         *         *
hsvatcDNA   ATGCTGGAGCCAGCCCTGCCCATCTGGATGATGGAGACCATGTGTTCCCGAAAGTGGCAG
                                                    |
17-3-5         1010      1020    . 1030      1040|     1050      1060
[ 5008 ]    ++++++++++C+++++++++++++++++++++++++++++++++++++++++++++++>
            ||||||||||  |||||||||||||||||||||||||||||||||||||||||||||||
hsvatcDNA   ATGCTGGAGCCAGCCCTGCCCATCTGGATGATGGAGACCATGTGTTCCCGAAAGTGGCAG
                                                    |
5-6-1          1210      1220      1230      1240  |   1250      1260
[ 3040 ]    ++A++A+++++CA+G++++++++++++++++++C+++++++++++C++++CCG+++++++>
            || ||  ||||||  |  |||||||||||||||||| ||||||||| ||||    |||||||
hsvatcDNA   ATGCTGGAGCCAGCCCTGCCCATCTGGATGATGGAGACCATGTGTTCCCGAAAGTGGCAG 1030      1040      1050      1060      1070      1080
                 *         *         *         *         *         *
hsvatcDNA   CTGGGCGTTGCCTTCTTGCCAGCTAGTATCTCTTATCTCATTGGAACCAATATTTTTGGG 17-3-5         1070      1080      1090      1100      1110      1120
[ 5008 ]    +++++++++++T+++C+C++G++G++C+++++++++++++++++++++++++++++++>
            |||||||||||| ||| | || || || ||||||||||||||||||||||||||||||||
hsvatcDNA   CTGGGCGTTGCCTTCTTGCCAGCTAGTATCTCTTATCTCATTGGAACCAATATTTTTGGG 5-6-1          1270      1280      1290      1300      1310      1320
```

FIG. 22M

```
[ 3040 ]      ++A++TC+G++T+++++++++T+++++G+GG+C++C++++++++C++G++CC+C+++++T>
              || ||  | ||  |||||||||| ||||||| |  | ||| ||||||||| || ||  | |||||
hsvatcDNA     CTGGGCGTTGCCTTCTTGCCAGCTAGTATCTCTTATCTCATTGGAACCAATATTTTTGGG 1090      1100      1110      1120      1130      1140
                       *         *         *         *         *         *
hsvatcDNA     ATACTTGCACACAAAATGGGGAGGTGGCTTTGTGCTCTTCTGGGAATGATAATTGTTGGA 17-3-5                1130      1140      1150      1160      1170      1180
[ 5008 ]      ++++++++++++++++++++++A++++++++A++++++++++++++++++G+++++++++++>
              |||||||||||||||||||||| |||||||||| ||||||||||||||||||||| ||||||||||||
hsvatcDNA     ATACTTGCACACAAAATGGGGAGGTGGCTTTGTGCTCTTCTGGGAATGATAATTGTTGGA 5-6-1                 1330      1340      1350      1360      1370      1380
[ 3040 ]      G+GT+G++TA++++G+++++TC++++++++G++CT+C+++G+T++G+++G+GGCA++A++T>
              |  |  ||  ||||  |||||   |||||||  ||  |  ||| | ||  |||  |   || ||
hsvatcDNA     ATACTTGCACACAAAATGGGGAGGTGGCTTTGTGCTCTTCTGGGAATGATAATTGTTGGA 1150      1160      1170      1180      1190      1200
                       *         *         *         *         *         *
hsvatcDNA     GTCAGCATTTTATGTATTCCATTTGCAAAAAACATTTATGGACTCATAGCTCCGAACTTT 17-3-5                1190      1200      1210      1220      1230      1240
[ 5008 ]      A++++++++++++C++C++C++++++++++T++C++++++++++++C+++++C++++++>
              |||||||||||||| || || |||||||||||| || |||||||||||||| ||||| ||||||
hsvatcDNA     GTCAGCATTTTATGTATTCCATTTGCAAAAAACATTTATGGACTCATAGCTCCGAACTTT 5-6-1                 1390      1400      1410      1420      1430      1440
[ 3040 ]      A+++++T+GC+C+++G+A++TC+G++TC+C++T++++T+++T++T++T+GC++C++TGCA>
              ||||| |   | |||   | ||  | || | || || ||| || || || ||  ||  || ||
hsvatcDNA     GTCAGCATTTTATGTATTCCATTTGCAAAAAACATTTATGGACTCATAGCTCCGAACTTT
```

FIG. 22N

```
              1210       1220       1230       1240       1250       1260
               *          *          *          *          *          *
hsvatcDNA    GGAGTTGGTTTTGCAATTGGAATGGTGGATTCGTCAATGATGCCTATCATGGGCTACCTC
                                                              |
17-3-5         1250       1260       1270       1280       1290|      1300
[ 5008 ]     +++++++++++++++++++++G++++++++C++C++T+++++++++++++++++++++G>
             |||||||||||||||||||| |||||||| || || |||||||||||||||||||||||
hsvatcDNA    GGAGTTGGTTTTGCAATTGGAATGGTGGATTCGTCAATGATGCCTATCATGGGCTACCTC
                                                              |
5-6-1          1450       1460       1470       1480       1490 |     1500
[ 3040 ]     ++CC++++C+++++C++A++++++++++++++C++TC+++++++C+++++++++A+++++G>
             || |||| ||||| || |||||||||||||| || |||||||| |||||||| |||||
hsvatcDNA    GGAGTTGGTTTTGCAATTGGAATGGTGGATTCGTCAATGATGCCTATCATGGGCTACCTC
```

FIG. 22 O

```
                1270      1280      1290      1300      1310      1320
                  *         *         *         *         *         *
hsvatcDNA    GTAGACCTGCGGCACGTGTCCGTCTATGGGAGTGTGTACGCCATTGCGGATGTGGCATTT 17-3-5          1310      1320      1330      1340      1350      1360
[ 5008 ]     ++T+++++++++++T+++++T+++++++++++++++T++T+++++++++A++C+++++C+++>
             || |||||||||||| ||||| |||||||||||||||| || |||||||| || ||||| |||
hsvatcDNA    GTAGACCTGCGGCACGTGTCCGTCTATGGGAGTGTGTACGCCATTGCGGATGTGGCATTT 5-6-1           1510      1520      1530      1540      1550      1560
[ 3040 ]     ++G+++T+A++C+++ACC++T++G+++++++++++C++T+++++C++C++++++++C+++>
             || ||| | || ||    || || |||||||||||| || ||||| || |||||||| |||
hsvatcDNA    GTAGACCTGCGGCACGTGTCCGTCTATGGGAGTGTGTACGCCATTGCGGATGTGGCATTT 1330      1340      1350      1360      1370      1380
                  *         *         *         *         *         *
hsvatcDNA    TGTATGGGGTATGCTATAGGTCCTTCTGCTGGTGGTGCTATTGCAAAGGCAATTGGATTT 17-3-5          1370      1380      1390      1400      1410      1420
[ 5008 ]     ++++++++C++++++++C+++++C+++++++++++++++C++C++++++++++++C+++>
             |||||||| |||||||| ||||| |||||||||||||||| || |||||||||||||| |||
hsvatcDNA    TGTATGGGGTATGCTATAGGTCCTTCTGCTGGTGGTGCTATTGCAAAGGCAATTGGATTT 5-6-1           1570      1580      1590      1600      1610      1620
[ 3040 ]     +++G++++C+T+++++++T++C++A+++A++++G++++T+++C+T+C+++TC++++C+++>
             ||| |||| | ||||||| || || || | |||| ||||| || | | ||| ||||| |||
hsvatcDNA    TGTATGGGGTATGCTATAGGTCCTTCTGCTGGTGGTGCTATTGCAAAGGCAATTGGATTT
```

FIG. 22 P

```
              1390      1400      1410      1420      1430      1440
               *         *         *         *         *         *
hsvatcDNA    CCATGGCTCATGACAATTATTGGGATAATTGATATTCTTTTTGCCCCTCTCTGCTTTTTT 17-3-5         1430      1440      1450      1460      1470      1480
[ 5008 ]     ++T+++++T+++++++++++++++++++++++++++++CGC++++++T++A++++++++++++C>
             || |||||| |||||||||||||||||||||||||||  |||||| || |||||||||||
hsvatcDNA    CCATGGCTCATGACAATTATTGGGATAATTGATATTCTTTTTGCCCCTCTCTGCTTTTTT 5-6-1          1630      1640      1650      1660      1670      1680
[ 3040 ]     ++T+++++++++GTC++C+++++T+CC++CA+C++CA+++A+++T+++++++++++GC++C>
             || |||||||||  || |||||| |  | || ||| ||| |||||||||||  ||
hsvatcDNA    CCATGGCTCATGACAATTATTGGGATAATTGATATTCTTTTTGCCCCTCTCTGCTTTTTT 1450      1460      1470      1480      1490      1500
```

FIG. 22Q

```
                  *         *         *         *         *         *
hsvatcDNA    CTTCGAAGTCCACCTGCCAAAGAAGAAAAAATGGCTATTCTCATGGATCACAACTGCCCT
                                                                        |
17-3-5           1490      1500      1510      1520      1530      1540|
[ 5008 ]     ++++++++++++++++++T++G++G++++++++++++++C++++++++C++++++++T++C>
             |||||||||||||||||| || || |||||||||||||| |||||||| |||||||| ||
hsvatcDNA    CTTCGAAGTCCACCTGCCAAAGAAGAAAAAATGGCTATTCTCATGGATCACAACTGCCCT
                                                                        |
5-6-1            1690      1700      1710      1720      1730      1740
[ 3040 ]     ++G+AG+AC++G++A++T++G++G++G++GCGT++A++++---++AGC++GG+A+++++C>
             ||| |  || || || || || || || || ||||  ||         ||| || |  |||||
hsvatcDNA    CTTCGAAGTCCACCTGCCAAAGAAGAAAAAATGGCTATTCTCATGGATCACAACTGCCCT 1510      1520      1530      1540      1550      1560
                  *         *         *         *         *         *
hsvatcDNA    ATTAAAACAAAAATGTACACTCAGAATAATATCCAGTCATATCCGATAGGTGAAGATGAA 17-3-5           1550      1560      1570      1580      1590      1600
[ 5008 ]     +++++++++++G++++++++++++++++++G+++++++++++++C++C++++T++++++>
             ||||||||||| |||||||||||||||||| |||||||||||| || ||||| ||||||
hasvatcDNA   ATTAAAACAAAAATGTACACTCAGAATAATATCCAGTCATATCCGATAGGTGAAGATGAA CAT
                                 |
5-6-1            1750            | 1770      1780      1790      1800
[ 3040 ]     +CAG+G++CC+G+++++++TC+++++GCCC+CAA++G+G+T+++AC++++A-G++-AAC+>
             |  |  ||  | |||||||  |||||  |||| ||   | | |  || |||| || || |
hsvatcDNA    ATTAAAACAAAAATGTACACTCAGAATAATATCCAGTCATATCCGATAGGTGAAGATGAA
```

FIG. 22R

```
                  1570      1580      1590      1600      1610      1620
                    *         *         *         *         *         *
hsvatcDNA    GAATCTGAAAGTGACTGAGATGAGATCCTCAAAAATCATCAAAGTGTTTAATTGTATAAA 17-3-5              1610       1620      1630
[ 5008 ]     ++++++++++++++-----C+++++C++++T++CG+>
             ||||||||||||||     |||||  ||||  ||  |
hsvatcDNA    GAATCTGAAAGTGACTGAGATGAGATCCTGAAAAAT 5-6-1               1810      1820      1830      1840      1850
[ 3040 ]     -GCGA+++TCC+AG+A+C+GG+++TAA++GCGG+GGGCGAT+TC+-GAGCC+CAC+-TCT>
               |||    |||  ||  |  ||   |||   ||||  |||||| ||   |||||  ||   |||
hsvatcDNA    GAATCTGAAAGTGACTGAGATGAGATCCTCAAAAATCATCAAAGTGTTTAATTGTATAAA 1630      1640      1650      1660      1670      1680
                    *         *         *         *         *         *
```

FIG. 22S

```
hsvatcDNA    ACAGTGTTTCCAGTGACACAACTCATCCAGAACTGTCTTAGTCATACCATCCATCCCTGG 5-6-1          1860      1870      1880      1890      1900      1910
[ 3040 ]     +++-G-GGA++++-TCT++T++AG++T++AT+A-T+T+C+C-TT+C+TC++-C-T++A++>
              |||     ||||    || ||   || ||  |   |||    || ||   || ||
hsvatcDNA    ACAGTGTTTCCAGTGACACAACTCATCCAGAACTGTCTTAGTCATACCATCCATCCCTGG 1690      1700      1710      1720      1730      1740
                         *         *         *         *         *         *
hsvatcDNA    TGAAAGAGTAAAACCAAAGGTTATTATTTCCTTTCCATGGTTATGGTCGATTGCCAACAG 5-6-1          1920      1930      1940      1950      1960
[ 3040 ]     CC+CT+CC+TCCT+-CCTTC++++GA+A+++++++T+TAC+CACC+GT+AGTG+++-CC>
              |  |  |  |     |||||  | |||||||| |   |   |    ||  |||
hsvatcDNA    TGAAAGAGTAAAACCAAAGGTTATTATTTCCTTTCCATGGTTATGGTCGATTGCCAACAG 1750      1760      1770      1780      1790      1800
                         *         *         *         *         *         *
hsvatcDNA    CCTTATAAAGAAAAAGAAGCTTTTCTAGGGGTTTGTATAAATAGTGTTGAAACTTTATTT
                          |
                          |        TGACACC                       T
                          |          |                           |
5-6-1          970      1980      1992000     2010      2020      2030
[ 3040 ]     +ACC+CTCTCCCTCT-GT++++AC+C+T++CCCAC+T+TTG-T+G+AG++C+GGC+++++>
              |  |   |||||| || || |  |  |    ||  |  |    | || |  |||||
hsvatcDNA    CCTTATAAAGAAAAAGAAGCTTTTCTAGGGGTTTGTATAAATAGTGTTGAAACTTTATTT
```

FIG. 22T

```
              1810       1820       1830       1840       1850       1860
               *          *          *          *          *          *
hsvatcDNA   TATGTATTTAATTTTATTAAATATCATACAATATATTTTGATGAAATAGGTATTGTGTAA 5-6-1         2040       2050       2060       2070       2080       2090
[ 3040 ]    CC+--GCCAGGCCAA+GCG++GC+G++TA++GC+GAG++-G+++C-A++T+C+GCAAGGG>
               |          |  ||  |  ||  ||  |   ||  |||     ||  | |
hsvatcDNA   TATGTATTTAATTTTATTAAATATCATACAATATATTTTGATGAAATAGGTATTGTGTAA 1870       1880       1890
               *          *          *
hsvatcDNA   ATCTATAAATATTTGAATCCAAACCAAATATAATTTCC 5-6-1         2100       2110       2120
[ 3040 ]    G+GAC+C+C+TCC++C+GG++GGA+TG-A+C+++G+G>
             |  ||| |  ||  ||  |   ||||  |
hsvatcDNA   ATCTATAAATATTTGAATCCAAACCAAATATAATTTC
```

VESICLE MEMBRANE TRANSPORT PROTEINS

CROSS-REFERENCES

This application is a continuation-in-part of U.S. application Ser. No. 07/923,096 by Robert H. Edwards, filed Jul. 30, 1992, and entitled "Vesicle Membrane Transport Proteins", now abandoned, which in turn is a continuation-in-part of U.S. application Ser. No. 07/899,074 by Robert H. Edwards, filed Jun. 11, 1992 and also entitled "Vesicle Membrane Transport Proteins", now abandoned. Both of these applications are incorporated herein by this reference.

GOVERNMENT RIGHTS

This invention was made with governmental support under National Science Foundation (NSF) grant number BNS 90-11993. The government has certain rights in the invention.

BACKGROUND OF THE INVENTION

The present invention relates to the identification, production and manipulation of vesicle membrane transport proteins, and more particularly to the mammalian vesicle amine transport proteins, and to methods of using the vesicle transport proteins to treat Parkinson's disease and other neurological and psychiatric disorders and to screen for drugs that modulate the activity of the transport proteins.

Vesicle membrane transport proteins are membrane-bound proteins that actively transport substances into vesicles such as synaptic vesicles within cells. Vesicle transport activities have been identified for the amines, acetylcholine, gamma-aminobutyric acid (GABA), glycine and glutamate (Burger et al., Neuron 7(2):287–93 (1991); Hell et al., J. Biol. Chem. 265(4):2111–7 (1990)); Maycox et al., J. Biol. Chem. 263(30):15423–8 (1988); Hicks et al., J. Neurochem. 57(2):509–19 (1991); Kish et al., Proc. Natl. Acad. Sci. USA 86:3877–3881 (1989); Carlson et al., J. Biol. Chem. 264:7369–7376 (1989) and Stern-Bach et al., J. Biol. Chem. 265:3961–3966 (1990)). Most activities appear to depend on an electrochemical gradient across the vesicle that is generated by the vesicular $H^+$-ATPase. Several of these activities have been reconstituted in lipid vesicles, but only the chromaffin granule amine transporter has been purified to any extent (Stern-Bach et al., supra). Binding of [$^3$H]reserpine to this transporter has suggested a molecular weight of 80 kilodaltons (Kd) but no cDNA clone has been made available for this transporter or any other neurotransmitter transporter.

It has been proposed that a neurotoxic insult removes a portion of dopamine neurons and results in the appearance of Parkinsonian symptoms when the dopamine cell population and function decrease below a threshold level (Calne and Langston, Lancet ii, 1457–1459 (1983)). Damage to central dopamine neurons in primates (Langston et al., Science 219:979–980 (1983); and Burns et al., Proc. Natl. Acad. Sci. USA 80:4546–4550 (1983)) and to dopamine nerve terminals in mice (Heikkila et al., Science 224:1451–1452 (1984)) caused by the neurotoxin 1-methyl-4-phenyl-1,2,3,6-tetrahydropyridine (MPTP) has been suggested as a model of Parkinson's disease. The development of MPTP neurotoxicity requires its conversion to the active metabolite 1-methyl-4-phenylpyridinium ($MPP^+$) by the B isozyme of monoamine oxidase (Chiba et al., Biochem. Biophys. Res. Commun. 120:574–578 (1984); Heikkila, supra; Langston et al., Science 225:1480–1482 (1984); and Markey et al., Nature 311:464–466 (1984)). Dopaminergic cells of the substantia nigra then accumulate high levels of $MPP^+$ by uptake through the high-affinity plasma membrane catecholamine transporter (Javitch et al., Proc. Natl. Acad. Sci. USA 82:2173–2177 (1985); and Snyder et al. in MPTP: A Neurotoxin Producing a Parkinsonian Syndrome, (eds. Markey et al., Academic Press, New York), pp. 191–201 (1986)). Inside the cell, $MPP^+$ enters mitochondria (Ramsay and Singer, J. Biochem. 261:7585–7587 (1986)) and inhibits respiration at the level of complex I, apparently by binding near the site of action of the other mitochondrial toxins rotenone and piericidin (Krueger et al., Biochem. Biophys. Res. Comm. 169:123–128 (1990); and Ramsay et al., J. Neurochem. 56:1184–1190 (1991)).

Because MPTP reproduces the pattern of neuronal degeneration observed in Parkinson's disease (PD), this form of toxicity has been used as a model system to dissect the cellular components responsible for selective neuronal vulnerability in the idiopathic human disease. Studies of patients with Parkinson's disease support the utility of MPTP as a model for PD. Both brain tissue and circulating platelets from patients with PD show a selective reduction in the same mitochondrial component affected by MPTP, respiratory complex I (Mizuno et al., Biochem. Biophys. Res. Comm. 163:1450–1455 (1989); Parker et al., Ann. Neurol. 26:719–723 (1989) and Shoffner et al., Ann. Neurol. 30:332–339 (1991)). Deprenyl, which inhibits the enzyme that activates MPTP, monoamine oxidase, also appears to slow the rate of progression in idiopathic PD (Parkinson Study Group, New Engl. J. Med. 321:1364–1371 (1989)). However, Parkinsonism induced by MPTP develops over days to weeks whereas idiopathic PD develops over years. Explanations for the relatively slow rate of progression in idiopathic PD include chronic, low levels of exposure to an environmental toxin similar to MPTP, oxidative stress related to the cytoplasmic accumulation of dopamine, or the trapping of free radicals by deposited dopamine and lipofuscin that predisposes these cells to mitochondrial injury (Cohen, J. Neural Transmission Suppl. 32:229–238 (1990)).

The MPTP model has led to the identification of multiple pathogenetic factors that may also contribute to idiopathic Parkinson's disease. The amelioration of toxicity with an excitatory amino acid antagonist suggests that neural excitation plays a role in the injury produced by $MPP^+$ in vivo (Turski et al., Nature 349:414–418 (1991)). In addition, neurotrophic factors such as brain-derived neurotrophic factor (BDNF) can protect midbrain cells from $MPP^+$ in vitro (Hyman et al., Nature 350:230–232 (1991)). However, accumulation of the toxin through a high-affinity plasma membrane catecholamine transporter is required for susceptibility to MPTP in vivo. The expression of this transport activity accounts for the selective cell vulnerability observed in both the MPTP model and idiopathic PD, with several notable exceptions.

Adrenal chromaffin cells and postganglionic sympathetic neurons express a high-affinity catecholamine uptake system, but unlike dopaminergic neurons in the midbrain, do not degenerate in response to MPTP or in most cases of idiopathic PD. Chromaffin cells have even been demonstrated to accumulate [$^3$H]-$MPP^+$ but with relatively little toxicity. (Reinhard et al., Proc. Natl. Acad. Sci. USA 84:8160–8164 (1987)). Reinhard et al. proposed that the selective resistance of adrenal medulla cells to $MPP^+$ was due to subcellular compartmentalization of the neurotoxin within catecholamine storage vesicles. These researchers demonstrated that when chromaffin cells were incubated with $MPP^+$ in the presence of tetrabenazine, an inhibitor of vesicular uptake, that chromaffin cell toxicity was potentiated. They proposed that the relative resistance of some brain monoaminergic neurons to the toxic actions of MPTP may result from subcellular sequestration of MPP$^+$ within the norepinephrine neuron's catecholamine storage vesicle. However, these researchers did not isolate or identify a vesicle membrane transport protein responsible for uptake of MPP$^+$.

Rat pheochromocytoma 12 (PC12) cells derive from the adrenal gland and, although they have served as a model system to understand MPP$^+$ toxicity, PC12 cells show little susceptibility to the toxin, with 1 mM MPP$^+$ resulting in cell death by four days and 100 μM MPP$^+$ resulting in death by two weeks (Greene and Rein, Brain Res. 129:247–263 (1978); and Denton and Howard, J. Neurochem. 49:622–630 (1987)). Furthermore, inhibition of high-affinity plasma membrane uptake by tricyclic antidepressant drugs protects PC12 cells entirely from MPP$^+$, indicating that without an active system for its accumulation, these cells are intrinsically resistant to the effects of the toxin (Snyder et al., supra). Therefore, the resistance of PC12 cells to MPP$^+$ toxicity can be used to dissect the differential MPP$^+$ susceptibility of aminergic cell populations in the midbrain, and adrenal gland as well as perhaps sympathetic ganglia.

In addition to MPP$^+$, exposure of neurons to other toxic compounds, including the excitatory neurotransmitters glutamate and aspartate, may be implicated in diseases. For example, N-methyl-D-aspartate (NMDA) antagonists prevent hypoxia as well as other forms of neuronal injury (Choi et al., Annu. Rev. Neurosci. 13:171–182 (1990)). Effective sequestration of such toxic compounds into vesicles may prevent neuronal injury.

Transport and intracellular sequestration of various amines has implications for the diagnosis and treatment of psychiatric disorders including affective disorders (Carlsson, J. Psychopharmacol. 4:12–126 (1990)) and schizophrenia (Wyatt et al., Schizophr. Res. 1:3–18 (1988)) in which an imbalance of amines is involved.

Vesicle membrane transport proteins have been identified (Johnson, Physiol. Rev. 68:232–307 (1988); Anderson et al., Biochem. 21:3037–3043 (1982); Hell et al., EMBO J. 7:3023–3029 (1988); Kish et al., supra; Maycox et al., supra; and Carlson et al., supra) but have not been isolated, cloned and expressed. It is difficult to clone mammalian vesicle membrane transport proteins in part because of the difficulties in purifying low abundance, hydrophobic membrane proteins that constitute less than 0.2% of the membrane protein. Thus, these proteins are available in small quantities only from mammalian vesicle membranes. Therefore, it would be desirable to have available a method for producing practical quantities of vesicle membrane transport proteins and for studying the properties and uses of these proteins.

It would be particularly desirable to determine the location of the chromosomal gene for human central nervous system synaptic vesicle amine transporter as well as to produce a cDNA coding for this gene product, in order to produce useful quantities of this protein for studies to determine the relationship of biogenic amine metabolism to human disease.

A wide range of clinical disorders and pharmacologic agents have implicated the monoamines in consciousness, motivation, the organization of thought, mood, motor control, sensory perception and such autonomic phenomena as heart rate, vascular tone, and blood pressure. However, the role of monoamines in human disease remains unclear.

In particular, it is not known whether changes in monoamine metabolism cause the various disorders or results from them. Nonetheless, diverse human conditions including affective disease, schizophrenia, and vascular headache have a substantial inherited component, suggesting that a genetic defect in synaptic transmission by the monoamines may be responsible. However, the difficulty in diagnosis of the syndromes and their probable genetic heterogeneity complicate attempts to identify the genes responsible by standard linkage analysis (K. K. Kidd, Social Biol. 38:163–178 (1991).

On the other hand, components of the signaling apparatus from monoamines indicate specific candidate genes. The dramatic behavioral effects of drugs that affect monoamine transport further suggest the corresponding genes as candidates of particular importance for human neuropsychiatric illness (G. F. Koob & F. E. Bloom, Science 242:715–723 (1988)).

Although the molecular basis for many aspects of synaptic transmission by the monoamines has been characterized in considerable detail, the role of transport in this process has eluded characterization at the molecular level until relatively recently. Two types of transport activity participate in synaptic transmission by the amines (B. I. Kanner & S. Schuldiner, CRC Crit. Rev. Biochem. 22:138 (1987). One type occurs at the plasma membrane and terminates the action of the neurotransmitter by removing it from the synapse into the cytoplasm of the presynaptic cell. This transport activity uses the cotransport of Na$^+$ to drive uptake of the monoamine. Cocaine and the tricyclic antidepressants act by inhibiting this activity, which presumably increases the synaptic level of neurotransmitter and so elevates mood. (J. Axelrod et al., Science 133:383–384 (1961); L. L. Iversen, "The Uptake of Biogenic Amines" in Handbook of Psychopharmacology (S. D. Iversen & S. H. Snyder, eds., Plenum Press, New York (1976)).

Molecular cloning has identified three distinct plasma membrane monoamine transporters, one for norepinephrine (T. Pacholczyk et al., Nature 350:350–354 (1991)), another for dopamine (B. Giros et al., FEBS Lett. 295:149–154 (1991); J. E. Kilty et al., Science 254:578–579 (1991); S. Shimada et al., Science 254:576–578 (1991); T. B. Usdin et al., Proc. Natl. Acad. Sci. USA 88:1168–1171 (1991)), and a third for serotonin (R. D. Blakeley et al., Nature 354:66–70 (1991); B. J. Hoffman et al., Science 254:579–580 (1991)). In addition, the similarity of these transporters to the plasma membrane transporters for a variety of other classical transmitters indicates that these proteins comprise a large, closely related family (G. R. Uhl, Trends Neurosci. 15:265–268 (1992)). The plasma membrane glutamate transporters form yet another distinct family (Y. Kanai & M. A. Hediger, Nature 360:467–471 (1992); G. Pines et al., Nature 360:464–467 (1992); T. Storck et al., Proc. Natl. Acad. Sci. USA 89:10955–10959 (1992)).

In contrast, the vesicular amine transporters serve a different function in synaptic transmission, have a distinct mechanism and pharmacology, and show no structural similarity to the large group of characterized plasma membrane transporters. Vesicular monoamine transport activity packages neurotransmitter so that its release can be regulated by neuroactivity (P. D. de Camilli & R. Jahn, Ann. Rev. Physiol. 52:625–645 (1990); R. B. Kelly, Curr. Opin. Cell Biol. 3:654–660 (1991); W. S. Trimble et al., Ann. Rev. Neurosci. 14:93–122 (1991)). The activity occurs on the membrane of vesicles rather than on the plasma membrane and functions as a proton exchanger, using the proton electrochemical gradient generated by the vesicular H$^+$-ATPase to drive the uptake of monoamines from the cytoplasm. Reserpine and tetrabenazine inhibit this transport activity, and in contrast to the inhibitors of plasma membrane amine transport, may induce rather than alleviate a form of depression (E. D. Frize, *New Engl. J. Med.* 251:1006–1008 (1954)). Thus, vesicular amine transport plays a critical role in synaptic transmission by the monoamines and a defect in its expression or regulation may contribute to psychiatric disease.

Because of this likely role of vesicular amine transport proteins in both Parkinson's Disease and psychiatric disease states, it would therefore be highly desirable to isolate both genomic DNA for the human central nervous system membrane vesicle amine transport protein, as well as cDNA corresponding to the messenger RNA for the protein. Such isolated genomic DNA and cDNA would allow the determination of the similarity of the sequences involved to those of the chromaffin granule amine transporter, and would allow the use of the nucleic acid as a probe for diagnostic purposes, for expression in suitable host cells to produce recoverable quantities of the protein, and for genetic therapy of disease. Such recoverable quantities of the protein could be used for studies of drugs and toxins for their effect on the conditions believed to be associated with central nervous system vesicle monoamine transport activity.

SUMMARY OF THE INVENTION

The invention provides a means for obtaining mammalian vesicle membrane transport proteins in quantity.

Thus, in one aspect, the invention relates to recombinantly produced mammalian vesicle membrane transport protein. This protein has an amino acid sequence substantially similar to that shown in FIG. 1, (SEQ ID NO: 2) FIG. 2 (SEQ ID NO: 4) or FIG. 3 (SEQ ID NO: 13). FIG. 1 shows the nucleotide and amino acid sequence of a rat chromaffin granule amine transport protein (rCGAT), FIG. 2 the nucleotide and amino acid sequence of a rat synaptic vesicle amine transport protein (rSVAT), and FIG. 3 the nucleotide and amino acid sequence of a human synaptic vesicle amine transport protein (hSVAT) (SEQ ID NO: 1, 2, 3, 4, 12, & 13). Functional equivalents of transport protein having either the amino acid sequence of FIG. 1, FIG. 2, or FIG. 3 (SEQ ID NO: 2, 4, & 13) and having vesicle membrane transport activity are also within the invention. In particular, the proteins of the invention include proteins related to the proteins depicted in FIG. 1, FIG. 2, or FIG. 3 (SEQ ID NO: 2, 4, & 13) by one or more conservative amino acid substitutions substantially preserving the structure of the transmembrane domains.

Also within the scope of the invention is a protein having vesicular amine transport activity and encoded by genomic DNA having at least about 60% homology in its exons with at least one of the DNA sequences of FIG. 1, FIG. 2, or FIG. 3 (SEQ ID NO: 1, 3, & 12).

The invention further relates to cDNA sequences and genomic DNA sequences encoding mammalian vesicle membrane transport protein, to expression vectors suitable for production of this protein, to recombinant host cells transformed with these vectors, and to methods for producing recombinant vesicle membrane transport protein.

Among the genomic DNA sequences within the scope of the invention is substantially purified genomic DNA whose exons encode mammalian vesicle membrane transport protein.

Among the genomic DNA sequences within the scope of the invention is a human genomic DNA sequence, particularly a human genomic DNA sequence having at least about 70% homology in one of its exons with a portion of the cDNA sequence shown in FIG. 2 extending from about base 220 to about base 540 (SEQ ID NO: 3).

Another aspect of the invention is an expression vector for mammalian vesicle membrane transport protein comprising a cDNA sequence according to the present invention operably linked to at least one control sequence compatible with a suitable host cell.

Yet another aspect of the invention is a host cell transformed with an expression vector according to the present invention in a manner allowing the transformed host cell to express the transport protein encoded by the cDNA incorporated within the expression vector in a detectable quantity.

Another aspect of the invention is a method for obtaining at least one gene that encodes mammalian vesicle membrane transport protein. The method comprises hybridizing a cDNA according to the present invention as a detectable probe with DNA containing at least one gene encoding mammalian vesicle membrane transport protein in order to obtain the gene in substantially purified form.

Another aspect of the invention is a method for producing adrenal-specific or brain-specific mammalian vesicle membrane transport protein comprising:

(1) culturing a host cell according to the present invention transformed with an appropriate expression vector;

(2) using the cultured host cell to express the transport protein; and (3) purifying the protein.

In other aspects, the invention relates to compositions containing mammalian vesicle membrane transport protein, and to methods of using these compositions. These methods include a method for screening a cytotoxic reagent to determine whether cytotoxicity of the reagent is reduced by sequestration of the reagent in intracellular vesicles. The methods of the invention also include a method for identifying a compound that selectively inhibits or activates the activity of a membrane transport protein, and a method for identifying a tissue-specific inhibitor of the transport protein.

In another aspect, the invention relates to methods for the qualitative and quantitative assay of vesicular membrane transport protein.

In yet another aspect, the invention relates to antibodies specific for transport protein and to methods of using these antibodies. The antibodies can be polyclonal or monoclonal.

In yet another aspect, the invention relates to a method for detecting a chromosomal abnormality in human chromosome 10. The method comprises:

(1) hybridizing a labeled single-stranded nucleic acid sequence of sufficient length to hybridize specifically to chromosomal DNA and whose sequence is derived from the human SVAT gene to human chromosomal DNA; and (2) detecting the hybridized labeled nucleic acid sequence to determine the presence or absence of an abnormality in human chromosome 10.

BRIEF DESCRIPTION OF THE DRAWINGS

These and other features, aspects, and advantages of the present invention will become better understood with reference to the following description, appended claims, and accompanying drawings where:

FIG. 1 is the cDNA sequence and predicted amino acid sequence of the rat chromaffin granule amine transporter protein, as described in Examples 1 and 2, infra (nucleotide sequence of cDNA clone $mpp^{res}$, with the deduced amino acid sequence below; transmembrane domains are underlined and potential sites for N-linked glycosylation are indicated by an asterisk below) (SEQ ID NO: 1 and 2).

FIG. 2 is the cDNA sequence and predicted amino acid sequence of the rat synaptic vesicle amine transporter protein, as described in Example 3, infra, with transmembrane domains and potential sites for N-linked glycosylation indicated as in FIG. 1 (SEQ ID NO: 3 and 4).

FIG. 3 is the cDNA sequence and predicted amino acid sequence of the human synaptic vesicle amine transporter protein, as described in Example 4, infra, with transmembrane domains and potential sites for N-linked glycosylation indicated as in FIG. 1 (SEQ ID NO: 12 and 13).

FIG. 5 is the sequence (SEQ ID NO: 5) of a portion of human genomic DNA hybridizing to the cDNA sequence of FIG. 2 (SEQ ID NO: 3), showing the homology.

FIG. 6b: rotenone).

FIG. 8b: wild-type CHO cells).

FIG. 9b and 9c: $MPP^+$-resistant CHO cells).

FIG. 12a–12c are photographs of glyoxylic acid-induced fluorescence of cells loaded with exogenous dopamine as described in Example 2, infra (FIG. 12a: wild-type CHO cells; FIG. 12b: $MPP^+$-resistant CHO cells; FIG. 12c: effects of reserpine on $MPP^+$-resistant CHO cells).

FIG. 15B: determination of $K_m$ for dopamine by Lineweaver-Burke plot; FIG. 15C: dose-response study of inhibition by reserpine, tetrabenazine, and cocaine).

FIG. 17 is a diagram showing the alignment of the N-terminal domains of the methylenomycin$^{res}$ (Mmr) (SEQ ID NO: 6), tetracycline$^{res}$ pBR (SEQ ID NO: 7), Tet Tn10 (SEQ ID NO: 8) and bacterial multi-drug resistance (BMR) (SEQ ID NO: 9) transporters, with the vesicle membrane amine transport protein (CGAT) (SEQ ID NO: 10) (part of SEQ ID NO: 2) as described in Example 2, infra (shared residues are capitalized and shown below as a consensus sequence (SEQ ID NO: 11); the regions in brackets indicate the predicted transmembrane helices).

FIG. 19 is an autoradiograph showing the results of in situ hybridization of an antisense RNA probe corresponding to the synaptic vesicle amine transport protein to sections of the brain.

FIG. 21 is a diagram showing a comparison of the amino acid sequences (SEQ ID NO: 4, 2, and 13) predicted to result from translation of the cDNA sequences for rat SVAT, rat CGAT, and human SVAT (SEQ ID NO: 3, 1, and 12), as aligned for maximum homology.

FIG. 22 is a diagram showing a comparison of the cDNA sequences for rat CGAT and human SVAT (SEQ ID NO: 1 and 12), as aligned for maximum homology, and for rat SVAT and human CGAT (SEQ ID NO: 3 and 12), as aligned for maximum homology.

DESCRIPTION

Figure 4:
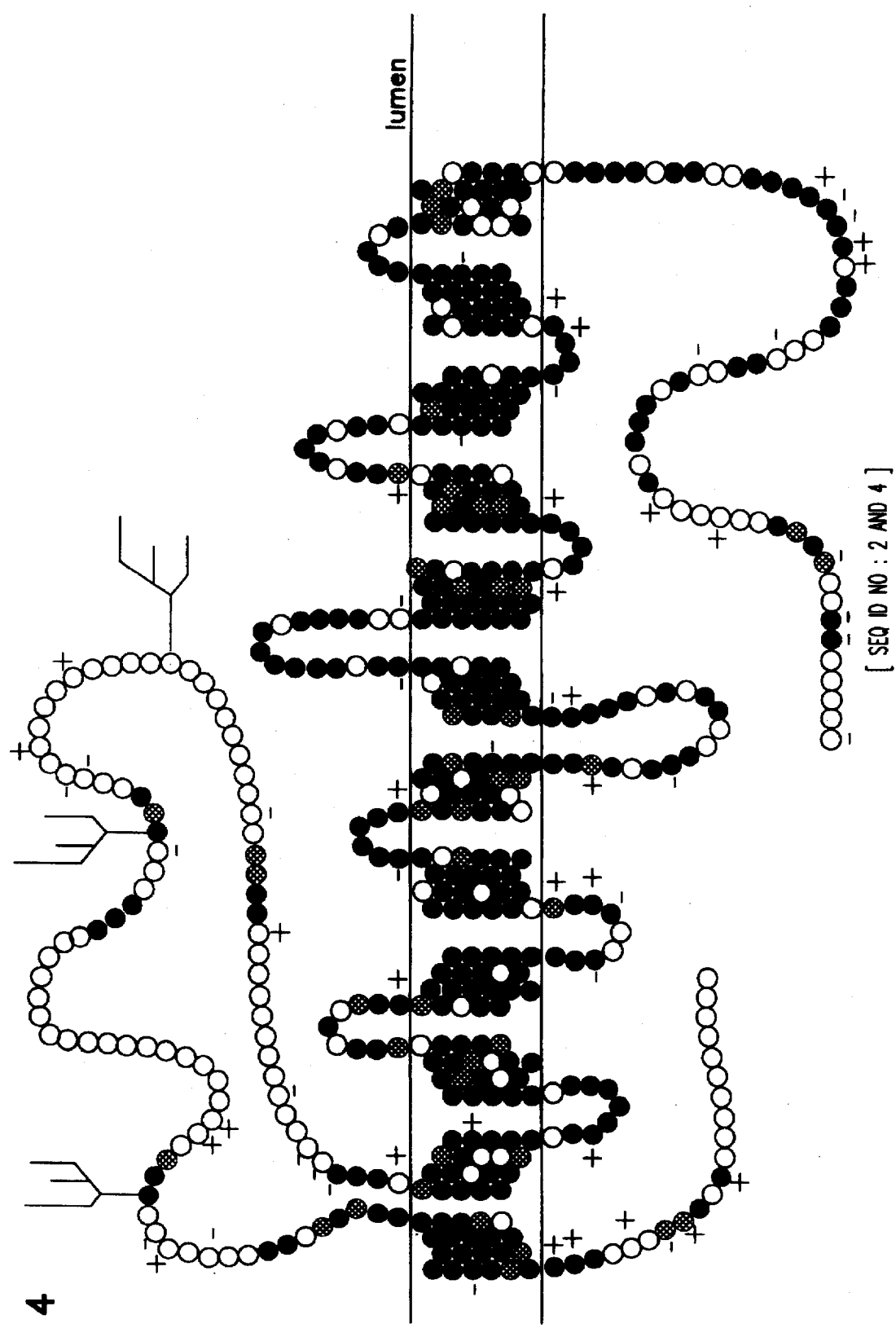
FIG. 4 is a drawing showing the homology between the rat chromaffin granule amine transporter protein and the rat synaptic vesicle amine transporter protein, with identical residues in black and conservative changes in shading (SEQ ID NO: 2 and 4).

In order that the invention herein described may be more fully understood, the following description is set forth.

Definitions

As used herein, "mammalian vesicle membrane transport protein" refers to the mammalian vesicle membrane transport protein expressed from a clone obtained as described below. This protein can be either of rat or human origin. Proteins of rat origin include adrenal-specific chromaffin-granule amine transporter protein (rCGAT protein) and brain-specific synaptic vesicle amine transporter protein (rSVAT protein). Proteins of human origin include brain-specific synaptic vesicle amine transporter protein (hSVAT protein). These proteins have an amino acid sequence substantially similar to the amino acid sequences shown in FIGS. 1, 2, or 3, (SEQ ID NO: 2, 4, & 13) but minor modifications of this sequence which do not substantially alter activity also fall within the definition and within the protein of the invention. Also included within the definition are fragments of the entire sequence encoding the protein which retain activity. This protein has no homology with the amino acid sequence of known proteins from other mammalian tissues and remote homology with a class of bacterial transport proteins.

As is the case for all proteins, vesicle membrane transport protein can occur in neutral form or in the form of basic or acid addition salts, depending on its mode of preparation, or, if in solution, upon its environment. In addition, the protein can be modified by combination with other biological materials such as lipids and carbohydrates, or by side chain modification, such as acetylation of amino groups, phosphorylation of hydroxyl side chains, or oxidation of sulfhydryl groups, or other modification of the encoded primary sequence. In its native form, the vesicle membrane transport protein is probably a glycosylated protein and is associated with phospholipids. Included within the definition of the protein herein are glycosylated and unglycosylated forms, hydroxylated and nonhydroxylated forms, and any composition of an amino acid sequence substantially similar to that shown in FIGS. 1 or 2 (SEQ ID NO: 2 & 4) which retains the ability of the protein to transport substances including amine transmitters as well as acetylcholine, glutamate, glycine and gamma-aminobutyric acid (GABA), across vesicle membranes.

It is further understood that minor modifications of primary amino acid sequence may result in proteins that have substantially equivalent or enhanced activity as compared to the sequences set forth in FIG. 1, FIG. 2 or FIG. 3 (SEQ ID NO: 1, 2, 3, 4, 12 & 13). These modifications can be deliberate, as by site-directed mutagenesis, or can be accidental, for example by mutation of hosts that are organisms that produce the vesicle membrane transport protein. All of these modifications are included in the definition provided that activity of the protein is retained.

The term "functional equivalents" as used herein refers to proteins having physical and chemical properties substantially equivalent to proteins whose primary amino acid sequences are set forth in FIG. 1, FIG. 2, or FIG. 3 (SEQ ID NO: 2, 4, & 13). These properties include molecular weight, state of aggregation, charge, transport activity, and affinity for substrates, inhibitors, and/or modulators of activity.

"Activity" of the protein is defined as transport into a vesicle derived from transfected cells or into liposomes reconstituted with the transport protein. For example, neural or non-neural mammalian cells, or cells from lower organisms are transfected with the cloned cDNA encoding the vesicle membrane transport protein in a suitable expression vector. The membranes are then isolated from the transfected cells after homogenization, and are incubated, e.g. at 20°–37° C. for from 2 to 45 minutes, in an appropriate buffer containing ATP. The uptake of radiolabelled neurotransmitters is then measured by filtering the mixture and counting the bound fluid material using a scintillation counter. In addition, the vesicle membrane transport protein can be reconstituted in lipid vesicles and uptake into these vesicles is measured as above in the presence of a superimposed electrochemical gradient needed to drive transport developed in vivo by the vesicular ATPase, or in vitro by either the endogenous ATPase, an exogenous ATPase or an artificial gradient. Carlson et al., *J. Biol. Chem.* 264:7369–7376 (1989); Maycox et al., *J. Biol. Chem.* 263:15423–15428 (1988); Maycox et al., *EMBO J* 9:1465–1469 (1990); Hell et al., *J. Biol. Chem.* 265:2111–2117 (1990) and Hell et al., *Biochem.* 30:11795–11800 (1991)).

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host employed.

"Operably linked" refers to a positional arrangement wherein the components are configured so as to perform their usual function. Thus, control sequences operably linked to coding sequences are capable of effecting the expression of the coding sequence.

"Cells" or "recombinant host cells" or "host cells" are often used interchangeably herein as will be clear from the context. These terms include the immediate subject cell, and the progeny thereof. It is understood that not all progeny are exactly identical to the parental cell, due to chance mutations or differences in environment. However, such altered progeny are included when the above terms are used.

I. METHODS FOR OBTAINING AND EXPRESSING cDNA CODING FOR MAMMALIAN VESICLE MEMBRANE TRANSPORT PROTEIN

The methods illustrated below to obtain a cDNA sequence encoding mammalian vesicle membrane transport protein, the gene for the transport protein and the transport protein, are merely for purposes of illustration and are typical of those that might be used. However, other procedures may also be employed, as is understood in the art.

Chinese hamster ovary (CHO) cells lack several neuronal features known to affect susceptibility to $MPP^+$, such as excitability, catecholamine uptake activity and receptors for neurotrophic factors. However, at high density, CHO cells have an extremely steep dose-response curve to $MPP^+$, with virtually complete inhibition of protein synthesis after exposure to over 100 μM for only 2–3 days. At low density, CHO cells show a similar threshold of sensitivity, but simply stop growing until detachment from the plate days to weeks later. Although they lack a plasma membrane catecholamine transport protein and so have less sensitivity to $MPP^+$ than dopaminergic neurons in vivo, CHO cells still show greater sensitivity to $MPP^+$ than PC12 cells. Thus, CHO cells were first used herein as a simplified system in which to identify the properties that confer resistance to this form of toxicity in PC12 cells.

Cloning of Coding Sequences for Mammalian Vesicle Membrane Transport Protein

The entire cDNA sequence encoding rat chromaffin granule transport protein has been cloned and expressed in Chinese Hamster Ovary (CHO) cells as set forth in Examples 1 and 2, infra.

A PC12 cDNA library in a plasmid expression vector was transferred into relatively resistant $MPP^+$-sensitive CHO fibroblasts using a modified calcium phosphate transfection procedure as described by Chen and Okayama, *Mol. Cell. Biol.* 7:2745–2752 (1987)). Selection of the stable transformants in 1 mM MPP$^+$ yielded a clone extremely resistant to MPP$^+$. Plasmids integrated into the host cell DNA were rescued to identify the cDNA sequences responsible for conferring resistance to MPP$^+$. Retransfection of the pooled rescued DNA produced secondary transformants exhibiting resistance to MPP$^+$. This resistance was found to be reversible with reserpine.

The entire cDNA sequence encoding human brain-specific synaptic vesicle amine transporter protein (hSVAT) has also been cloned as set forth in Example 4, infra. A human midbrain cDNA library in λ bacteriophage gt10 was screened with rat rSVAT cDNA, positive plaques were picked, and bacteriophage DNA prepared from the plaques. To identify clones containing full-length cDNA, oligonucleotide primers from the 5'- and 3'- ends of rSVAT were used to amplify the bacteriophage DNA by the polymerase chain reaction (PCR) procedure. A single clone yielded a PCR product of the appropriate size, and the insert from this clone was subcloned for sequence analysis.

Genomic DNA in a λ bacteriophage vector library was also used to isolate substantially purified DNA comprising the gene for hSVAT, including the introns originally present in the genome. The genomic library was screened with radioactively labeled rCGAT cDNA. Positive plaques were picked after autoradiography and purified through additional rounds of screening. To distinguish between phage clones encoding CGAT and SVAT, a radiolabeled Nco I fragment containing a divergent loop between the first and second predicted transmembrane domains was used to probe a Southern blot of DNA from the various phage clones. A 1.3 kb Eco RI fragment from one phage isolate was subcloned. Sequence analysis of double-stranded plasmid DNA of this subclone showed an exon with a predicted amino acid sequence highly related to a large loop in rSVAT and unrelated to the same region of rCGAT.

Expression of Mammalian Vesicle Membrane Transport Protein

With the complete nucleotide sequence encoding mammalian vesicle membrane transport protein provided herein, the sequence can be expressed in a variety of systems. In Example 1, infra, the cDNA encoding the protein is expressed in CHO cells. To effect functional expression, the plasmid expression vector CDM8 (Aruffo and Seed, *Proc. Natl. Acad. Sci. USA* 84:8573–8577 (1987), provided by Drs. Aruffo and Seed (Harvard University, Boston, Mass.) was used. Alternatively, other suitable expression vectors such as retroviral vectors can be used. The vector containing the cDNA was then transfected into CHO cells, and stable transformants were selected in MPP$^+$. Expression of the vesicle membrane transport protein in CHO cells resulted in cells resistant to the toxin MPP+ whose resistance was reversed in the presence of reserpine. In addition, cells resistant to the toxin showed a particulate cytoplasmic stain for loaded dopamine that was also reversed by reserpine.

Standard Methods

The techniques for sequencing, cloning and expressing DNA sequences encoding the amino acid sequences corresponding to the vesicle membrane transport protein, e.g. polymerase chain reaction (PCR), synthesis of oligonucleotides, probing a cDNA library, transforming cells, constructing vectors, extracting messenger RNA, preparing cDNA libraries, and the like are well-established in the art, and most practitioners are familiar with the standard resource materials for specific conditions and procedures. However, the following paragraphs are provided for convenience and notation of modifications where necessary, and may serve as a guideline.

Sequencing

Isolated cDNA encoding the vesicle membrane transport protein was analyzed by subcloning the insert from the cDNA clone into a plasmid such as pBluescript™ (Stratagene, San Diego, Calif.) and using the dideoxy method (Sanger et al., *Proc. Natl. Acad. Sci. USA* 74:5463–5467 (1977)) using single-stranded templates and Sequenase (U.S. Biochemical (USB), Cleveland, Ohio). The DNA sequence and predicted protein sequence was then compared to established databanks such as Gen Bank, EMBO or SwissProt using standard as well as profile-based methods as described by Gribskov et al., *Proc. Natl. Acad. Sci. USA* 84:4355–4358 (1987) and Devereux et al., *Nucl. Acids Res.* 12:387–395 (1984).

Hosts and Control Sequences

Both procaryotic and eucaryotic systems can be used to express the vesicle membrane transport protein; however eucaryotic hosts are preferred.

Eucaryotic microbes, such as yeast, can be used as hosts for mass production of the vesicle membrane transport protein. Laboratory strains of *Saccharomyces cerevisiae*, Baker's yeast, are most used although a number of other strains are commonly available. Vectors employing, for example, the 2μ origin of replication of Broach, *Meth. Enz.* 101:307 (1983), or other yeast compatible origins of replications (see, for example, Stinchcomb et al., *Nature* 282:39 (1979)); Tschempe et al., *Gene* 10:157 (1980); and Clarke et al., *Meth. Enz.* 101:300 (1983)) can be used.

Control sequences for yeast vectors include promoters for the synthesis of glycolytic enzymes (Hess et al., *J. Adv. Enzyme Reg.* 7:149 (1968); Holland et al., *Biochemistry* 17:4900 (1978)). Additional promoters known in the art include the promoter for 3-phosphoglycerate kinase (Hitzeman et al., *J. Biol. Chem.* 255:2073 (1980)), and those for other glycolytic enzymes.

Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization.

It is also believed terminator sequences are desirable at the 3' end of the coding sequences. Such terminators are found in the 3' untranslated region following the coding sequences in yeast-derived genes.

Alternatively, the genes encoding the mammalian vesicle membrane transport protein are expressed in eucaryotic host cell cultures derived from multicellular organisms. (See, for example, *Tissue Cultures*, Academic Press, Cruz and Patterson, Eds. (1973)). These systems have the additional advantage of the ability to splice out introns and thus can be used directly to express genomic fragments.

Useful host cell lines include amphibian oocytes such as Xenopus oocytes, COS cells, VERO and HeLa cells, Chinese hamster ovary (CHO) cells and insect cells such as SF9 cells. Expression vectors for such cells ordinarily include promoters and control sequences compatible with mammalian cells such as, for example, the commonly used early and late promoters from baculovirus, vaccinia virus, Simian Virus 40 (SV40) (Fiers et al., *Nature* 273:113 (1973)), or other viral promoters such as those derived from polyoma, Adenovirus 2, bovine papilloma virus, or avian sarcoma viruses. The controllable promoter, hMTII (Karin et al., *Nature* 299:797–802 (1982)) may also be used.

General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in non-coding DNA regions. Origins of replication can be obtained, if needed, from viral sources. However, integration into the chromosome is a common mechanism for DNA replication in eucaryotes.

If procaryotic systems are used, an intronless coding sequence should be used, along with suitable control sequences. The cDNA of mammalian vesicle membrane transport protein can be excised using suitable restriction enzymes and ligated into procaryotic vectors along with suitable control sequences for such expression.

Procaryotes most frequently are represented by various strains of *E. coli*; however, other microbial strains may also be used. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* 198:1056 (1977)) and the tryptophan (trp) promoter system (Goeddel et al., *Nucleic Acids Res.* 8:4057 (1980)) and the lambda derived $P_L$ promoter and N-gene ribosome binding site (Shimatake et al., *Nature* 292:128 (1981)).

Transformations

Depending on the host cell used, transformation is done using standard techniques appropriate to such cells. The treatment employing calcium chloride, as described by Cohen, *Proc. Natl. Acad. Sci. USA* (1972) 69:2110 (1972) or the $CaCl_2$ method described in Maniatis, et al., *Molecular Cloning: A Laboratory Manual*, Cold Spring Harbor Press, Sambrook et al., 2nd edition, (1989)) can be used for procaryotes or other cells which contain substantial cell wall barriers. For mammalian cells without such cell walls, the calcium phosphate precipitation method of Graham and van der Eb, *Virology* 52:546 (1978), optionally as modified by Wigler et al., *Cell* 16:777–785 (1979), or by Chen and Okayama, supra, can be used. Transformations into yeast can be carried out according to the method of Van Solingen et al., *J Bact.* 130:946 (1977), or of Hsiao et al., *Proc. Natl. Acad. Sci. USA* 76:3829 (1979).

Other representative transfection methods include viral transfection, DEAE-dextran mediated transfection techniques, lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Cloning

The cDNA sequences encoding the rSVAT and rCGAT protein were obtained from an oligo-dT-primed PC12 cDNA library.

Alternatively, the cDNA sequences encoding mammalian vesicle membrane transport protein are obtained from a cDNA library prepared from mRNA isolated from cells expressing the vesicle membrane protein in various organs such as the brain, according to procedures described in *Molecular Cloning: A Laboratory Manual*, Cold Spring Harbor, second edition, Sambrook et al., eds., (1989). The cDNA insert from the successful clone, excised with a restriction enzyme such as Eco RI, is then used as a probe of the original cDNA library to obtain the additional clones containing inserts encoding other regions of the vesicle membrane protein, that, together with this probe, span the nucleotides containing the complete protein coding sequence of the protein.

An additional procedure for obtaining cDNA sequences encoding the vesicle membrane transport protein is PCR. PCR is used to amplify sequences from a pooled cDNA library of reverse-transcribed RNA, using oligonucleotide primers based on the transporter sequences already known.

cDNA Library Production

Double-stranded cDNA encoding vesicle membrane transport protein is synthesized and prepared for insertion into a plasmid vector such as Bluescript® or Lambda ZAP® (Stratagene, San Diego, Calif.) or a vector from Clontech, Palo Alto, Calif., using standard procedures (see *Molecular Cloning: A Laboratory Manual*, Cold Spring Harbor, Sambrook et al., eds. second edition (1989)).

Library Screening

The selected cDNA library is screened using reduced stringency conditions as described by Ausubel et al., in Current Protocols in Molecular Biology, Greene Publishing and Wiley-Interscience, New York (1990) or using methods described in *Molecular Cloning: A Laboratory Manual*, Cold Spring Harbor, Sambrook et al., eds., second edition (1989), or using a plaque hybridization procedure with a fragment of the cDNA coding for rat adrenal vesicle membrane transport protein.

Plaque hybridization is typically carried out as follows. Host bacteria such as *E. coli* C600 Hfl or LE 392 (Stratagene) are grown overnight at 30° C. in 1% casein hydrolysate, 0.5% NaCl, 0.5% yeast extract, 0.1% casamino acids, 0.2% $MgSO_4$ (NZYCM) medium (*Molecular Cloning: A Laboratory Manual*, supra), gently pelleted and resuspended in one half the original volume of 10 mM $MgSO_4$. After titration, an amount of the phage library containing approximately 50,000 plaque forming units (pfu) is added to 300 µl of the host bacteria, incubated at 37° C. for 15 minutes and plated onto NZYCM agar with 10 ml NZYCM top agarose. A total of a million plaques distributed on 20 fifteen cm plates are screened. After the plaques have grown to 1 mm, the plates are chilled at 4° C. for at least two hours, and then overlaid with duplicate nylon filters, followed by denaturation of the filters in 0.5M NaOH/1.5M NaCl for five minutes and neutralization in 0.5M Tris, pH 7.4/1.5M NaCl for five minutes. The filters are then dried in air, baked at 80° C. for two hours, washed in 5× SSC/0.5% SDS at 68° C. for several hours, and prehybridized in 0.5M $NaPO_4$, pH 7.2/1% BSA/1 mM EDTA/7% SDS/100 µg/ml denatured salmon sperm DNA for more than 4 hours.

Using the rat chromaffin granule amine transport cDNA described herein labeled by random priming as a probe, high stringency hybridization is carried out in the same solution at 68° C., and the temperature is reduced to 50°–60° C. for lower stringency hybridization. After hybridization for 16–24 hours, the filters are washed first in 40 mM $NaPO_4$, pH 7.2/0.5% BSA/5% SDS/1 mM EDTA twice for one hour each, then in 40 mM $NaPO_4$, pH 7.2/1% BSA/1 mM EDTA for one hour each, both at the same temperature as the hybridization (Boulton et al., *Cell* 65:663–675 (1991)). The filters will then be exposed to film with an enhancing screen at −70° C. for one day to one week.

Positive signals are then aligned to the plates, and the corresponding positive phage is purified in subsequent rounds of screening, using the same conditions as in the primary screen. Purified phage clones are then used to prepare phage DNA for subcloning into a plasmid vector for sequence analysis. The various independent clones are also analyzed in terms of tissue distribution, using Northern blots and in situ hybridization using standard methods, as well as in terms of function, using expression in a heterologous eucaryotic expression system such as CHO cells.

In order to isolate the vesicle membrane transport cDNA from mammalian brain cells, for example rat brain, a random-primed, rat brainstem cDNA library in lambda gt10 (Clontech) was screened using the rat cDNA encoding the rat membrane transport protein described herein. In order to obtain the transport cDNA from human cells, a human cDNA library was also screened using a rat cDNA probe.

RNA Preparation

RNA preparation is as follows. The samples used for preparation of RNA are immediately frozen in liquid nitrogen and then stored until use, up to one week at −80° C. The RNA is prepared by CsCl centrifugation (Ausubel et al., supra, incorporated by reference herein) using a modified homogenization buffer (Chirgwin et al., Biochem. 18:5294–5299 (1979)). Poly($A^+$)RNA is selected by oligo (dT) chromatography (Aviv and Leder, Proc. Natl. Acad. Sci. USA 69:1408–1412 (1972)). RNA samples are stored at −80° C.

Northern Blots

Analysis of gene expression and tissue distribution can be accomplished using Northern blots containing mRNA from a range of rat tissues and cDNA encoding the rat adrenal chromaffin granule transport protein as described, for example, in Sambrook et al., supra, vol. 1, pp. 7.37–7.52, using radiolabeled cDNA. In this procedure, the mRNA is typically transferred to a nylon membrane or to nitrocellulose. The hybridized radiolabeled cDNA is typically detected using autoradiography.

Vector Construction

Construction of suitable vectors containing the desired coding and control sequences employs standard ligation and restriction techniques which are well understood in the art (Young et al., Nature 316:450–452 (1988)).

Site specific DNA cleavage is performed by treating with the suitable restriction enzyme, such as Eco RI, (or enzymes) under conditions which are generally understood in the art, and the particulars of which are specified by the manufacturer of these commercially available restriction enzymes. See, e.g., New England Biolabs, Product Catalog. In general, about 1 μg of phage DNA sequence is cleaved by one unit of enzyme in about 20 μl of buffer solution; in the examples herein, typically, an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, and can be followed by ether extraction and the nucleic acid recovered from aqueous fractions by precipitation with ethanol.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of $Na^+$ and $Mg^{++}$ using about 1 unit of BAP or CIP per μg of vector at 60° C. or 37° C., respectively, for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Ligations are performed in 15–50 μl volumes under the following standard conditions and temperatures: 20 mM Tris-HCl, pH 7.5, 10 mM $MgCl_2$, 10 mM DTT, 33 μg/ml BSA, 10 mM to 50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

Verification of Construction

Correct ligations for vector construction are confirmed according to the procedures of Young et al., Nature, 316:450–452 (1988).

Isolation of Gene Encoding Mammalian Vesicle Membrane Transport Protein

The cDNA of the vesicle membrane transport protein obtained as described above is then used as a probe of a genomic mammalian library to obtain clones containing the complete gene coding sequence of mammalian vesicle membrane transport protein. cDNA probes are constructed from the sequence encoding the chromaffin granule amine transport protein (CGAT) or the synaptic vesicle amine transport protein (SVAT) and used to probe genomic libraries from various mammalian tissues using standard hybridization methods to isolate sequences encoding vesicle membrane transport proteins from other mammalian tissues. Alternatively, sets of synthetic oligonucleotides encoding the protein are used to probe a genomic library. Successful hybridizing clones are sequenced, and those containing the correct nucleotide sequence for the protein are obtained.

Expression

The vesicle membrane protein can be expressed in a variety of systems as set forth below. The cDNA can be excised by suitable restriction enzymes and ligated into procaryotic or eucaryotic expression vectors for such expression.

II. MAMMALIAN VESICLE MEMBRANE TRANSPORT PROTEINS

An aspect of the invention is mammalian vesicle membrane transport proteins purified or isolated from either cells in which the proteins occur naturally or from chimeric cells expressing the protein in a recoverable quantity. Small quantities of such proteins, such as those produced by chimeric cells, can be used to generate protein-specific antibodies for immunoaffinity purification of the protein from cells in which the protein occurs naturally.

When produced from chimeric cells, the mammalian vesicle membrane transport protein can be produced either as a mature protein or as a fusion protein, or can be produced along with a signal sequence in cells capable of processing this sequence for secretion. It can be advantageous to obtain secretion of the protein as this minimizes the difficulties in purification. Cultured mammalian cells are able to cleave and process heterologous mammalian proteins containing signal sequences and to secrete them into the medium (McCormick et al., Mol. Cell. Biol. 4:166 (1984)). If secreted, the purification process is simplified, because relatively few proteins are secreted into the medium, and the majority of the secreted protein will, therefore, already be the vesicle membrane transport protein. However, it is also known in the art to purify the protein from membranes of cells in which it is produced in mature or fully processed form.

In one embodiment described below in Example 2, gene transfer was used to express the $MPP^+$ toxicity suppression activity of a vesicle membrane amine transport protein in non-neural cells. This led to the isolation of a cDNA clone that encodes a rat adrenal-specific transport protein, designated herein as chromaffin granule amine transport protein (CGAT protein). The sequence of the cDNA (SEQ ID NO: 1) and the predicted amino acid sequence of the protein encoded by the cDNA (SEQ ID NO: 2) are given in FIG. 1, below. The amino acid sequence of the CGAT protein predicts that its three-dimensional structure has 12 transmembrane domains. The CGAT protein has limited homology to a class of bacterial drug resistance transport proteins.

In another embodiment, as discussed below in Example 3, a probe specific for the DNA encoding CGAT protein was used to screen a bacteriophage λgt10 rat brainstem cDNA library. Sequencing of the resulting clones resulted in the determination of the nucleotide sequence and protein sequence of the brainstem protein. This protein is designated herein as synaptic vesicle amine transport protein (SVAT protein). The DNA sequence (SEQ ID NO: 3) and corresponding amino acid sequence (SEQ ID NO: 4) for SVAT protein are shown in FIG. 2.

There is substantial homology between the nucleotide and amino acid sequences for CGAT and SVAT proteins, as shown in FIG. 4. In particular, the majority of the amino acid residues of the 12 transmembrane domains are either identical or are closely related by conservative amino acid substitutions. In addition, analysis of the amino acid sequence predicted from the human SVAT cDNA yields 92.5% identity and 96.5% homology to rSVAT proteins. Most of the divergence occurs in the large lumenal loop between the first two transmembrane domains, but the human and rat SVAT sequences still show considerable homology in this region.

Accordingly, within the scope of the invention are functional equivalents of CGAT protein or SVAT protein having membrane transport activity. These functional equivalents include, but are not limited to, proteins related to the proteins of FIGS. 1, 2, or 3 (SEQ ID NO: 2, 4, & 13) by one or more conservative amino acid substitutions substantially preserving the structure of the transmembrane domains of the protein. It is a well-established principle of protein chemistry that certain amino acid substitutions, entitled "conservative" amino acid substitutions, can frequently be made in a protein without altering either the conformation or the function of the protein. Such substitutions include, but are not limited to, substituting any of isoleucine (I), valine (V), and leucine (L) for any other of these amino acids, aspartic acid (D) for glutamic acid (E) and vice versa; asparagine (N) for glutamine (Q) and vice versa; and serine (S) for threonine (T) and vice versa. Other substitutions can also be considered conservative depending on the environment of the particular amino acid in the three-dimensional structure of the protein in question. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its positive charge and the differing pK's of these two basic amino acid residues are not significant. Cysteine (C) can frequently be replaced by serine when cysteine's capacity to form disulfide bonds is either undesirable or unneeded. Still other changes can be considered "conservative" in particular environments when the three-dimensional structure of the protein is taken into account.

Also considered to be within the scope of the present invention are proteins encoded by the nucleic acid sequences discussed in Section III, below. These nucleic acid sequences include cDNA sequences and genomic DNA sequences.

III. NUCLEIC ACID SEQUENCES

Another aspect of the present invention is nucleic acid sequences coding for a vesicle membrane transport protein as described above. These nucleic acid sequences include: (1) cDNA sequences and (2) genomic DNA sequences.

A. cDNA Sequences

The cDNA sequences coding for vesicle membrane transport proteins according to the present invention comprise substantially pure cDNA encoding the amino acid sequence of FIGS. 1, 2, or 3 (SEQ ID NO: 1, 3, & 12). This cDNA is substantially free of cDNA that does not encode the amino acid sequence of FIGS. 1, 2, or 3 (SEQ ID NO: 1, 3, & 12). The cDNA can have the sequence disclosed in FIGS. 1, 2, or 3 (SEQ ID NO: 1, 3, & 12), or can be related thereto by the degeneracy of the genetic code. The cDNA can be obtained by reverse transcription or chemical nucleotide synthesis.

B. Genomic DNA Sequences

Another aspect of the invention is substantially purified genomic DNA whose exons encode mammalian vesicle membrane transport protein. Such DNA differs from cDNA by possessing intervening non-coding regions or introns. In view of the differences between the adrenal-specific (CGAT) and brain-specific (SVAT) proteins, it is likely that these two subtypes are encoded by different, albeit related, genes, although applicant does not intend to be bound by this theory.

One method of obtaining at least one such gene comprises hybridizing the cDNA described above as a probe to obtain the genomic DNA in the form of DNA hybridizing specifically with the cDNA. Depending on the stringency of the hybridization process, a single cDNA probe can be used to isolate one or more genes for the transport protein. Accordingly, substantially purified genomic DNA coding for a protein that has vesicular amine transport activity and having at least about 60% homology in its exons with at least one of the rat CGAT cDNA or the rat SVAT cDNA is within the scope of the invention, as is a protein thus encoded. This category of genomic DNA includes at least one human gene, as shown in Example 4, below. This human gene has at least about 70% homology in one of its exons with a portion of the cDNA sequence of FIG. 2 extending from about base 220 to about base 540 (FIG. 5) (SEQ ID NO: 5). In fact, this gene corresponds to SVAT, because it includes an exon with a predicted amino acid sequence highly related to the amino acid sequence of the large lumenal loop in rSVAT and unrelated to the same region of rCGAT.

In a preferred embodiment described herein, gene transfer was used to express the MPP$^+$ toxicity suppression activity of a vesicle membrane amine transport protein in non-neural cells. The gene transferred was a cDNA clone that encodes rat chromaffin granule amine transport protein. The clone was isolated using gene transfer followed by selection in MPP$^+$. The cDNA sequence encodes a novel protein with twelve transmembrane domains and homology to a class of bacterial drug resistance transport proteins.

IV. USE OF TRANSPORT PROTEINS AND NUCLEIC ACID SEQUENCES

The rat adrenal chromaffin granule amine transport cDNA of the invention obtained as described herein can be used to isolate the cDNAs or genes encoding human vesicle membrane transport proteins, such as the chromaffin granule amine transport protein, by screening the appropriate human cDNA or genomic library as described above, and to isolate additional cDNAs or genes encoding vesicle membrane transport proteins from other mammalian tissues using the procedures also set forth above. The chromaffin granule vesicle transport protein is expected to exhibit substantial homology to vesicle transport proteins from other mammalian tissues.

The sequence described herein, combined with the observed homology to the bacterial drug resistance transporters, can be used to design oligonucleotide primers to amplify reverse transcribed cDNA library or other nucleic acids using standard techniques of the polymerase chain reaction. These amplified sequences can then be used to obtain the remainder of the protein coding regions of the cDNAs or genes by screening the appropriate libraries by standard techniques.

The sequences, incorporated in appropriate vectors, can be used to transform suitable host cells for expression of the mammalian vesicle membrane transport proteins. Preferably, to obtain optimum levels of expression, transformants are selected in $MPP^+$ to obtain cells expressing the transport protein in a quantity sufficient to render the cells resistant to $MPP^+$, or are selected by screening with an antibody specifically binding the transport protein so that a host cell producing a quantity of the transport protein sufficient to react detectably with the transport protein is selected.

A method of producing a mammalian vesicle membrane transport protein according to the present invention can comprise:

(1) culturing a host cell according to the present invention transformed with an appropriate expression vector;

(2) using the cultured host cell to express the transport protein; and (3) purifying the protein.

The step of using the cultured host cell to express the transport protein can involve altering the culture conditions of the cultured host cell, such as by adding an inducer of an inducible control element to which the gene for the transport protein is operatively linked in the expression vector. The nature of the inducer depends on the particular inducible control element used.

The expressed protein can be purified by conventional methods, such as ion-exchange chromatography, gel filtration chromatography, reverse phase high pressure liquid chromatography, electrofocusing, chromatofocusing, and/or immunoaffinity chromatography, using any readily ascertainable property, such as transport activity.

The mammalian vesicle membrane transport protein, when expressed in functional form in host cells such as CHO cells, can be used to screen compounds, e.g. toxins in addition to $MPP^+$, to identify those that when sequestered within intracellular vesicles of various cell types result in cell survival, i.e., whether cytotoxicity of the reagent is reduced by sequestration of the reagent in intracellular vesicles. This may lead to identification of compounds implicated in death of various cell types involved in different diseases. The protein may also be used to screen for compounds that inhibit transport of substances into vesicles, for example to inhibit the transport of norepinephrine or epinephrine, amine transmitters that regulate heart rate and blood pressure. By using transporters expressed in different locations, e.g., from adrenal and brain tissues, it can be possible to screen for compounds having specificity for one transport protein but not the other. Thus, a compound can be obtained that inhibits the transport protein from adrenal tissue, but not the transport protein from brain tissue and so provide a way to reduce blood pressure without causing lethargy or depression. Reserpine, like other antihypertensive medications, produces lethargy and depression. By identifying a compound that inhibits amine transport in the adrenal gland but not the brain, it may be possible to eliminate this side effect. The recombinant protein can be used to screen for such compounds. In addition, the vesicle membrane transport protein can also be used to screen for compounds that inhibit central nervous system function but not adrenal transport. These compounds might be very useful as tranquilizers, anxiolytic or anti-psychotic drugs. This screening process is facilitated by the use of tissue-specific subtypes of the mammalian vesicle membrane transport protein, such as the adrenal-specific CGAT protein and the brain-specific SVAT protein.

This screening process is not limited to the determination of cell survival. It can be carried out by contacting cells containing a nucleotide sequence encoding the transport protein with a compound suspected of selectively inhibiting or activating the activity of a vesicle membrane transport protein, and then determining the activity of the transport protein within the cells contacted with the compound to determine whether the compound selectively inhibits or activates the activity of the transport protein.

This screening process can be performed by qualitative or quantitative assays of membrane transport, or, alternatively, by binding assays to determine the affinity of the compound for the protein. Such binding assays can be performed by: (1) incubating a substantially purified preparation of mammalian vesicle membrane transport protein with a compound suspected of being an inhibitor; and (2) comparing the binding by the transport protein to an amine normally bound by the transport protein of the preparation in the presence and absence of the compound to determine whether the compound has inhibitory activity.

One preferred version of a qualitative assay, described in Example 1, below, detects uptake and cellular compartmentalization of loaded dopamine in cells grown on polylysine-coated glass coverslips. After incubation of the cells in glyoxylic acid-$MgCl_2$, uptake of the dopamine is detected by fluorescence viewed through a fluorescence microscope.

One preferred version of a quantitative assay, described in Example 1 below, measures the uptake of labeled dopamine by the membrane fraction resulting from cellular homogenates. The quantitative assay is performed on transfected cells that are selected in $MPP^+$ or have been screened with antibodies so that cells with a higher level of expression of the transporter are used. The quantity of label bound is measured after filtration of the assay mixture. Preferably, the label is a radioactive label. By varying the dopamine concentration, the $K_m$ for dopamine transport can be determined. This can be done by standard graphic kinetic techniques such as the Lineweaver-Burke plot. The $K_i$ for inhibition of dopamine uptake by serotonin, epinephrine, or norepinephrine can also be determined by similar kinetic techniques.

The mammalian vesicle membrane transport protein and nucleotide coding sequences have various diagnostic and therapeutic applications. For example, the ability of the protein to sequester the toxin $MPP^+$ implicated in Parkinson's disease provides the ability to protect cells from this toxin. In addition, the transport protein coding sequences, when transfected into a suitable host cell, can be used to screen for drugs that affect the functional expression of the protein. Such drugs may either upregulate or downregulate the expression of the transport protein or induce post-translational modifications that alter activity of the expressed protein.

DNA or RNA sequences coding for hCGAT or hSVAT can be used as probes to detect chromosomal abnormalities. As shown below in Example 5, the gene for human CGAT occurs on chromosome 8 at 8p21.3. At least one report exists of a disease, hereditary spherocytosis, due to a deletion that may include the gene for CGAT. Probes corresponding to this gene may be useful in detection of this chromosomal abnormality by hybridization, and polymerase chain reaction (PCR) amplification procedures or other nucleic acid amplification procedures involving initiation from delimited primers can be used to determine the extent of the deletion.

Similarly, the human gene for SVAT is located on chromosome 10 at 10q25, and deletions from a point surrounding this region to end of the chromosome have appeared in the literature and the phenotype associated with this deletion includes dysmorphic features and severe metal retardation. Accordingly, diagnostic techniques involving hybridization with labeled probes can be used to detect these conditions as well. A suitable procedure can comprise:

(1) hybridization of a labeled single-stranded nucleic acid sequence of sufficient length to hybridize specifically to chromosomal DNA and whose sequence is derived from the human SVAT gene to human chromosomal DNA; and (2) detecting the hybridized labeled nucleic acid sequence to determine the presence or absence of an abnormality in human chromosome 10.

The labeled single-stranded nucleic acid sequence is preferably from the large lumenal loop to allow the method to distinguish between hSVAT and hCGAT. Typically, the labeled nucleic acid sequence is at least about 10 nucleotides in length, more typically at least 50 nucleotides, preferably at least 100 nucleotides.

In addition, the vesicle membrane transport coding sequences can be used to enhance sequestration of $MPP^+$ into mammalian cells to treat Parkinson's Disease. To carry out such treatment, the gene or cDNA encoding the vesicle transport protein must be placed in cells located in the midbrain so as to cause expression of the gene in vivo. For example, an effective number of cells in the midbrain are transfected with vectors carrying the gene encoding the vesicle transport protein, such as recombinant herpes simplex virus vectors (see Dobson et al., Neuron 5:353–360 (1990); Geller and Freese, Proc. Natl. Acad. Sci. USA 87:1149–1153 (1990) and Preston et al., PCT Application Ser. No. WO 91/02788, "Herpes Simplex Virus Type I Mutant"), to produce sufficient amounts of the vesicle membrane transport protein in vivo to permit the cells of the midbrain to sequester toxins such as $MPP^+$.

Alternatively, the nucleotide sequence encoding the mammalian vesicle transport protein of the invention can be operably linked to control sequences that enhance or decrease the expression of the protein. This construct can then be transferred or transfected via an appropriate vector, for example a retroviral vector into suitable host cells, for example primary fibroblasts or neural cells, which are then introduced into a mammal to express and/or secrete the vesicle membrane protein (see Gage et al., U.S. Pat. No. 5,082,670 (1992)). For example, control sequences that increase the expression of the vesicle transport protein of the invention can be used to enhance sequestration of toxic molecules into cells to confer resistance in a mammalian subject to the toxic molecules.

Vesicle membrane transport proteins that transport other compounds, such as acetylcholine and various neurotoxins including glutamate, can be used to modulate the uptake and storage of such compounds to combat the deleterious effects of accumulations of these compounds.

An important use of the vesicle membrane transport proteins of the invention, particularly those that transport amines, is the treatment of psychiatric diseases such as affective disorders including bipolar disease and Schizophrenia and other diseases where there is an imbalance of amines, including norepinephrine, dopamine and serotonin. For treatment, the activity of the vesicle membrane transport protein is increased, for example by modifying expression of the protein using vectors carrying enhancers of the gene or cDNA encoding the vesicle membrane transport protein to transfect cells in the brain.

In addition, the mammalian vesicle membrane transport proteins can be used to diagnose susceptibility to various diseases resulting from imbalances of compounds in vivo. Thus, the protein or nucleotide sequences coding for it can be used to identify subjects having reduced activity of the protein or reduced levels of RNA encoding the protein. This is accomplished using known polymorphisms in the nucleotide sequence that confer alterations in activity. The genes encoding the vesicle membrane transport proteins may prove useful to determine whether the genes are linked to various psychiatric diseases, and this information can then be used to design drugs that increase or decrease transport of compounds across the vesicle membranes to treat the diseases resulting from imbalances in these compounds.

In addition, selection of cells carrying mutations in the gene or cDNA encoding the vesicle membrane transport protein in the presence of $MPP^+$ and reserpine or tetrabenazine or other compounds can be used to define the site of action of these other compounds. For example, the cDNA encoding the transport protein can be altered by standard procedures such as site-directed mutagenesis or saturation mutagenesis, for example using mutagenic bacteria (Fowler et al., Mol. Gen. Genet. 133:179–191 (1991); Silhavy et al., "Experiments with Gene Fusions," Cold Spring Harbor Press, 1984, pp. 75–78). The mutagenized cDNA is used to transfect cells for selection in the presence of $MPP^+$ and a compound capable of inhibiting the transport protein. These procedures will provide information about the site of action of drugs on the transport protein. This information, in turn, can be used to design compounds with desired properties such as greater activity or improved therapeutic abilities. In addition, variant vesicle transport proteins can be obtained that are not inhibited by drugs such as reserpine and tetrabenazine.

V. PHARMACEUTICAL COMPOSITIONS AND ANTIBODIES

Another aspect of the invention is antibodies specific for the vesicle membrane transport proteins and pharmaceutical compositions incorporating the proteins.

The vesicle membrane transport protein can be used to prepare antibodies, including polyclonal antibodies that bind to purified or recombinant vesicle transport protein or peptides. These antibodies can be used to purify the vesicle membrane transport protein in larger quantities. For example, the transport protein can be purified by fixing the antibody to a solid support and reacting the antibody fixed to the solid support with a sample containing the transport protein to bind the transport protein to the antibody. Alternatively, the antibody can be labeled with a detectable label, reacting the antibody labeled with the detectable label with a sample containing transport protein to bind the transport protein to the antibody, thereby forming an antigen-antibody complex, and separating the antigen-antibody complex from other proteins present in the sample. In either case, the protein can then be dissociated from the antibody by standard techniques, such as high salt, change of pH, or low concentrations of chaotropic agents.

The purified protein can then be used, for example, to screen for compounds capable of blocking binding of substances such as reserpine to the purified transport protein (Stern-Bach et al., *J. Biol. Chem.* 265:3961–3966 (1990)). Such screening can be used to identify compounds that bind to the plasma membrane transport protein but not to the vesicle membrane transport protein for selectively blocking the binding to one or the other transport protein.

Similarly, tissue-specific subtypes of purified vesicle membrane transport protein can be used to identify tissue-specific inhibitors by determining the degree of inhibition caused by the inhibitor for a first tissue-specific subtype and for a second tissue-specific subtype and comparing the degree of inhibition. This procedure can be used, for example, to identify an inhibitor of the adrenal transport protein that does not affect the brain transport protein. This should assist in the development of new blood pressure medications that do not exhibit side effects on the central nervous system, or, conversely, new tranquilizers, anxiolytics, or antidepressants that do not exhibit systemic side effects.

Monoclonal antibodies reactive with vesicle membrane transport protein can be produced by hybridomas prepared using known procedures, such as those introduced by Kohler and Milstein (see Kohler and Milstein, *Nature*, 256:495–97 (1975)), and modifications thereof, to regulate cellular interactions.

These techniques involve the use of an animal which is primed to produce a particular antibody. The animal can be primed by injection of an immunogen (e.g. the vesicle membrane transport protein) to elicit the desired immune response, i.e. production of antibodies from the primed animal. A primed animal is also one which is expressing a disease. Lymphocytes derived from the lymph nodes, spleens or peripheral blood of primed, diseased animals can be used to search for a particular antibody. The lymphocyte chromosomes encoding desired immunoglobulins are immortalized by fusing the lymphocytes with myeloma cells, generally in the presence of a fusing agent such as polyethylene glycol (PEG). Any of a number of myeloma cell lines can be used as a fusion partner according to standard techniques; for example, the P3-NS1/1-Ag4-1, P3-x63-Ag8.653, Sp2/0-Ag14, or HL1-653 myeloma lines. These myeloma lines are available from the ATCC, Rockville, Md.

The resulting cells, which include the desired hybridomas, are then grown in a selective medium such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of the desired specificity, e.g. by immunoassay techniques using the vesicle membrane transport protein that has been used for immunization. Positive clones can then be subcloned under limiting dilution conditions, and the monoclonal antibody produced can be isolated.

Various conventional methods can be used for isolation and purification of the monoclonal antibodies so as to obtain them free from other proteins and contaminants. Commonly used methods for purifying monoclonal antibodies include ammonium sulfate precipitation, ion exchange chromatography, and affinity chromatography (see Zola et al., in *Monoclonal Hybridoma Antibodies: Techniques and Applications*, Hurell (ed.) pp. 51–52 (CRC Press, 1982)). Hybridomas produced according to these methods can be propagated in vitro or in vivo (in ascites fluid) using techniques known in the art (see generally Fink et al., *Prog. Clin. Pathol.*, 9:121-33 (1984), FIG. 6-1 at p. 123).

Generally, the individual cell line can be propagated in vitro, for example, in laboratory culture vessels, and the culture medium containing high concentrations of a single specific monoclonal antibody can be harvested by decantation, filtration, or centrifugation.

In addition, fragments of these antibodies containing the active binding region reactive with the vesicle membrane transport protein, such as Fab, $F(ab')_2$ and FV fragments can be produced. Such fragments can be produced using techniques well established in the art (see e.g. Rousseaux et al., in *Methods Enzymol.*, 121:663–69, Academic Press (1986)).

Polyclonal antibodies can be produced, for example polyclonal peptide antibodies as described by Hirayama et al., in *Am. J. Phsiol.* 261:C296-C304 (1991). Briefly, peptides are synthesized, e.g. as described by Kent and Clark-Lewis, in *Synthetic Peptides in Biology and Medicine*, Amsterdam, Elsevier, p. 29–57 (1985), and are purified using reverse-phase high-performance liquid chromatography on a preparative $C_8$ column in a gradient of 17.5–32.5% acetonitrile with 0.1% trifluoroacetic acid (TFA). The purity of the product is verified by isocratic elution on a $C_{18}$ column in 25.5% acetonitrile and 0.1% TFA and by mass spectroscopy before lyophilization. Immunization can be accomplished by coupling to keyhole limpet hemocyanin. Polyclonal antibodies are then raised in rabbits following standard procedures using the peptides as immunogen. These procedures permit the production of antibodies that bind to defined regions of the vesicle membrane transport protein amino acid sequence, using peptides or portions of peptides of the vesicle membrane protein as immunogen.

The compositions and antibodies of the invention are administered in vivo into a mammal using conventional modes of administration which include, but are not limited to intravenous, oral, subcutaneous, intraperitoneal, and intralymphatic. The compositions can be administered for gene therapy.

The pharmaceutical compositions of the invention comprising inhibitors of amine transport, or antibodies, can be in a variety of dosage forms which include, but are not limited to, solid, semi-solid and liquid dosage forms such as tablets, pills, powders, liquid solutions or suspensions, suppositories, polymeric microcapsules or microvesicles, liposomes, and injectable or infusible solutions. The preferred form depends upon the mode of administration and the therapeutic application.

Conventional pharmaceutically acceptable carriers for the compositions may include those known in the art such as serum proteins including human serum albumin, buffer substances such phosphates, water or salts or electrolytes.

The most effective mode of administration and dosage regimen for the compositions of this invention depends upon the patient's health and response to treatment and the judgment of the treating physician. Accordingly, the dosages of the compositions should be titrated to the individual patient.

The following examples are presented to illustrate the present invention and to assist one of ordinary skill in the art in making and using the invention. The examples are not intended in any way to otherwise limit the scope of the invention.

EXAMPLE 1

Suppression of MPP$^+$ Toxicity by Gene Transfer of Vesicle Membrane Amine Transport Protein This example describes the isolation of a cDNA clone extremely resistant to the toxin MPP$^+$ using rat pheochromocytoma PC12 cells as a source of a cDNA expression library transfected into MPP$^+$-sensitive CHO fibroblasts.

Cell culture

All cells were maintained in a humidified incubator at 37° C. in 5% $CO_2$. PC12 cells were grown in Dulbecco's modified Eagle's medium containing 10% horse serum and 5% fetal calf serum, CHO cells in Ham's F12 medium with 10% fetal calf serum. $MPP^+$ (Research Biochemicals, Inc., Natick, Mass.) was dissolved in Ham's F12 medium without serum at a concentration of 20 mM, passed through a 0.22 μm filter, then added at the appropriate concentration to the medium without serum. Rotenone (Sigma Chemical Co., St. Louis, Mo.), oligomycin (Sigma) and dopamine (Sigma) were similarly dissolved in medium, filtered and added to the cultures. Reserpine (Sigma) was dissolved in dimethylformamide before adding to the medium.

RNA preparation and cDNA library construction

PC12 cells were grown to relatively high density, mechanically dislodged from the plate, sedimented in a clinical centrifuge and homogenized in guanidinium isothiocyanate as described by Chirgwin et al., *Biochem.* 18:5294–5299 (1979). Briefly, a guanidinium thiocyanate stock was prepared by mixing guanidinium thiocyanate with sodium N-lauroylsarcosine, sodium citrate, 2-mercaptoethanol and antifoam A (Sigma, St. Louis, Mo.). The ionized water was added and the pH adjusted to 7.0 with 1.0N NaOH. The samples were homogenized into guanidinium thiocyanate stock solution in a homogenizer for 30–60 seconds at full speed. The homogenates were centrifuged for 10 min. at 8,000 rpm at 10° C. to sediment particulate material. The supernatants were decanted into a flask and mixed with 0.025 volume (relative to the original volume of homogenizing buffer) of 1M acetic acid to lower the pH from 7 to 5 and 0.75 volume of absolute ethanol. The flask was capped, shaken thoroughly, and placed at −20° C. overnight to precipitate nucleic acid. The material was sedimented by centrifugation for 10 min. at −10° C. and 6,000 rpm. The tubes were drained of supernatant and any material that did not form a firm pellet. The pellet was then resuspended by vigorous shaking in 0.5 volume (relative to the original volume of homogenization buffer) of buffered guanidinium chloride stock solution (pH 7.0, buffered with 0.025 volume of 1M sodium citrate, pH 7.0, 5 mM in dithiothreitol or dithioerythritol). If necessary, the samples were briefly warmed in a 68° C. water bath to ensure complete dispersion. RNA was reprecipitated by adding (relative to the amount of guanidinium chloride) 0.025 volume of 1M acetic acid and 0.5 volume of ethanol. The solution was kept for at least 3 hr. at −20° C. and centrifuged as before. A final reprecipitation from guanidinium chloride was performed in the same way, with a further halving of the total volume. This reprecipitated material was centrifuged for only 5 min at 6,000 rpm. The final pellets were dispersed in ethanol at room temperature, triturated if necessary to extract excess guanidinium chloride, and again centrifuged for 5 min at 6,000 rpm. Ethanol was removed from the pellet by a stream of nitrogen, and the RNA was dissolved by vigorous shaking in sterile water. The solution was centrifuged for 10 min at 13,000 rpm and 10° C. to sediment insoluble material. The supernatants containing the RNA were decanted and saved, while the insoluble material was reextracted twice with the sterile water, followed by centrifugation for 10 min at 13,000 rpm and 10° C. The combined aqueous solution was mixed with 0.1 volume of 2M potassium acetate, pH 5, and precipitated with ethanol. After centrifugation, the pellets were washed with ethanol, dried with nitrogen, and dissolved in sterile water. The RNA was separated by centrifugation trough cesium chloride, resuspended in 10 mM Tris/1 mM EDTA containing 0.1% SDS, extracted with phenol, then chloroform, and precipitated twice in ethanol. Oligo-dT cellulose was used to isolate the $polyA^+$ fraction of RNA as described by Aviv and Leder, *Proc. Natl. Acad. Sci. USA* 69:1408–1412 (1972). Briefly, the RNA was dissolved in application buffer containing 0.01M Tris-HCl, pH 7.5, 0.5M KCl, and was applied to an oligo-dT cellulose column previously washed with application buffer. The non-absorbed material was eluted by continued washing with the application buffer. The material retained by the column was eluted in two steps with buffers of reduced ionic strength. The first elution buffer contained 0.01M Tris-HCl, pH 7.5, 0.1M KCl, the second 0.01M Tris-HCl, pH 7.5. The material eluted by the two elution steps with buffers of reduced ionic strength was combined and precipitated by the addition of potassium acetate and two volumes of ethanol. The first strand of cDNA was synthesized from 5 μg $polyA^+$ RNA using oligo-dT as primer and avian myeloblastosis virus reverse transcriptase. The second strand was synthesized with RNase H and *E. coli* DNA polymerase and, after rendering the ends of the double-stranded cDNA blunt with T4 DNA polymerase, BstXI linkers were added as described by Gubler and Hoffman, *Gene* 25:263–269 (1983); and Aruffo and Seed, *Proc. Natl. Acad. Sci. USA* 84:8573–8577 (1987). Briefly, blunt-end ligation was performed on phosphorylated oligonucleotide linkers in a reaction mixture containing 6 mM Tris-HCl, pH 7.5, 6 mM $MgCl_2$, 5 mM NaCl, 0.35 mg/ml bovine serum albumin, 7 mM 2-mercaptoethanol, 0.1 mM ATP, 2 mM dithiothreitol, 1 mM spermidine, and 400 units of T4 DNA ligase in a 0.3-ml reaction mixture at 15° C. overnight. Free linker and cDNA fragments less than 0.8–1.5 kb in length were removed by electrophoresis through 5% acrylamide under nondenaturing conditions, and the larger size-selected material electroeluted and precipitated twice with ethanol. The cDNA was then ligated into the CDM8 vector from which the BstXI stuffer fragment has been removed, and transformed into bacteria by electroporation as described by Dower et al., *Nucl. Acids. Res.* 16:6127–6145 (1988). Briefly, the expediential decay pulses were generated by a Gene Pulser apparatus (Bio-Rad Laboratories, Richmond, Calif.) set at 3 or 25 μF and from 0.2 to 2.5 kV. The output of the pulse generator was directed to a pulse controller unit (Bio-Rad) containing a high power, 20-ohm resistor in series with the sample, and a selection of resistors of 100 to 1,000 ohms in parallel with the sample. The effective resistance placed in parallel with the electrodes is much lower than that of the sample, and determines the time constant of the pulse (for example, 200 ohms with a 25 μF capacitor gives a 5 msec time constant. Electrode gaps of either 0.15 cm with a special "minielectrode", or 0.2 cm with a small gap Potter-type cuvette (Bio-Rad) were used. These electrode configurations provided field strengths of up to 16.7 kV/cm and 12.5 kV/cm. The concentrated cells were thawed at room temperature and placed on ice. The cells (40 μl) were transferred to a cold, 1.5 ml polypropylene tube; 1 to 2 μl of DNA solution (in a low ionic strength medium such as TE) was added to give a final concentration of from 10 pg/ml to 7.5 μg/ml, and this suspension was mixed vigorously by flicking the tube. The cell-DNA mixture was placed between the chilled electrodes, the electrode assembly or cuvette placed in the safety chamber, and the appropriate pulse applied. Following the pulse, the cells were immediately removed from the electrodes and mixed in 25 to 50 volumes of outgrowth medium (2% Bacto-Tryptone, 0.5% Bacto-Yeast extract, 10 mM NaCl, 2.5 mM KCl, 10 mM $MgCl_2$, 10 mM $MgSO_4$, 20 mM glucose) in a 17×100 mm polypropylene tube. The samples were incubated for 1 hr at 37° C. At the end of the expression period, the cells were diluted and plated on agar containing the appropriate antibiotic to screen for transformants.

Gene transfer

Library plasmid DNA was prepared by alkaline lysis, sedimented twice through CsCl, then extracted with phenol and precipitated twice in ethanol. With the RSV-neo plasmid as a selectable marker for stable transformation, the DNA was reprecipitated under sterile conditions and transfected using a modified calcium-phosphate procedure as described by Chen and Okayama, *Mol. Cell. Biol.* 7:2745–2752 (1987) with the buffer BES (N,N-bis-(2-hydroxyethyl)-2-aminoethanesulfonic acid) at pH 6.95 and 3% $CO_2$ and the plasmid expression vector CDM8 (Aruffo and Seed, supra, supplied by Drs. Aruffo and Seed, Harvard University, Boston, Mass.).

MTT assay

Figures 6A, 6B:
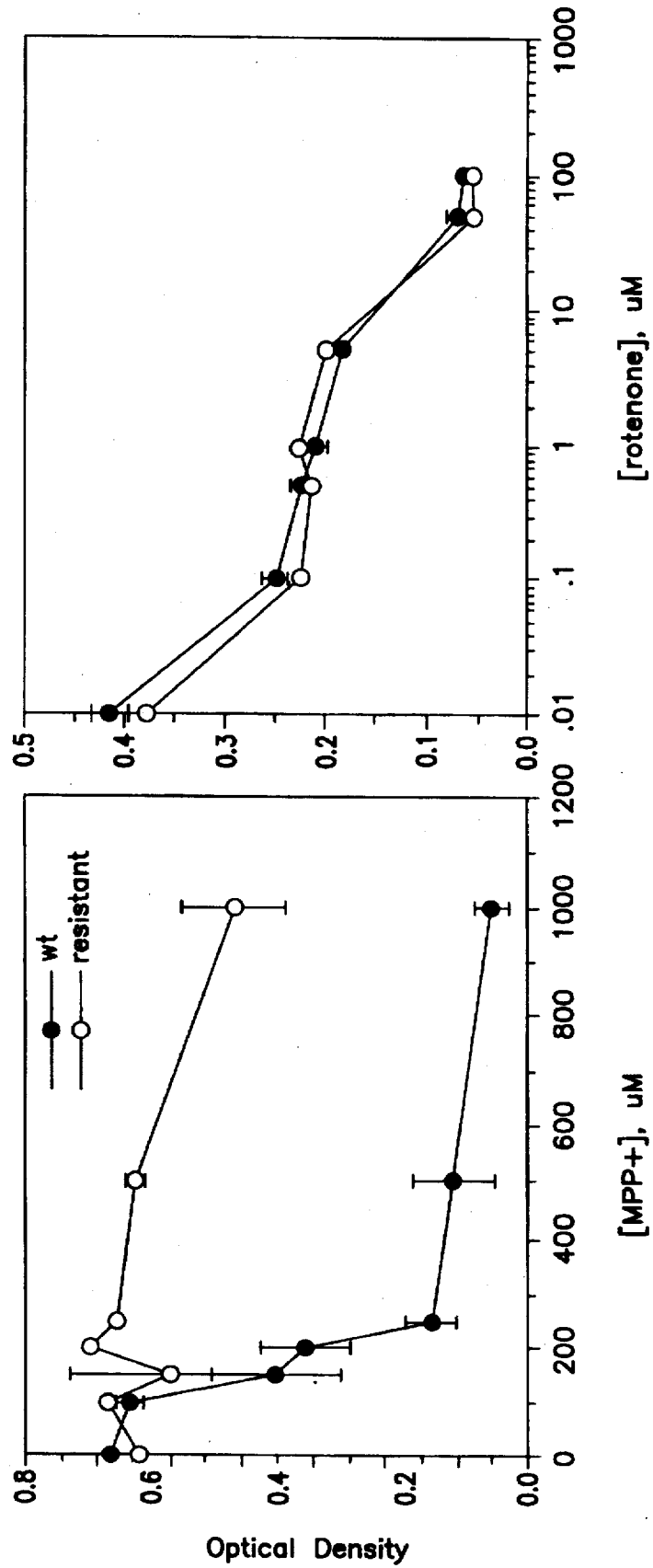
FIG. 6a and 6b are graphs showing the differential susceptibility to the respiratory complex I inhibitors $MPP^+$ and rotenone, in wild-type and $MPP^+$-resistant CHO cells as described in Example 1, infra (FIG. 6a: $MPP^+$.

Differential susceptibility to the respiratory complex I inhibitors $MPP^+$ and rotenone was shown by measuring toxicity by measuring general cell dehydrogenase activity with reduction of a tetrazolium dye (MTT) in a spectrophotometric plate assay as described by Hansen et al., *J. Immunol. Methods* 119:203–210 (1989). Briefly, a stock solution of MTT (3,(4,5-dimethylthiazol-2-yl)2,5-diphenyltetrazolium bromide) was dissolved at a concentration of 5 mg/ml in sterile phosphate buffered saline at room temperature. To each well was added 25 µl of the stock solution. After two hours of incubation at 37° C., 100 µl of extraction buffer (20% w/v of SDS in a solution of 50% each dimethylformamide and demineralized water with the pH adjusted to 4.7 with acetic acid and HCl). After an overnight incubation at 37° C., the optical densities at 570 nm were measured using a multiscanner, employing the extraction buffer as the blank. This assay was carried out in triplicate on 96-well plates (NUNC, Denmark). $MPP^+$ and rotenone at the concentrations indicated in FIG. 6a and 6b, respectively, was added to wild-type and $MPP^+$-resistant CHO cells at approximately 50% confluence, and toxicity was assayed after 2–3 days by measuring general cell dehydrogenase activity with the reduction of the tetrazolium dye MTT (3,(4,5-dimethylthiazol-2-yl)2,5-diphenyl-tetrazolium bromide). After addition of the dye at a final concentration of 1 mg/ml, the cells were incubated for two hours at 37° C. and the formazan product was solubilized in 10% sodium dodecyl sulfate (SDS). The plates were maintained at 37° C. for an additional twenty hours and the optical density was determined in an ELISA plate reader at a test wavelength of 570 nm, a reference wavelength of 630 nm and a calibration setting of 1.99. All determinations were performed in triplicate and expressed as the mean, with the error bars representing standard deviation (FIG. 6a and 6b).

Oxygen consumption

The cells were trypsinized, resuspended in Krebs-Ringer buffer, counted in a hemocytometer and respiration was determined on different numbers of cells in a glass chamber with a Clark oxygen electrode as described by Denton and Howard, supra.

Catecholamine uptake

Uptake of radiolabelled $MPP^+$ was determined by distributing cells into a 24-well plate (NUNC) in the presence of serum, washing them the next day in serum-free medium and then incubating them in serum-free medium containing [$^3$H]-$MPP^+$ (NEN, Wilmington, Del.). At the end of incubation for varying intervals up to several days, the cells were washed three times in serum-free medium without radiolabelled drug, solubilized in 1% SDS and an aliquot counted in Ecolite (ICN Pharmaceuticals, Irvine, Calif.). All measurements were determined in duplicate or triplicate and normalized to protein content.

A method was devised to measure intracellular compartmentalization of exogenously loaded catecholamines.

Uptake and cellular compartmentalization of loaded dopamine were performed by growing cells on poly-lysine-coated glass coverslips. After cell attachment, the medium was replaced with standard medium plus serum that contains 0.5–1.0 mM dopamine and incubated for an additional 12–24 hours. The cells were then washed three times in 0.1M sodium phosphate, pH 7.4, and incubated at 4° C. in 2% glyoxylic acid/0.5 mg% $MgCl_2$, pH 4.9–5.0 for three minutes as described by de la Torre, *J. Neurosci. Meth.* 3:1–5 (1980). Briefly, excess solution is wiped off the bottom and edges of the slide using absorbent paper, taking care not to touch the section. The coverslips were then drained thoroughly, dried in air at 45° C. heated to 80° C. for five minutes, inverted over mineral oil on glass slides and examined under fluorescence using the appropriate filters as described by Knigge et al., *Brain Res.* 120:393–405 (1977). Briefly, the preparations were infiltrated with warm immersion oil and examined in a Leitz MPV2 microspectrofluorometer equipped with Schoffel excitation and emission grating monochromators, photomultipliers, and ratio computing circuitry. Cells were scanned with either monochromatic light (370 nm) or narrow band excitation (S405, BG3) light for the purpose of identifying fluorescence within cells. Ploem illumination was used in combination with a X 63 or X 100 oil immersion objective. The high concentration of dopamine used to load the cells enters through nonspecific low affinity systems, and thus bypasses the need for high affinity uptake. Microscopic examination of the loaded cells using the induced fluorescence technique permits direct visualization of the cellular distribution of exogenously supplied dopamine.

A quantitative assay to measure dopamine uptake was performed as follows. $Mpp^{res}$ transformants and wild type CHO cells were homogenized at 0.01 mm clearance in cold 0.32M sucrose-10 mM HEPES-KOH, pH 7.4 (SH) containing 5 mM MgEGTA, 1 µg/ml leupeptin and 0.2 mM diisopropylfluorophosphate, and the cell debris removed by centrifugation at 3500×for 5 minutes. An aliquot containing 100 to 150 µg protein from this low speed supernatant was then added to 200 µl SH containing 4 mM KCl, 4 mM $MgSO_4$, 5 mM ATP, 44 nM [$^3$H]dopamine, and, if inhibition of uptake is to be measured, the inhibitory compound. Incubation was performed at 29° C. for the time period indicated (from 2 minutes to 30 minutes). The assay was terminated by dilution in cold assay buffer followed by filtration through 0.2 µm Supor™ 200 membranes (Gelman, Ann Arbor, Mich.) and the bound radioactivity was measured. The cells used for the quantitative assay are selected in $MPP^+$ or screened with antibody to ensure that they express the transporter at high levels, as it is difficult to measure activity in this assay at low levels of transporter expression.

To determine whether the transfer of DNA sequences from PC12 cells into CHO cells could be used to generate stable CHO transformants resistant to $MPP^+$, it was first necessary to determine the spontaneous rate of resistance under different culture conditions. Untransfected CHO cells selected in 500 µM $MPP^+$ showed different patterns of toxicity depending on cell density. At high density (more than 75% confluence), all of the cells died within 24 hours, with no possibility for subsequent growth. At low density (less than 25% confluence), the cells stopped growing, gradually acquiring refractile cytoplasmic inclusions, swelling and eventually detaching from the plate after several weeks. Selection of one million CHO cells at intermediate density (25-50% confluence) in 500 µM MPP$^+$ gave rise to 5-10 small colonies after one month. However, these cells contained particulate inclusions characteristic of MPP$^+$ toxicity, and grew very slowly even when maintained at low density. At moderate density, the cells degenerated further and detached from the plate. Thus, untransfected CHO cells were shown to acquire little resistance to 500 µM MPP$^+$ during selection for over two months.

Using the above methods, the PC12 cDNA library constructed in the plasmid expression vector CDM8 was transfected into CHO cells. Using the selectable marker RSV- neo (Walker, Weizmann Institute, Israel), two hundred to 500,000 independent stable transformants were obtained after selection in the neomycin analogue G418 at 400 µg/ml effective dose. These cells were then selected at 40% confluence in 1 mM MPP$^+$. Virtually all of the cells developed toxicity within one week, and many detached from the plate by three weeks, with no evidence of healthy cells at that time. However, at four weeks, a colony of cells without refractile inclusions appeared and rapidly covered the plate. The apparently normal growth of these cells in the presence of 1 mM MPP$^+$ stands in marked contrast to all of the resistant clones obtained without transfection, which grew very slowly if at all. Using the MTT assay to measure cell toxicity as described above, a steep dose-response curve to MPP$^+$ in wild-type cells was observed and a relative lack of toxicity in the selected resistant cell clone (FIG. 6a). However, at 1 mM MPP$^+$, the resistant cells did show some toxicity, particularly when the assay was performed at higher cell density.

Because changes in cell density and presumably growth rate were observed to affect MPP$^+$ toxicity, it was important to determine whether the transfected clone's resistance arose from a change in growth rate. However, repeated determination of growth rate in the resistant clone in the absence of MPP$^+$ showed no difference from wild-type CHO cells. In the presence of MPP$^+$, the resistant clone did grow slightly more slowly than untreated wild-type cells, particularly at higher densities.

Figure 7B:
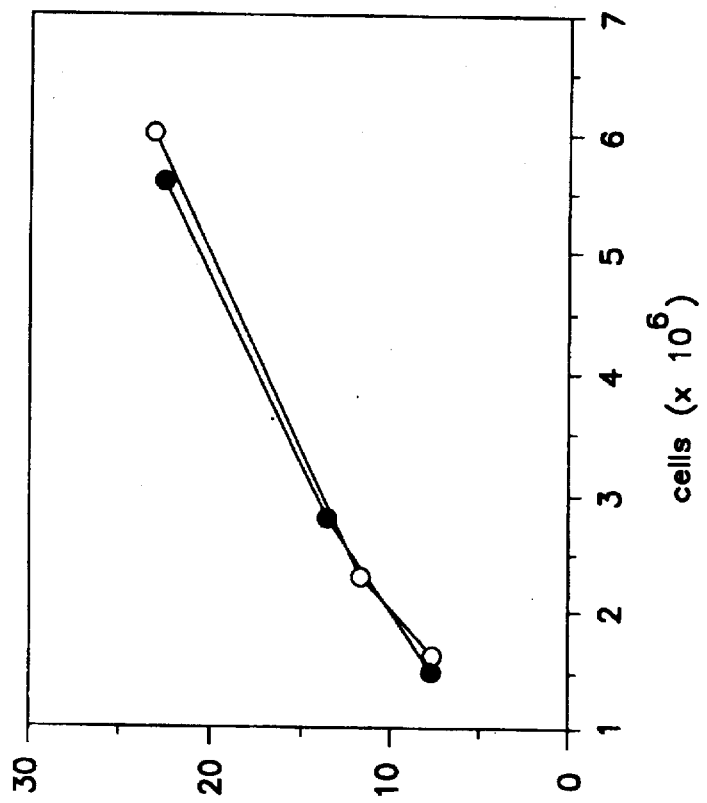
FIG. 7a and 7b are graphs showing the effects on oxygen consumption of $MPP^+$ in wild-type (FIG. 7a) and $MPP^+$-resistant (FIG. 7b) cells, as described in Example 1, infra.
Figure 7A:
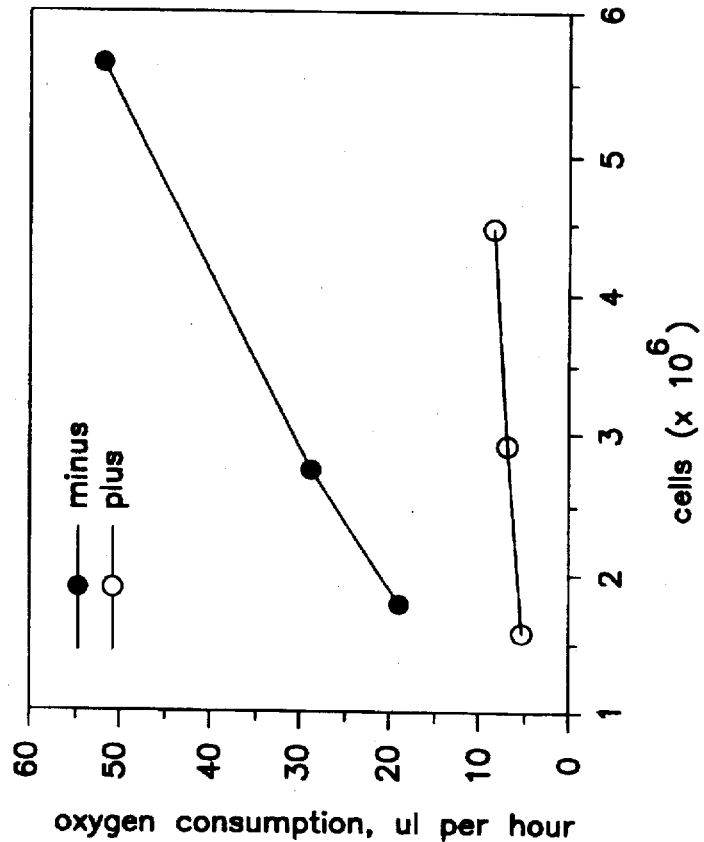
Figure 8B:
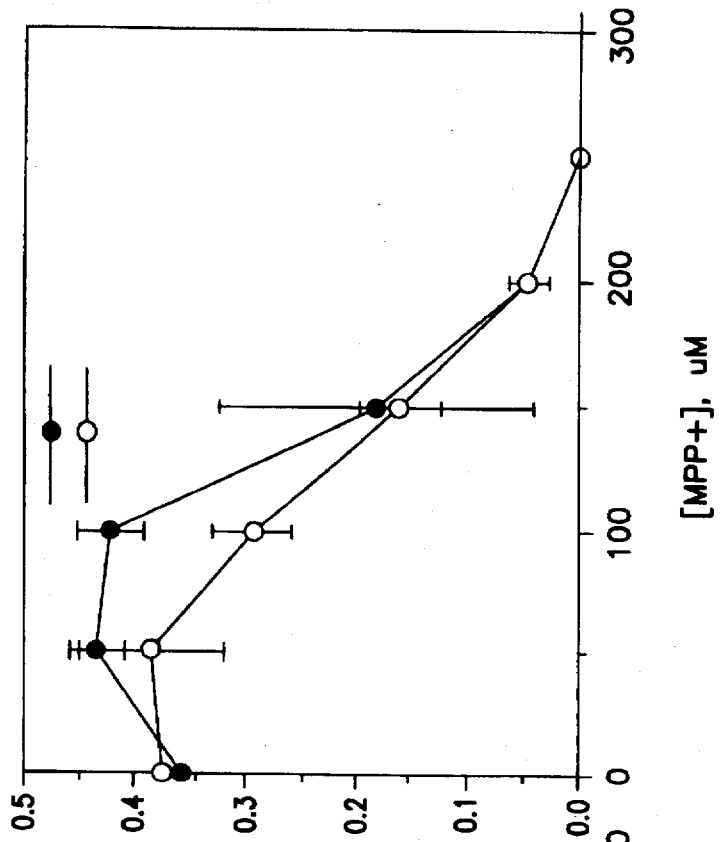
FIG. 8a and 8b are graphs showing the effects on $MPP^+$ resistance of reserpine as described in Example 1, infra (FIG. 8a: MPP+-resistant CHO cells at 25% confluence.
Figure 8A:
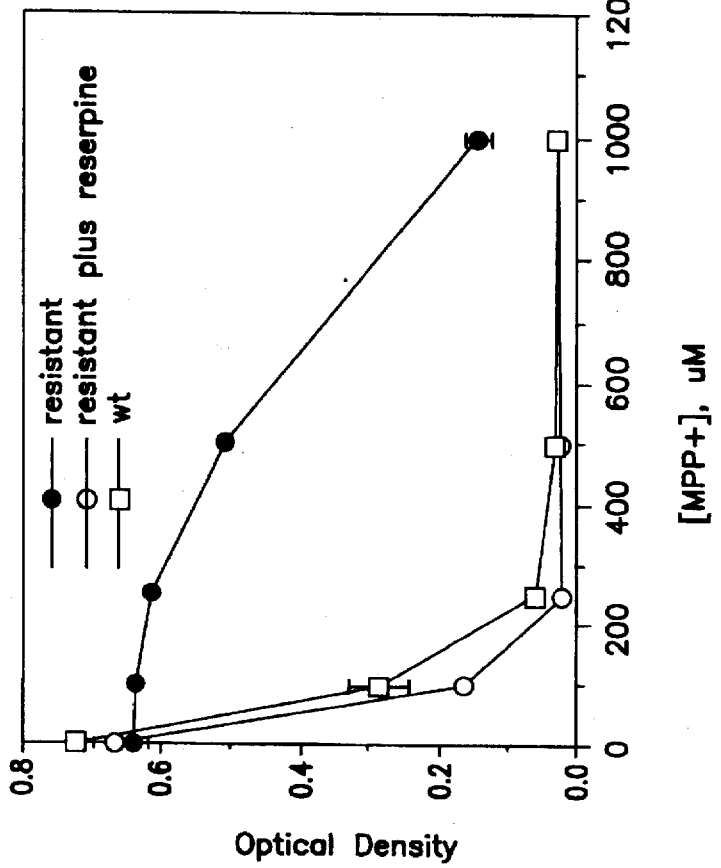

Resistance to MPP$^+$ could derive from improved ability of the cell to compensate for inhibition of respiration, such as by an increased dependence on glycolysis (Denton and Howard, *J. Neurochem.* 49:622–630 (1987); and Reinhard et al., *J. Neurochem.* 55:311–320 (1990)). To determine the role of such compensatory mechanisms, oxygen consumption was measured to examine the primary site of MPP$^+$ action in the respiratory chain. If a compensatory mechanism was responsible for resistance, MPP$^+$ would be expected to inhibit oxygen consumption in both wild-type and resistant cells. As shown in FIG. 7a, 500 µM MPP$^+$ dramatically inhibits oxygen consumption as early as 12 hours after exposure in wild-type cells. However, in the resistant transfected cells, MPP$^+$ does not detectably affect oxygen consumption (FIG. 7b). Thus, although improved ability to compensate for respiratory injury remains a possible, additional mechanism for resistance to MPP$^+$, the principal mechanism for resistance in the clone appears to reside either in the primary site of action of the drug in the respiratory chain, or in its metabolism and distribution by the cell.

To determine whether an alteration in the process of respiration was responsible for the resistance to MPP$^+$, the effects of other known respiratory inhibitors were examined. Oligomycin inhibits complex III of the respiratory chain, and demonstrated the same pattern of toxicity in wild-type and in resistant transfected CHO cells. This was consistent with the previous finding that the mechanism of resistance in these cells does not derive from an improved ability to compensate for respiratory injury. Rotenone inhibits complex I of the respiratory chain and competes with MPP$^+$ for binding to its presumed chain of action (Krueger et al., supra, and Ramsay et al., supra). Thus, if the resistance were due to a change in the site of action, the transfected cells should also show resistance to rotenone. Repeated experiments have demonstrated no substantial resistance to rotenone in the transfectant (FIG. 7b). However, rotenone is considered to have its selected effect on respiration at relatively low doses, and an additional, less specific effect at higher doses. Toxicity using the MTT assay showed a biphasic pattern in CHO cells (FIG. 6b), but in no dose range was there a clear difference of the resistant cells from wild-type. Because the primary site of drug action was unaltered by these criteria, the mechanism of resistance in the transfected cells appears specific for MPP$^+$, suggesting a role for altered drug metabolism or distribution.

Because CHO cells lack a system for the high affinity uptake of catecholamines, resistance to MPP$^+$ cannot be due to loss of this system. Although a different type of activity might be responsible for drug export, the uptake of 25 nM [$^3$H]-MPP$^+$ over one to 48 hours at 37° C. showed no difference between wild-type and resistant cells, providing no support for an active efflux mechanism. Thus, the cells show little evidence for an alteration in the primary site of drug action or for active export.

Because previous studies suggested a potential mechanism for resistance to MPP$^+$ related to changes in cellular drug distribution and that the MPP$^+$ uptake mechanism might protect against the toxin by sequestering it in the granules, and because PC12 cells express reserpine-sensitive vesicular uptake of amines, it was proposed that transfer of the reserpine-sensitive MPP$^+$ uptake activity was responsible for the resistance to MPP$^+$ toxicity observed in the CHO transfectant. Therefore, the toxicity of MPP$^+$ to transfected cells in the presence of 1 µM reserpine was examined. Dramatic reversion to wild-type CHO sensitivity was observed (FIG. 7a). To demonstrate that reserpine does not affect a mechanism present in wild-type CHO cells, the effect of reserpine on wild-type cells treated with lower concentrations of MPP$^+$ to which they are normally sensitive is shown in FIG. 7b. The only changes occurred at the top of the steepest section of the dose-response curve, which typically shows the greatest random fluctuation and standard deviation in this assay (see FIG. 6). Thus, reserpine shows very little reproducible effect on MPP$^+$ toxicity in wild-type cells. These results suggest that the transfected cell clone survived selection in MPP$^+$ because the cells express a vesicular amine uptake activity, presumably derived from PC12 cells, that effectively sequesters the toxin from its primary site of action in mitochondria.

For direct observation of whether the resistant cells expressed an intracellular amine transport activity, it was necessary to circumvent the absence of a high affinity plasma membrane transport system in the CHO transfectant. Neuronal cells that synthesize amines usually express both plasma membrane and synaptic vesicle catecholamine transport activity. Detection of specific uptake requires amines radiolabelled to high specific activity. Using either labelled MPP$^+$ or catecholamine in the 10 to 100 nM range, it is possible to detect both specific plasma membrane and vesicular uptake in neuronal cultures. However, if the cell lacks a high affinity plasma membrane transporter, catecholamines at these low concentrations will not effectively enter the cell. Thus, it was necessary to use higher concentrations of catecholamine to observe intracellular transport in the transfected CHO cells. If radiolabelled $MPP^+$ is diluted with unlabelled $MPP^+$ to obtain the concentrations required for significant low affinity uptake, the amount of radioisotope entering the cell is too low to measure reliably.

Figure 9A:
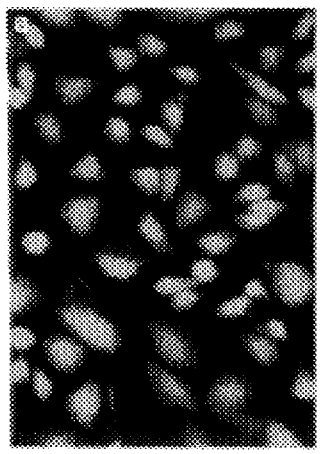
FIG. 9a–9c are photographs showing particulate staining of exogenously loaded dopamine in a $MPP^+$-resistant CHO transformant using glyoxylic acid-induced fluorescence, as described in Example 1, infra (FIG. 9a: wild-type CHO cells.
Figure 9B:
Figure 9C:
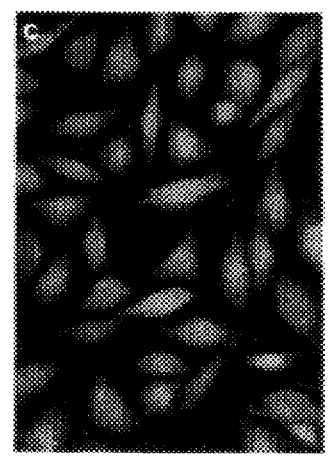

Using the method described above to measure intracellular compartmentalization of exogenously loaded catecholamines, wild-type CHO cells demonstrated a diffuse, ground-glass pattern of cytoplasmic catecholamine fluorescence (FIG. 9a). In contrast, the resistant cells showed a very different pattern, with intense accumulation of catecholamine in a perinuclear location (FIG. 9b). The cytoplasm also contained scattered punctate fluorescent stain, but less general cytoplasmic fluorescence than wild-type cells, presumably reflecting reduced access of $MPP^+$ to mitochondria and so accounting for the differences in sensitivity. To determine whether the pattern of catecholamine accumulation in the transfectant was inhibited with reserpine, the same histofluorescence assay was performed using reserpine, and reversion to the wild-type pattern of catecholamine accumulation was observed (FIG. 9c). These results confirm that the mechanism of $MPP^+$ resistance in the transfected cells involves reserpine-sensitive sequestration of the drug within an apparently distinct intracellular compartment. In contrast to the results described by Reinhard et al., *Proc. Natl. Acad. Sci. USA* 84:8160–8164 (1987) which show that reserpine can potentiate the depletion of amines and reduction in tyrosine hydroxylase by $MPP^+$, the results presented herein demonstrate that the rat adrenal chromaffin granule transport protein actually modulates $MPP^+$ toxicity to the cell, using cell death as the endpoint.

The above results demonstrate the use of gene transfer to confer substantial resistance in recipient cells to the toxin $MPP^+$. The reversal of $MPP^+$ resistance by reserpine and the intracellular accumulation of loaded dopamine indicate that resistance to the toxin arises from expression of a vesicle membrane amine transport protein. While not wishing to be bound by any theory, it is believed that this transport activity reduces the cytoplasmic level of toxin by sequestering $MPP^+$ inside an intracellular compartment, thereby decreasing the amount of drug available to enter mitochondria and inhibit respiration. This demonstration that the transport activity suffices to protect cells form $MPP^+$ toxicity implicates the transport protein as a major determinant of resistance among aminergic cell populations. Moreover, this activity confers resistance to $MPP^+$ even in a non-neuronal cell line that lacks the synaptic vesicles in which such a transporter normally functions.

The above results implicate the balance between plasma membrane and vesicular uptake of catecholamines as a crucial determinant of $MPP^+$ toxicity. Although a number of aminergic populations accumulate the toxin by high affinity plasma membrane uptake, it may be that only nigral neurons degenerate because they express lower levels of vesicular uptake. Thus, although these results identify a component of resistance to the toxin using expression in a fibroblast, its reduced activity in midbrain neurons relative to the adrenal gland (and perhaps sympathetic ganglia) may account for the selective vulnerability of nigral cells. Chromaffin granule amine content and uptake activity vastly exceed that observed in synaptic vesicles from the central nervous system (Johnson, *Physiol. Rev.* 68:232–307 (1988)), suggesting that such differential expression exists and may well account for the observed differential susceptibility to $MPP^+$.

Figure 10:
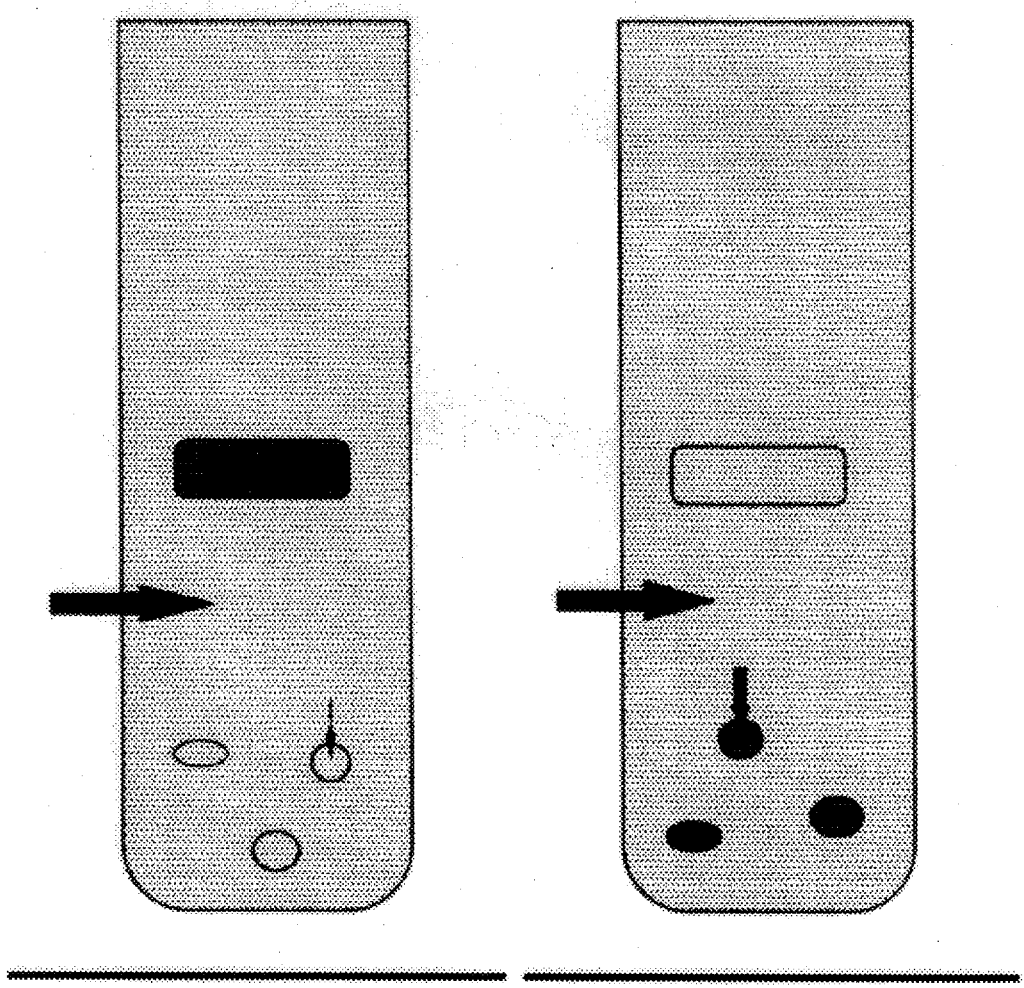
FIG. 10 is a diagrammatic depiction from above of presynaptic neurons with mitochondrion (rectangle), synaptic vesicles, equal plasma membrane uptake (large arrows) but less (left) and more (right) vesicular uptake (small arrows), as described in Example 1, infra. (The concentration of toxin or neurotransmitter in the various compartments is indicated by the intensity of shading).

Because Parkinson's disease usually spares chromaffin cells of the adrenal medulla and postganglionic sympathetic neurons, differential expression of the vesicular amine transport protein has relevance for this idiopathic disorder. Because dopamine may induce oxidative stress (Cohen, *J. Neural Transmission Suppl.* 32:229–238 (1990)), an imbalance between membrane and vesicular catecholamine transport would lead to high cytoplasmic levels of dopamine as well as $MPP^+$, and could be responsible for oxidative stress unrelated to an exogenous toxin (FIG. 10). FIG. 10 shows a presynaptic neuron above with mitochondrion, synaptic vesicles, equal plasma membrane uptake but less (left) and more (right) vesicular uptake. The concentration of toxin or neurotransmitter in the various compartments is indicated by the intensity of shading.

These results indicate the therapeutic potential for manipulation of the vesicle amine transport protein in PD. The transport protein presumably recognizes the same features of an exogenous or endogenous toxin that are recognized by the plasma membrane transporter, and which presumably account for the selective cell vulnerability observed in PD. However, in contrast to the plasma membrane transporter, increased expression of the vesicle transport protein has a protective effect. This approach to therapy has the advantage that it makes no assumptions about the exact nature of the toxin.

The above experiments demonstrate that the vesicular transport of neurotransmitter can be expressed in a cell without synaptic vesicles. Vesicular transport activity does not appear to require other specific synaptic vesicle components for functional expression. It requires only the activity of a more widely distributed vesicular $H^+$-ATPase to generate the proton gradient that drives transport. The method of loading transfected non-neuronal cells with exogenous neurotransmitter followed by direct visualization of its cellular location as described herein provides a method to detect the intracellular transport activity in the absence of a high-affinity plasma membrane transporter.

As described below, the $MPP^+$-resistant CHO transfectant provided a source for the isolation of sequences encoding a vesicle membrane protein having amine transport activity.

EXAMPLE 2

Cloning and Sequencing of Chromaffin Granule Amine Transporter Gene

This example identifies a cDNA clone that encodes the chromaffin granule amine transport protein.

Identification of cDNA clone encoding resistance to $MPP^+$

To identify the cDNA sequences responsible for conferring resistance to $MPP^+$, integrated plasmids were rescued from the primary CHO transformant obtained as described above in Example 1. A size-selected oligo-dT-primed PC12 cDNA library in the plasmid expression vector CDM8 was transfected into CHO cells, the stable transformants were selected in 1 mM $MPP^+$ and the resistance of selected cells was found to be reversible with reserpine as described above in Example 1. The primary $MPP^+$-resistant CHO transformant was amplified in culture and following cell lysis in 5M guanidinium isothiocyanate, the high molecular weight DNA prepared by repeated precipitation in isopropanol. After digestion with Not I, which cleaves the CDM8 vector once downstream of the cDNA insertion site as well as at rare eight-nucleotide recognition sites elsewhere in the genome, the DNA was religated and transformed into *E. coli* by electroporation as described by Stern-Bach et al., *J. Biol. Chem.* 265:3961–3966 (1990). Four pools of the derived plasmids containing approximately 50 colonies each were transfected into CHO cells and after two days were selected in 1 mM $MPP^+$. Four weeks later, one pool gave rise to several MPP⁺-resistant colonies, two pools gave rise to 1–2 colonies and the fourth pool and CDM8 vector gave rise to no healthy, resistant colonies. Restriction enzyme analysis of the plasmids in the pool conferring the highest frequency of resistance to MPP⁺ indicated three independent clones of 1.0, 1.3 and 2.5 kb. These plasmids were then transfected individually into CHO cells, which were again selected in 1 mM MPP⁺. After 2½ weeks, only cells transfected with the 2.5 kb cDNA (mpp$^{res}$) contained healthy CHO cells growing at a normal rate.

Figure 11:
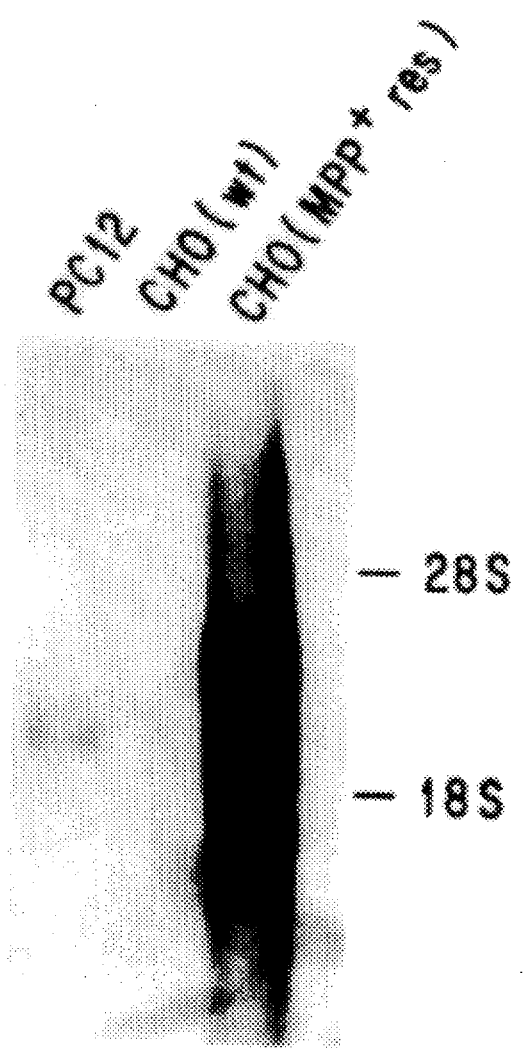
FIG. 11 is a photograph showing expression of RNA transcripts from the rescued $mpp^{res}$ sequences in PC12 cells, wild-type and $MPP^+$-resistant CHO cells, as described in Example 2, infra.

For Northern analysis, 10 μg total RNA was separated by electrophoresis through 2.2M formaldehyde/1.5% agarose, blotted to nylon (Hybond, Amersham), pre-hybridized in 50% formamide/5× SSC/5×Denhardt's solution/0.5% SDS/ 200 μg/ml salmon sperm DNA for 4 hours at 42° C., hybridized in the same solution with the mpp$^{res}$ insert labelled by random priming at 42° C. for 16 hours, washed twice in 2× SSC/0.1% SDS for 30 minutes at room temperature, in 1× SSC/0.1% SDS for 1 hour at 50° C., 0.1× SSC/0.1% SDS for 1 hour at 50° C. and submitted to autoradiography with an intensifying screen for 18 hours FIG. 11 shows the results of selection. The positions of 18S and 28S RNA are shown to the right in FIG. 11.

Dopamine-loaded fluorescence was carried out as described in Example 1. In order to examine vesicular amine transport directly in the resistant cells, cells were loaded with high concentrations of exogenous dopamine that circumvents the absence of a high affinity plasma membrane catecholamine transporter. Glyoxylic-acid-induced fluorescence was used to determine the intracellular distribution as described above in Example 1. The procedures were the same as described in Example 1 however a pure cDNA clone encoding the vesicle membrane transport protein, selected in the presence of MPP⁺, obtained as described herein, was used rather than the primary transformant.

As shown in FIG. 12, wild-type CHO cells showed diffuse cytoplasmic staining (FIG. 12a), while MPP⁺-resistant CHO cells (FIG. 12b) showed strong perinuclear and particulate cytoplasmic staining that was inhibited by 1 μM reserpine (FIG. 12c). This supports the hypothesis that vesicular amine transport confers resistance to MPP⁺.

Figure 13A:
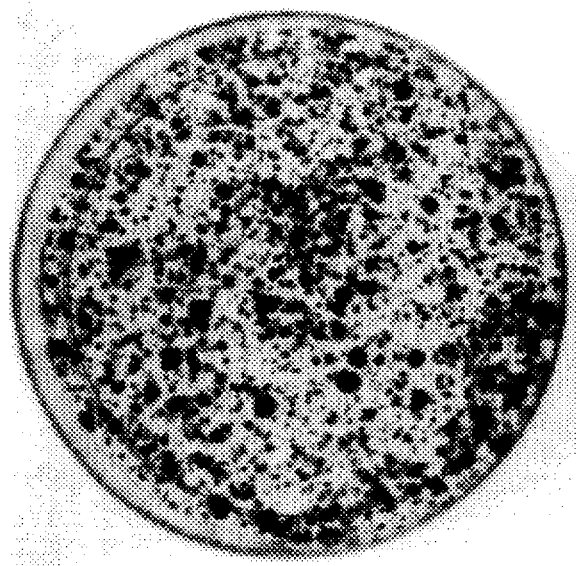
FIG. 13 is a photograph showing selection of CHO cells in $MPP^+$ after transfection with cDNA clone $mpp^{res}$ (left) and CDM8 vector alone (right), as described in Example 2, infra.
Figure 13B:
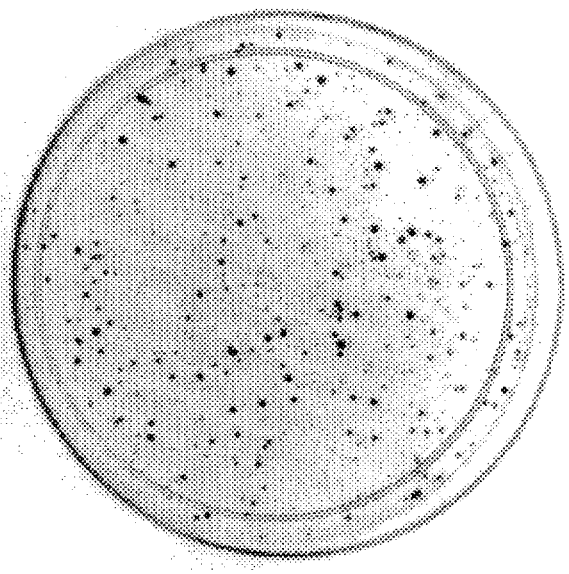

From the pools of plasmid DNA, a single clone, designated mpp$^{res}$, was identified that conferred resistance to MPP⁺ after 2–3 weeks of selection in the toxin (FIG. 13) as noted above. FIG. 13 shows selection of CHO cells after transfection with mpp$^{res}$ (left) and CDM8 vector alone (right). Only cells transfected with the mpp$^{res}$ cDNA gave rise to healthy colonies, whereas cells transfected with other rescued cDNAs and the vector alone either died and detached or remained adherent, but with the refractile cytoplasmic inclusions characteristic of MPP⁺ toxicity. The persistently low frequency and late appearance of resistant colonies suggested that an additional factor might be required to express this mechanism of resistance. However, FIG. 11 shows that whereas wild-type CHO cells express none of these sequences, the resistant cells express over twenty times more than the PC12 cells serving as the source of the cDNA library. Thus, the low frequency of resistant colonies presumably results from the extraordinarily high levels of mpp$^{res}$ expression which are required to confer drug resistance.

Figure 14A:
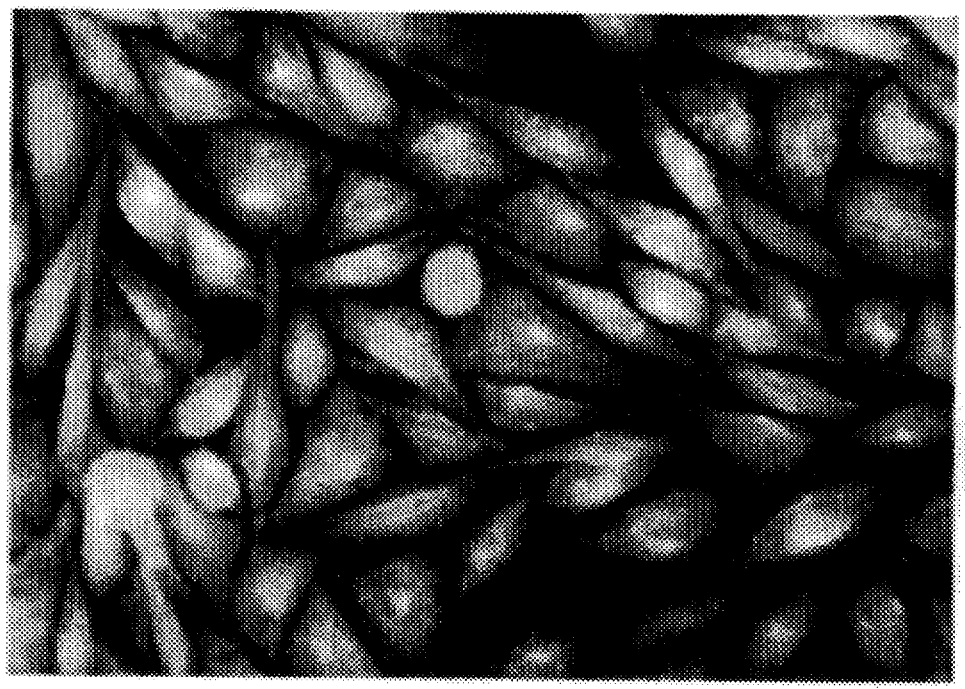
FIG. 14 is a photograph showing glyoxylic acid-induced fluorescence of $mpp^{res}$ transformants selected in the neomycin analogue G418 in the absence (top) and presence (bottom) of reserpine, as described in Example 2, infra.
Figure 14B:
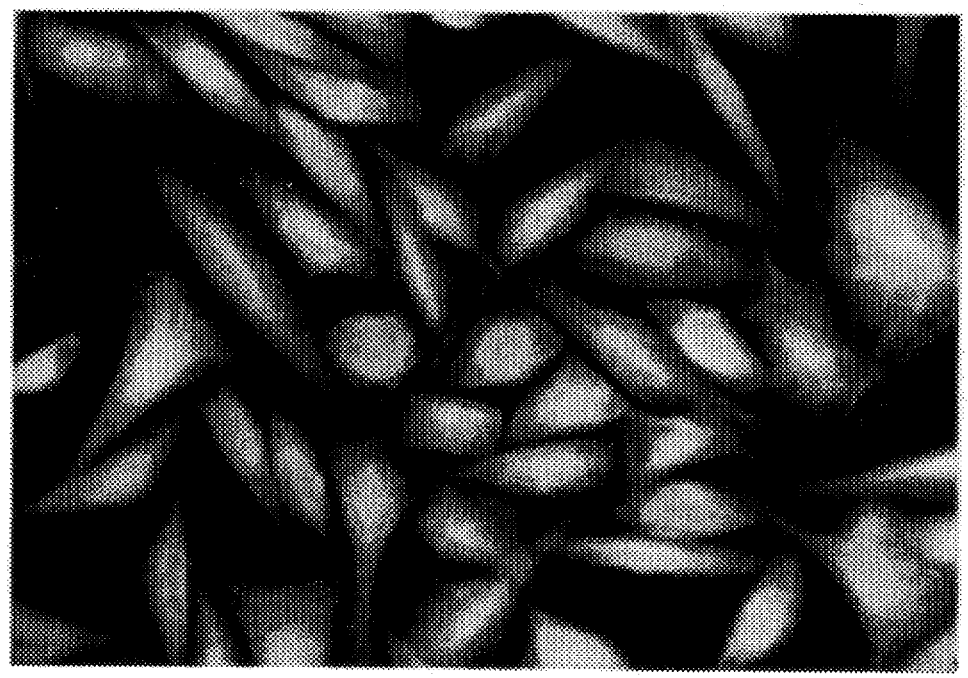

To address the possibility that selection in MPP⁺ may be required to express functional vesicular amine transport, the mpp$^{res}$ cDNA was co-transfected with the selectable marker RSV-neo. Stable transformants were first selected in the neomycin analogue G418 (400 μg/ml) effective dose for one week and then in 1 mM MPP⁺ for two weeks. At the end of selection, the residual cells were stained with 0.05% Coomassie Blue-R/10% acetic acid/50% methanol. As determined by dopamine-loaded fluorescence, selection in the neomycin analogue G418 yielded a high proportion of stable transformants that expressed easily detectable vesicular transport activity qualitatively similar to that observed after selection in MPP⁺ (FIG. 14, top). Thus, the expression of mpp$^{res}$ alone suffices to confer vesicular amine transport, even in a non-neuronal cell.

The effects of various pharmacologic agents were tested to determine whether the properties of the protein encoded by the mpp$^{res}$ cDNA corresponded with those expected for the chromaffin granule amine transport protein. PC12 dopamine uptake was determined in a 24-well plate pre-coated with poly-L-lysine. The cells were pre-incubated in Krebs-Ringer buffer containing 1 μM pargyline and the dose of the drug indicated for 15 minutes. 25 nM [³H]-dopamine was then added in the same buffer and after incubation at 37° C. for one hour, the cells were washed in cold Krebs-Ringer buffer, lysed and counted in Ecolite (ICN) as described by Greene and Rein, *Brain Res.* 129:247–263 (1978). Values were determined from three separate wells and the mean was expressed as percent of control uptake±standard deviation. The dopamine fluorescence assay was carried out as described in Example 1, with an abbreviated 12 hour period of dopamine loading to minimize drug degradation. The dose required to inhibit maximal uptake by 50%, $K_i$, was estimated from the fluorescence data using a range of concentrations for each agent. The results are shown in Table 1.

TABLE 1

| Agent | Dopamine Fluorescence | | |
|---|---|---|---|
| | [³H]-Dopamine Uptake (PC12) | (mpp$^{res}$ CHO) | $K_i$ (est) |
| — | 100 ± 5% | | |
| reserpine 1 μM | 23 ± 2 | 0 | 25 nM |
| tetrabenazine 100 μM | 45 ± 2 | ++ | 100 μM |
| verapamil 100 μM | 21 ± 1 | 0 | 50 μM |
| desipramine 1 μM | 30 ± 2 | ++++ | 500 μM |
| chloroquine 500 μM | 17 ± 1 | 0 | |
| NH₄Cl, 10 mM | 51 ± 3 | ++ | |

The ability of 50 nM reserpine to inhibit vesicular dopamine uptake completely in the fluorescence assay supports the identity of the cloned sequences as the chromaffin granule amine transport protein. Because vesicular transport is known to rely on a proton gradient, the effects of agents that disrupt vesicular acidification were also tested. As shown in Table 1, chloroquine inhibited vesicular amine uptake, but ammonium chloride inhibited uptake only partially, possibly due to expression of the transport protein in a protected compartment. Tetrabenazine and verapamil also inhibited transport, but at high concentrations that may reflect poor access in an intact cell as opposed to the chromaffin granule preparations in which transport has usually been characterized. It is also possible that the reduced sensitivity of the adrenal transporter to tetrabenazine may explain the known greater potency of that drug to deplete central rather than adrenal amine stores (Carlsson, *Hdbk. Exp. Pharmacol.* 19:529–92 (1965)). The pattern of drug response observed using the dopamine-loaded fluorescence assay in the CHO transfectant corresponded to the pattern observed using the uptake of labelled transmitter in intact PC12 cells (Table 1), indicating that the cloned cDNA conferred virtually all of the pharmacologic properties of the native vesicle amine transport protein.

Figure 15A:
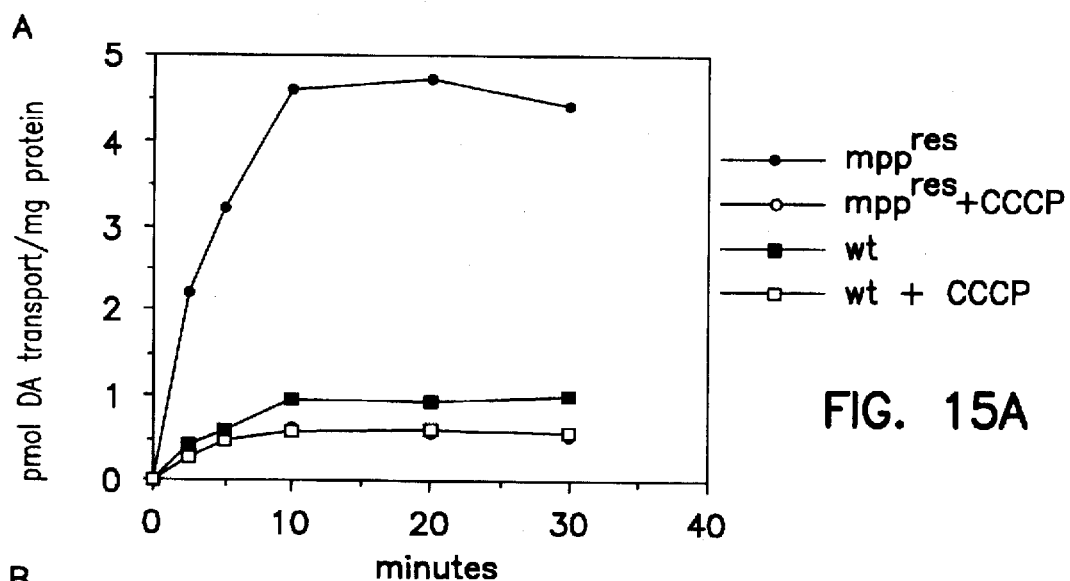
FIGS. 15A–15C are graphs showing the results of a quantitative determination of dopamine uptake by $mpp^{res}$ cells (FIG. 15A: kinetics of incorporation.
Figure 15B:
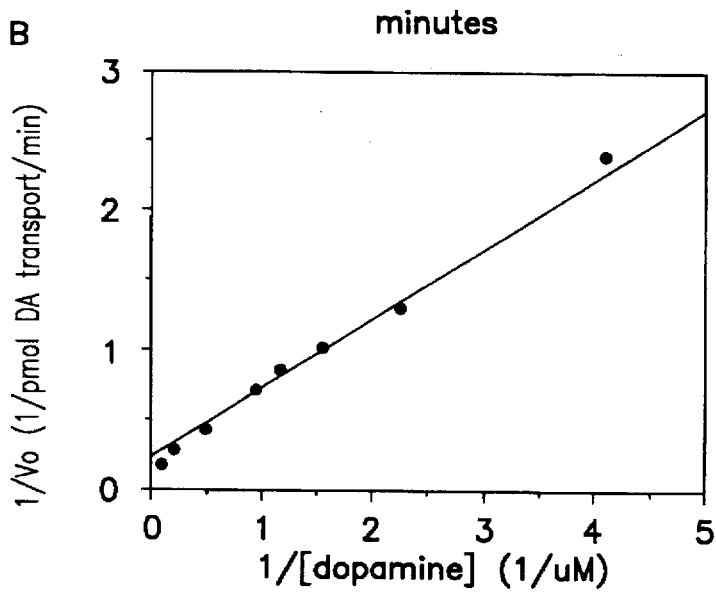
Figure 15C:
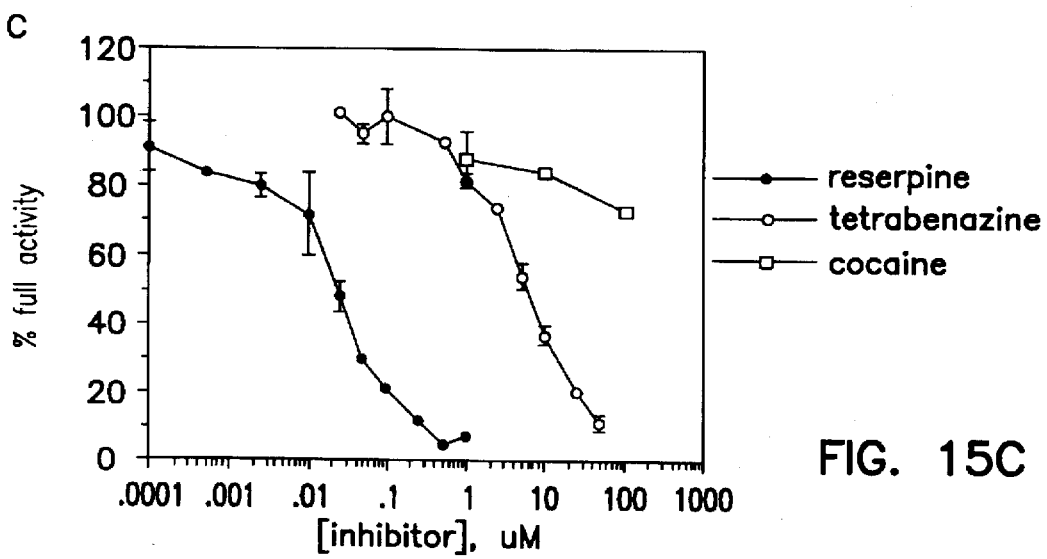

The quantitative transport test was performed as described above on wild-type CHO cells and mpp$^{res}$ CHO cells. The results are shown in FIG. 15. FIG. 15A shows the kinetics of incorporation for both wild-type and mpp$^{res}$ cells. The incorporation by mpp$^{res}$ cells was blocked by the proton ionophore carbonyl cyanide m-chlorophenylhydrazone (CCCP) at a concentration of 5 µM. FIG. 15B shows a Lineweaver-Burke plot of dopamine transport by the mpp$^{res}$ CHO cells based on a 2-minute incubation. The K$_m$ was 2.3 µM. FIG. 15C shows a dose-response analysis of the inhibition of dopamine transport by reserpine, tetrabenazine, and cocaine, based on a 2-minute incubation. These results show that the cloned and expressed CGAT gene yields the pharmacologic properties expected for chromaffin granule transport, with inhibition by both reserpine and tetrabenazine. The activity differs from plasma membrane amine transporters in showing no dependence on external Na$^+$ and no inhibition by cocaine. Thus, functional analysis of the activity encoded by the rescued cDNA shows that it confers vesicular amine transport.

Using the quantitative assay, the affinity for different substrates was also determined. The rank order for affinity was serotonin>epinephrine>dopamine>norepinephrine.

With respect to tissue distribution, a 3.0 kb RNA transcript for the cloned transport protein has been detected only in the rat adrenal gland. However, the level of expression was fairly low even in this tissue, where chromaffin cells constitute a large proportion of the cells, and it may be difficult to detect mRNA transcripts in tissues such as the midbrain where dopaminergic neurons constitute only a small fraction of all of the cells present. However, procedures for screening cDNA libraries from different tissues within species and for different species are available and may be screened as described above using a fragment of the cloned transport protein presented herein as a hybridization probe.

The insert from cDNA mpp$^{res}$ was subcloned into pBluescript™ (Stratagene, San Diego, Calif.) using standard procedures and sequenced on both strands by the dideoxy method using single-stranded templates and Sequenase (USB) as described by Sanger et al., *Proc. Natl. Acad. Sci. USA* 74:5463–5467 (1977). Alignment to the Gen Bank database (University of Wisconsin Genetics Program, Madison, Wis.) was performed at the UCLA biological computing facility (University of California, Los Angeles, Calif.) using profile-based methods as described by Gribskov et al., *Proc. Natl. Acad. Sci. USA* 84:4355–4358 (1987). The MPP$^{res}$ cDNA conferring both resistance to MPP$^+$ and vesicular catecholamine transport contained a 2.5 kb insert. Sequence analysis of this insert showed that the first ATG occurred at the beginning of the largest open reading frame, in a context that conforms to the consensus for translation initiation (FIG. 1) (SEQ ID NO: 1) (Kozak, *Nucl. Acids. Res.* 12:857–872 (1984)). The predicted protein of 521 amino acids shows no strong homology to known proteins, and contains no apparent signal peptide, but does show extensive hydrophobic domains consistent with a membrane protein. The analysis of hydrophobic moment (Eisenberg et al., *J. Mol. Biol.* 179:125–142 (1984)) predicts twelve transmembrane domains, a structure characteristic of other known transport proteins. The largest hydrophilic loop occurs between membrane domains 1 and 2, and contains three potential sites for N-linked glycosylation.

Figure 16:
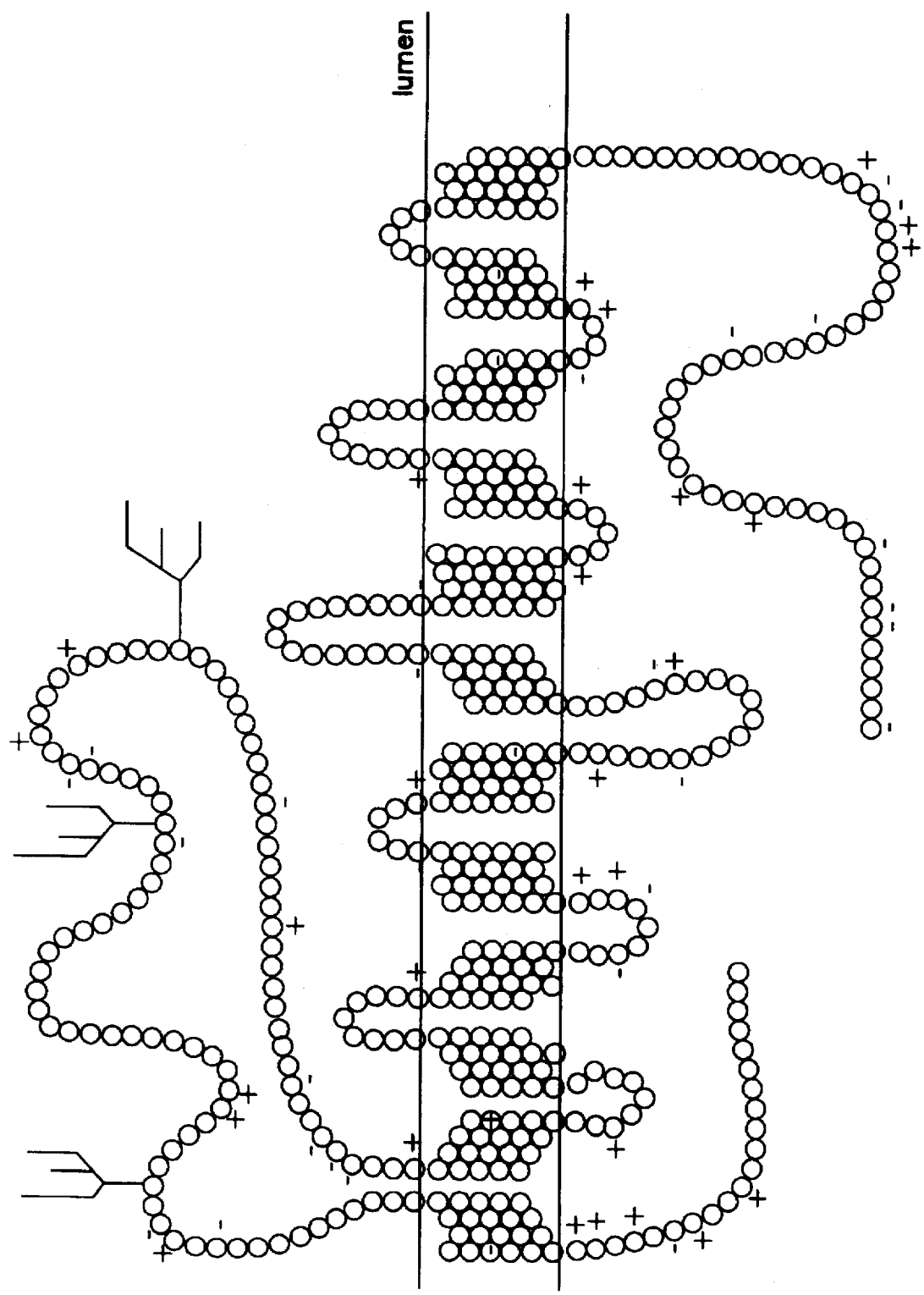
FIG. 16 is a model of the predicted structure of the chromaffin granule amine transport protein as described in Example 2, infra (lumen of the granule is above, cytoplasm below; basic and acidic residues are shown as "+" and "−", respectively, with N-linked carbohydrates in the first lumenal loop indicated by a branched structure).

The model in FIG. 16 shows the hydrophilic loop facing the lumen of the vesicle, with the other loops disposed accordingly, and both N- and C-termini in the cytoplasm. Previous biochemical studies of [$^3$H]-reserpine binding and purification of the transport protein by functional reconstitution have suggested a molecular weight of 80 kd (Stern-Bach et al., supra), consistent with the sequence predicted from the clone mpp$^{res}$.

The cloned vesicle membrane amine transport protein identified herein shows no primary sequence similarity to Na$^+$-dependent, plasma membrane neurotransmitter transport proteins, as expected from its distinct biological role, mechanism of action and pharmacology. Both types of neurotransmitter transporter are predicted to have twelve transmembrane domains, but the single large hydrophilic loop occurs between the first two transmembrane domains of the vesicle transport protein, and between the third and fourth transmembrane helices in the family of plasma membrane transporters (Guastella et al., *Science* 249:1303–1306 (1990); Pacholczyk et al., *Nature* 350:350–354 (1991); Shimada et al., *Science* 254:574–578 (1991); Kilty et al., *Science* 254:578–579 (1991) and Hoffman et al., *Science* 254:579–580 (1991)). However, it is striking that in both cases the loop resides on a topologically equivalent side of the membrane (i.e. inside the vesicle lumen and outside the cell), but the two classes of protein transport in opposing directions suggesting that this loop is not involved in recognition of the substances transported by the protein.

The cloned transport protein demonstrated weak but definite homology with a class of bacterial transporters including the tetracycline resistance genes from pBR322 (SEQ ID NO: 7) and Tn10 (SEQ ID NO: 8), the bacterial multi-drug resistance (BMR) transporter (SEQ ID NO: 9), and more remotely, with a methylenomycin resistance gene (SEQ ID NO: 6) (FIG. 17). The alignment occurred almost exclusively in the N-terminal half of these transporters, with conserved residues in both transmembrane helices and intermembrane loops, but not in the cytoplasmic N-terminus or large lumenal loop between transmembrane domains 1 and 2. The structural similarity is further supported by functional homology between the proteins. First, both classes of transporter mediate the efflux of toxic compounds from the cell interior. Second, both act as proton exchangers. Third, both the chromaffin granule transporter and the bacterial BMR transporter have relatively low substrate specificity. Fourth, reserpine inhibits both the vesicular amine transport protein and the bacterial BMR transporter.

The above results demonstrate that the cloned sequence for the chromaffin vesicle membrane transport protein encodes a member of a novel class of mammalian proteins which transport neurotransmitters and other compounds into vesicles. The selection strategy used to isolate the clone also suggests a role for these proteins in treating Parkinson's disease. For example, expression of transport protein could be increased by gene transfer with herpes virus vectors or by using drugs that affect expression in animal models or tissue culture. It may also be that development of Parkinson's requires a genetic predisposition. Although the disease does not tend to run in families, twin studies have suggested a genetic component which may be required but is not sufficient to cause the disease (see Johnson et al., *Movement Disorders* 5:187–194 (1990)). Therefore, the cloned transporter protein of the invention may be used to identify mutations that predispose an individual to Parkinson's disease. With early diagnosis, it may be possible to prevent the disease by administering other drugs such as deprenyl which have been shown to slow the rate of progression of the disease.

EXAMPLE 3

Cloning and Sequencing of Synaptic Vesicle Amine Transporter Gene from Rat Brainstem To address the possibility that aminergic populations of central nervous system cells express a synaptic vesicle amine transporter (SVAT) that is distinct from the chromaffin granule amine transporter (CGAT), a search for sequences related to CGAT but expressed in the brain was undertaken. Approximately $10^6$ plaques from a bacteriophage λgt10 rat brainstem library (Clontech, Palo Alto, Calif.) were screened on duplicate nylon filters (Biotrans, ICN, Costa Mesa, Calif.) with the CGAT probe labeled by random priming (Feinberg & Vogelstein, Anal. Biochem. 132:6–13 (1983)). The aqueous hybridization procedure of Boulton et al., supra, was used at 60° C., with washes at 55° C. Positive plaques were purified through two additional rounds of screening, subcloned into pBluescript (Stratagene, San Diego, Calif.), and sequenced by the chain termination method (Sanger & Coulson, supra).

The resulting DNA sequences provided the sequence of most of the SVAT gene. However, some gaps remained. To fill these gaps, PCR cloning was used to develop additional clones for sequencing (Marchuk et al., Nucl. Acids Res. 19:1154 (1991)).

PCR was performed by the following procedure: In a total volume of 50 µl, the reaction mixture contained 15 µg of library DNA, 2 mM $MgCl_2$, 2 mM each of the four deoxyribonucleoside triphosphates, 2.5 units of Taq polymerase (Perkin-Elmer-Cetus, Norwalk, Conn.), 1×PCR buffer (Perkin-Elmer-Cetus), and 100 pmole each of 2 primers: a library-specific primer, 5'-GATGATGGAGACCATGTGTTC-3' and a λgt10-specific primer, 5'-GAAAGCTTCTTATGAGTATTTCTTCAAGGGTA-3'. The first cycle of PCR was 94° C. for 5 minutes for denaturing, 60° C. for 30 seconds for annealing, and 72° for 4 minutes for extension. Subsequently, 30 additional cycles were performed at 94° C. for 1 minute for denaturing, 60° C. for 30 seconds for annealing, and 72° for 4 minutes for extension. A final PCR cycle was then performed at 94° C. for 1 minute for denaturing, 60° C. for 30 seconds for annealing, and 72° for 10 minutes for extension.

The resulting PCR products were electrophoresed on a 1% low melting point agarose gel and DNA ranging in size from 4.3 kb to 5 kb was cut out of the gel. This DNA was then ligated at 14° C. with 200 ng of T-vector (pBluescript KSII+ cut with EcoRV). The ligated DNA was then incubated with Taq polymerase at 1 unit of polymerase per µg plasmid in a 20-µl reaction volume with 2 mM dTTP for 2 hours at 68° C. The resulting DNA was then extracted with phenol-chloroform and precipitated with ethanol.

The precipitated DNA was then used for transformation in E. coli and colonies were screened by hybridization using the original cDNA as a probe. In this way, additional clones were isolated that allowed the complete sequence of the SVAT gene to be determined. The DNA sequence of this gene and the amino acid sequence of the corresponding protein are shown in FIG. 2 (SEQ ID NO: 3, & 4). The protein is closely related in sequence to CGAT protein, and also has twelve transmembrane domains.

The relationship between the amino acid sequences of the two proteins is shown in FIG. 4. Extensive sequence divergence occurs principally in the large lumenal loop located between the first two transmembrane proteins of both proteins, and to a lesser extent at the N- and C-termini.

Figure 18A:
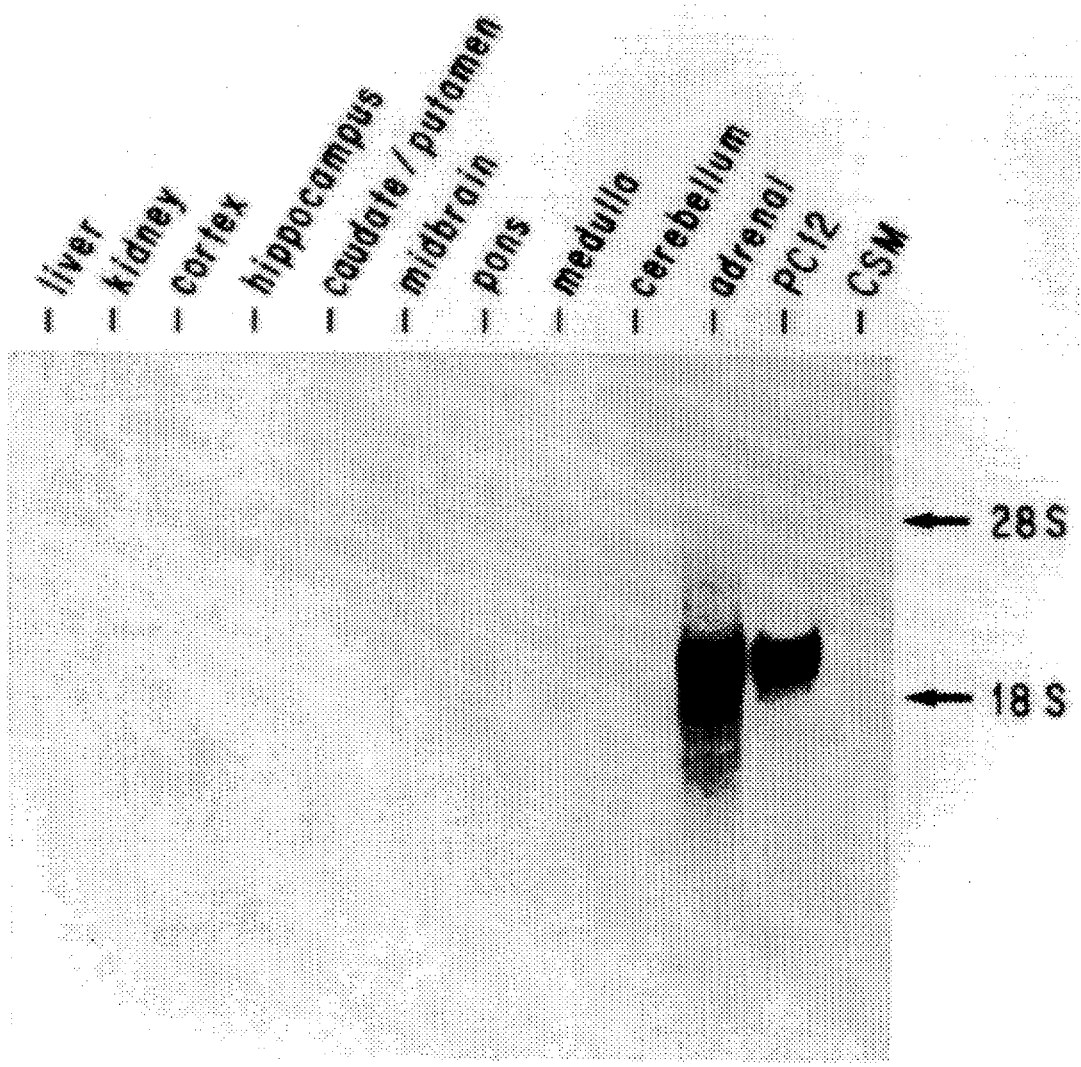
FIG. 18 is a gel showing the results of Northern blotting of mRNA from various tissues showing the differential expression of the chromaffin granule and synaptic vesicle transport proteins (FIG. 18A: chromaffin granule transport protein cDNA of FIG. 1 as probe.
FIG. 18B: synaptic vesicle transport protein cDNA of FIG. 2 as probe).
Figure 18B:
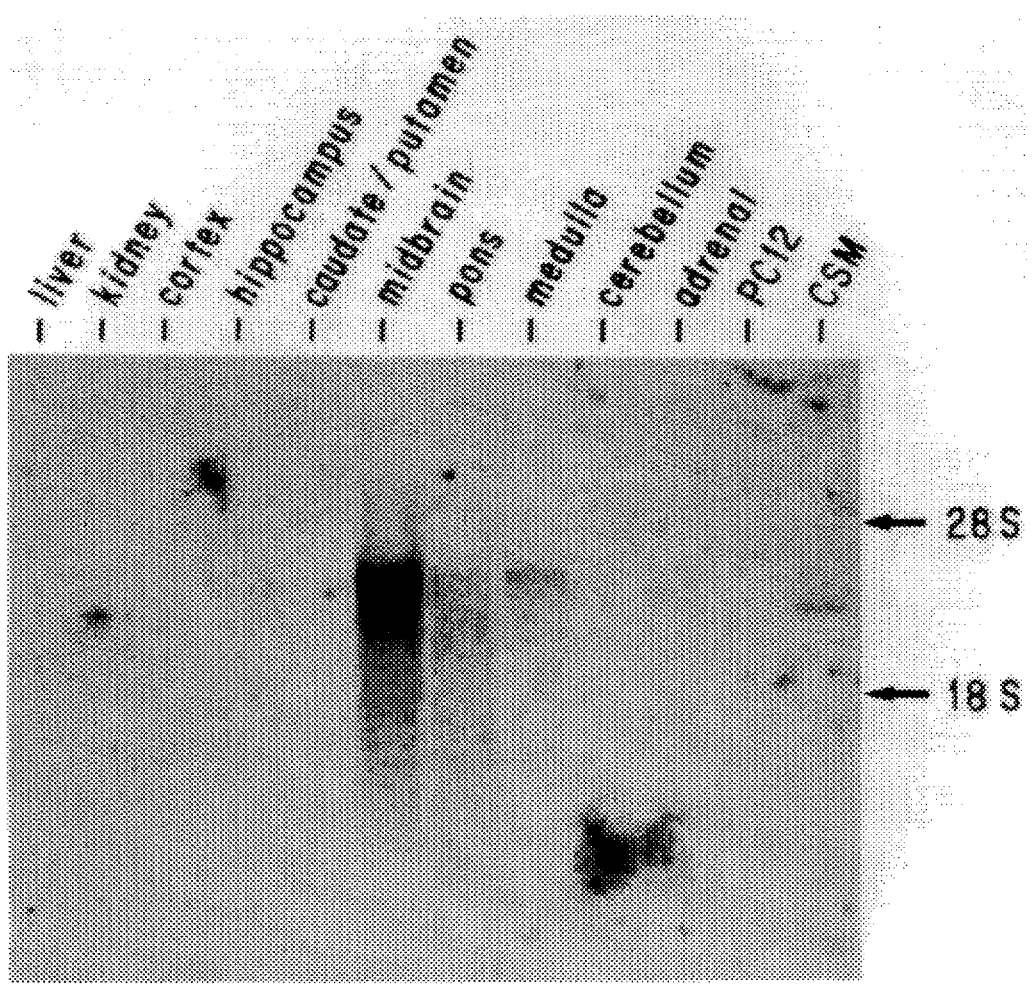

Northern blotting showed that RNA capable of hybridizing to the cloned SVAT cDNA occurred as a transcript of approximately 4 kb in the midbrain, pons, or medulla, but not in the adrenal gland or other peripheral tissues. The RNA used was isolated by disruption of the tissue in 6M guanidinium chloride followed by centrifugation through cesium chloride (Chirgwin et al., Biochemistry 18:5294–5299 (1979)). PolyA+ RNA was isolated by chromatography over oligo-dT cellulose (Aviv & Leder, supra). For Northern analysis, 10 µg total or polyA+ RNA was separated by electrophoresis through 2.2M formaldehyde/1.5% agarose and blotted to nylon (Hybond, Amersham, Arlington Heights, Ill.). For high stringency aqueous hybridization, the hybridization procedure of Boulton et al., supra, was used at 68° C. The results are shown in FIG. 18B; Northern blots to CGAT cDNA are shown in FIG. 18A. The Northern blots show that RNA hybridizing to SVAT cDNA is found only in central nervous system tissues, and not in the adrenal gland or other tissues. These results support the existence of tissue-specific subtypes of the amine transport protein.

Further confirmation of the existence and expression of tissue-specific subtypes was obtained through in situ hybridization. The procedure for in situ hybridization is described in detail in Sternini et al., Gastroenterology 97:348–356 (1989). In brief, the animals were anesthetized with nembutal and perfused with 4% paraformaldehyde (PFA) in PBS. The brain was then dissected, postfixed for an additional 2 hours, cryoprotected with 25% sucrose in 4% PFA/PBS and section in a transverse plane at 30 µm. The sections were then washed in 0.75 mg/ml glycine, digested in 1 µg/ml proteinase K, 50 mM Tris-HCl, pH 8, 5 mM EDTA for 30 minutes at 37° C. and then treated with 0.25% acetic anhydride, 0.1M triethanolamine, pH 8 for 10 minutes at room temperature. Strand-specific RNA probes were prepared from the SVAT cDNA subcloned into pBluescript (Stratagene) using T7 RNA polymerase (Promega, Madison, Wis.) (Cox et al., Dev. Biol. 101:485–502 (1984)). After prehybridization in 50% formamide, 0.75M NaCl, 25 mM EDTA, 25 mM PIPES, pH 6.8, 1×Denhardt's solution, 0.2% SDS, 25 mM dithiothreitol, 250 µg/ml denatured salmon sperm DNA, 250 µg poly rA for more than one hour at 37° C., the sections were hybridized overnight at 55° C. in the same solution containing 5% dextran sulfate and 0.1 ng/ml of the labeled probe. The sections were washed in 4×standard saline citrate (SSC), 50 mM β-mercaptoethanol, treated with 50 µg/ml RNase A for 30 minutes at 37° C., washed in 2× SSC, then in 0.1× SSC at 65° C. and finally in 0.1× SSC at room temperature overnight. The sections were mounted on gelatin-coated slides and exposed to autoradiographic film (Kodak™, Eastman Kodak, Rochester, N.Y.) for 4 days.

Figure 19A:
(FIG. 19A: substantia nigra (SN) and ventral tegmental area (VTA)
Figure 19B:
FIG. 19B: locus coeruleus (LC) and region A5 (A5)
Figure 19C:
FIG. 19C: nucleus raphe pallidus (nrp), nucleus tractus solitarius (nts), and region A1 (A1).

The results of in situ hybridization are shown in FIG. 19. Hybridizing cell populations appeared in the substantia nigra (SN), ventral tegmental area (VTA), locus coeruleus (LC), nucleus raphe pallidus (nrp), nucleus tractus solitarius (nts), and regions A1 and A5, but do not appear in adjacent areas. This is the location of dopaminergic, noradrenergic, and serotonergic cell populations expected to express such a synaptic vesicle amine transport protein.

The existence of different, through related, transporter proteins, expressed in the adrenal gland and in the brain raises the possibility of developing inhibitors or activators that differentially affect the two tissue-specific subtypes. Such inhibitors or activators would allow, for example, the development of compounds that affect adrenal gland activity without affecting the nervous system, or, conversely, compounds intended to treat disorders of the nervous system without affecting adrenal gland function.

EXAMPLE 4

Identification and Sequencing of Human Genomic DNA Sequence Hybridizing with Rat SVAT cDNA Probe Because of expression of rat SVAT protein in aminergic central nervous system cells, an attempt was made to identify a corresponding human gene.

A human genomic library in phage λ EMBL 3 (Stratagene), obtained from Dr. J. Nathan, Johns Hopkins University, was first screened by Southern blotting with the rat CGAT cDNA probe at low stringency (Boulton et al., supra). The rat CGAT cDNA was radiolabeled by random priming (Feinberg & Vogelstein, *Anal. Biochem.* 132:6–13 (1983)). Hybridization was carried out for 16–24 hours at 60° C. in a hybridization solution containing 0.5M sodium phosphate, pH 7.0, 7% SDS, 1% BSA, and 1 mM EDTA. After hybridization, the filters were washed in 40 mM sodium phosphate, pH 7.2, 0.5% BSA, 5% SDS, 1 mM EDTA twice for one hour each at 50° C. and then in 40 mM sodium phosphate, pH 7.2, 1% SDS, 1 mM EDTA twice for one hour each at the same temperature. Positive plaques were picked after autoradiography with enhancement for five to seven days and purified through two additional rounds of screening.

To distinguish between the phage clones encoding CGAT (VAT1) and SVAT (VAT2), a radiolabeled Nco I fragment (+71 to +733) containing the divergent loop between the first and second predicted transmembrane domains was used to probe a Southern blot of DNA from the various phage clones. The hybridization and washes were carried out as described above but at 68° C. for high stringency and the 1.3 kb Eco RI fragment identified from one phage isolate was subcloned into pBS (Stratagene). Sequence analysis was carried out by the dideoxy chain-termination method of Sanger et al., *Proc. Natl. Acad. Sci. USA* 74:5463–5467 (1977). The sequence analysis of double-stranded plasmid DNA showed an exon with predicted amino acid sequence highly related to the large lumenal loop in rat SVAT and unrelated to the same region of rat CGAT (FIG. 5) (SEQ ID NO: 5).

The sequence of the human genomic DNA corresponding to the rat SVAT DNA probe is shown in FIG. 5 (SEQ ID NO: 5). The sequenced region represents about 300 bases of an exon plus a few bases of an adjoining intron. The degree of homology between the exon and the rat SVAT cDNA is substantial, with stretches of up to 15 bases showing complete homology.

The sequence of the exon and surrounding introns in the SCAT (VAT2) genomic phage subclone were used to design the following oligonucleotide primers for PCR (from 5' to 3'): hloop 1, CTGACTAAAGTAGTCTGCC (SEQ ID NO: 14) (intron); hloop 2, TACAGAAATCCAGACGG (SEQ ID NO: 15) (exon); hloop 3, CGTCTGGATTTCTGTAG (SEQ ID NO: 16) (exon); hloop 4, GGCATGGTGCTTTCTAG (SEQ ID NO: 16) (intron). The PCR was then performed by denaturing hloop 1 and 2 or hloop 3 and 4 with 25 ng genomic DNA in standard PCR buffer containing 1.5 mM MgCl$_2$ (Perkin-Elmer Cetus, Norwalk, Conn.) at 94° C. for four minutes, followed by 35 cycles of denaturation at 94° C. for one minute, annealing at 55° C. for two minutes, and extension at 72° C. for four minutes. After separation of the products by electrophoresis through 1.4% agarose, a Southern blot of the gel was hybridized to the radiolabeled 1.3 kb Eco RI subclone under high stringency and submitted to autoradiography.

Figure 20:
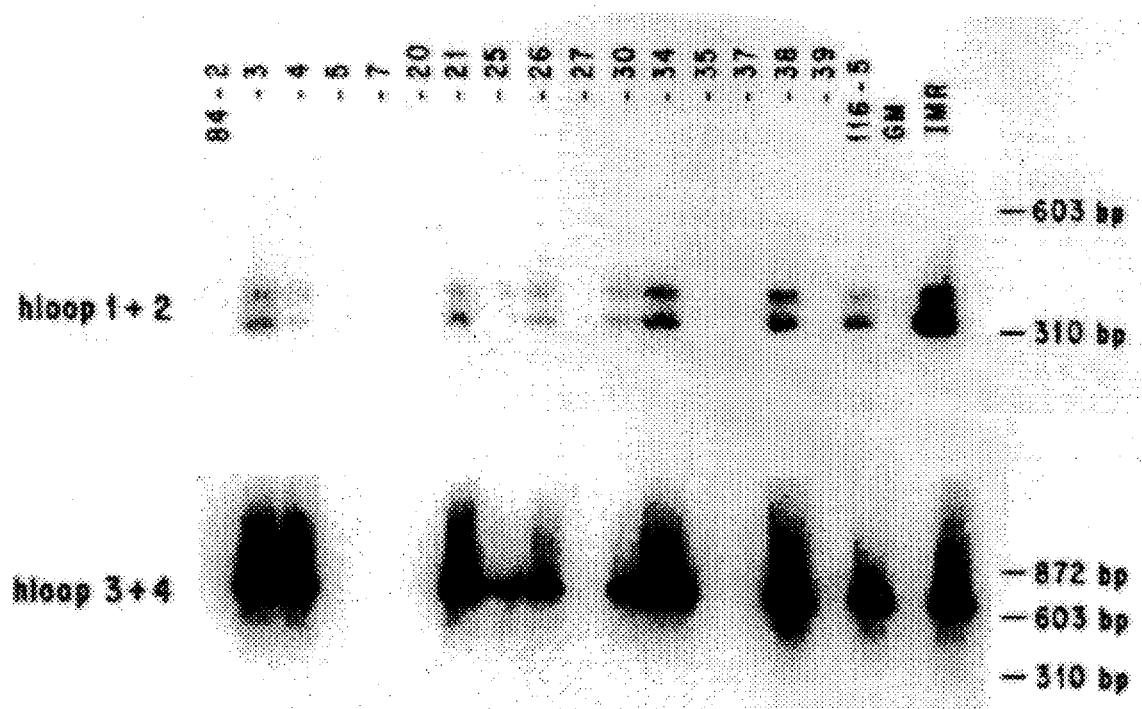
FIG. 20 is an autoradiograph showing the results of polymerase chain reaction (PCR) analysis using two sets of primers (SEQ ID NO: 14, 15, 16, and 17) in order to localize the human SVAT gene to chromosome 10. (IMR: human genomic DNA; GM: mouse genomic DNA).

The results are shown in FIG. 20. Despite the smaller size of the resulting fragment, amplification with hloop 1 and 2 oligonucleotide primers appears less efficient than with hloop 3 and 4, but both show the same pattern of amplification in the panel of cell hybrids. The pattern indicates localization of the human SVAT gene to chromosome 10.

For isolation of human SVAT cDNA, a human midbrain cDNA library in λ bacteriophage gt10 (Clontech, Palo Alto, Calif.) was screened with the rat SVAT cDNA as described above for the isolation of the human SVAT gene from the genomic library. Ten positive plaques were picked and purified and the phage DNA prepared. To determine which of the clones contained a full length cDNA, oligonucleotide primers from the 5' and 3' ends of rat SVAT were used to amplify the phage DNA by PCR as described above. A single clone yielded a PCR product of the appropriate size and the insert from this phage was subcloned for sequence analysis on both strands by the chain-termination method of Sanger et al., supra.

The use of the large lumenal loop as a probe was to distinguish between the human equivalents of rat SVAT and rat CGAT, because this section of the DNA diverges extensively between the two genes. This probe should therefore selectively hybridize with the human SVAT gene rather than the human CGAT gene, assuming substantial homology between the rat and human sequences of the corresponding transporter genes. Sequence analysis of the subclone fragment confirmed a strong similarity to rat SVAT relative to rat CGAT in the region of the large lumenal loop for the human gene. This sequence showed virtually no similarity to rat CGAT.

The sequence of the human SVAT cDNA is shown in FIG. 3 (SEQ ID NO: 12) and supports the identity of the isolated genomic phage clone as the human SVAT gene. In FIG. 21, a comparison of the predicted amino acid sequence encoded by the human SVAT DNA with the predicted amino acid sequences encoded by rat SVAT and CGAT cDNAs is shown. The predicted human SVAT protein sequence has 92.5% identity and 96.5% homology to rat SVAT. Most of the divergence occurs in the large lumenal loop between the first two transmembrane domains, but the human and rat SVAT sequences still show considerable homology in this region, in contrast with the more striking divergence between rat CGAT and SVAT. A similar comparison of the cDNA sequences for human SVAT, rat SVAT, and rat CGAT is shown in FIG. 22.

The sequence of the human SVAT cDNA confirms the sequence of the exon obtained from the gene. In addition, human SVAT shows striking similarity to rat SVAT. The similarity includes both ends of the protein and the large lumenal loop between transmembrane domains 1 and 2, a region of strong divergence between rat CGAT and rat SVAT. Conservation in these regions of the protein suggests an important physiologic role that may differ between SVAT and CGAT. A recent paper describes the isolation of a human SVAT cDNA with a somewhat different sequence then that presented here (C. K. Surratt et al., *FEBS Lett.* 318:325–330 (1993)). This different DNA sequence results in an amino acid sequence differing at 4 residues in the carboxy-terminal half of the protein. Although these differences may represent true species variation or a very closely related member of this gene family, the conservation of the residues reported here in two distinct genes from another species (rat SVAT and rat CGAT) strongly suggests that these amino acids do not vary within the human population for SVAT. Further, the substitution of a serine for a cysteine in the middle of transmembrane domain 7, a threonine for a lysine in the cytoplasmic loop following transmembrane domain 8, a proline for an alanine at the border of transmembrane domain 9, and an asparagine for an isoleucine in transmembrane domain 10, may well disrupt transporter structure or function. These changes cannot properly be considered conservative amino acid substitutions, because they alter charge, polarity, and the tendency to form a α-helix. In addition to this clear sequence information obtained from both strands, the conservation of these critical residues in rat CGAT and rat SVAT strongly supports the sequence presented here.

EXAMPLE 5

Determination of Chromosomal Location of Human Gene Encoding the Chromaffin Granule Amine Transporter In order to determine the chromosomal location of the human gene in coding the chromaffin granule amine transporter, we used Southern analysis of genomic DNA from mouse/human hybrid cell lines. A panel of 17 mouse/human somatic cell hybrids was derived from the fusion of thymidine kinase deficient mouse cells (B82, GM 0347 A) and normal male fibroblasts (IMR91) as described in T. Mohandas et al., *Somatic Cell & Mol. Genet.* 12:89–94 (1986). Cytogenetic analysis was carried out on a minimum of 30 Q-banded metaphases per hybrid clone.

To carry out Southern analysis, genomic DNA from the human and mouse parental cell lines and somatic cell hybrid clones was digested with the restriction endonuclease Eco RI (8 U/μg DNA). Approximately 10 μg from each sample was electrophoresed through 1.2% agarose in 40 mM Tris-acetate, pH 7.4, 1 mM EDTA (TEA), transferred by capillary action to Nytran™ (Schleicher & Schuell, Keene, N.H.) and immobilized by cross-linking with ultraviolet light. Prehybridization was performed at 0.5M M sodium phosphate, pH 7.0, 7% SDS, 1% BSA, 1 mM EDTA for four hours at 60° C. and hybridization in the same solution containing the CGAT cDNA radiolabeled by random priming (Feinberg & Vogelstein, supra) for 24 hours at the same temperature (Boulton et al., supra). The filter was washed twice in 2×standard saline citrate (SSC), 0.1% SDS for 20 minutes each at 65° C., twice in 0.1× SSC, 0.1% SDS for 20 minutes at 65° C., and then exposed with an enhancing screen at −70° C. to XAR-5 X-ray film (Kodak, Rochester, N.Y.) for two to five days.

Figure 23:
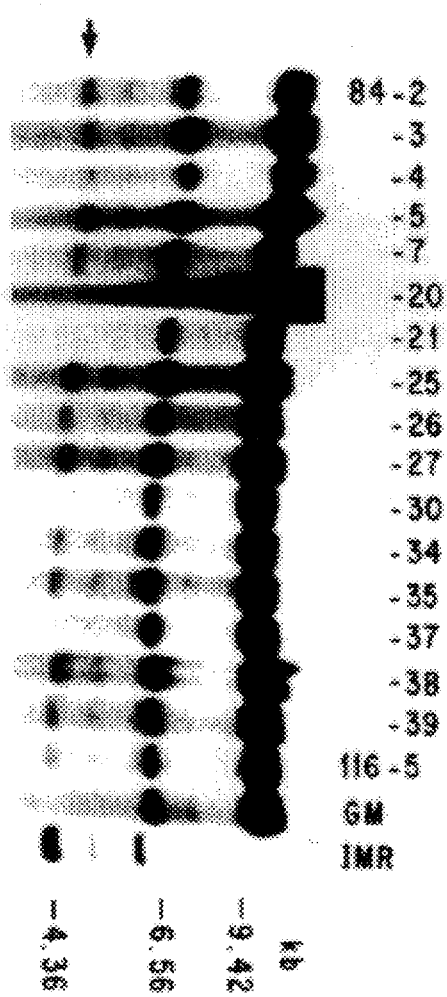
FIG. 23 is an autoradiograph showing the results of Southern blot analysis localizing the human CGAT gene to chromosome 8, with mouse (GM) and human (IMR) DNA.

The results of Southern blot hybridization are shown in FIG. 23. Under conditions of high stringency, the rat CGAT cDNA as probed identified a unique set of Eco RI fragments in human cells, distinct from those present in mouse cells (FIG. 23). The number of fragments (3 with Eco RI digestion) suggested possible hybridization to several genes on different chromosomes. However, hybridization to a panel of DNA from mouse/human hybrids indicated the localization of all of these fragments to chromosome 8, with no discordant hybrids and no ambiguity (Table 2).

TABLE 2

| | \multicolumn{24}{c}{Human Chromosomes} |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
| CGAT (VAT1) | | | | | | | | | | | | | | | | | | | | | | | | |
| Concordant | | | | | | | | | | | | | | | | | | | | | | | | |
| +/+ | 5 | 6 | 9 | 10 | 6 | 12 | 9 | 13 | 0 | 7 | 5 | 8 | 5 | 9 | 10 | 3 | 12 | 8 | 7 | 9 | 5 | 6 | 2 | 1 |
| −/− | 2 | 3 | 2 | 1 | 0 | 1 | 1 | 3 | 3 | 1 | 2 | 0 | 2 | 0 | 3 | 3 | 0 | 2 | 3 | 0 | 0 | 1 | 3 | 2 |
| Discordant | | | | | | | | | | | | | | | | | | | | | | | | |
| +/− | 8 | 7 | 4 | 3 | 7 | 1 | 4 | 0 | 13 | 6 | 8 | 5 | 8 | 4 | 3 | 10 | 1 | 5 | 6 | 4 | 8 | 7 | 11 | 12 |
| −/+ | 1 | 0 | 1 | 2 | 3 | 2 | 2 | 0 | 0 | 2 | 1 | 3 | 1 | 3 | 0 | 0 | 3 | 1 | 0 | 3 | 3 | 2 | 0 | 1 |
| Total discordant hybrids | 9 | 7 | 5 | 5 | 10 | 3 | 6 | 0 | 13 | 8 | 9 | 8 | 9 | 7 | 3 | 10 | 4 | 6 | 6 | 7 | 11 | 9 | 11 | 13 |
| Total informative hybrids | 16 | 16 | 16 | 16 | 16 | 16 | 16 | 16 | 16 | 16 | 16 | 16 | 16 | 16 | 16 | 16 | 16 | 16 | 16 | 16 | 16 | 16 | 16 | 16 |
| SVAT (VAT2) | | | | | | | | | | | | | | | | | | | | | | | | |
| Concordant | | | | | | | | | | | | | | | | | | | | | | | | |
| +/+ | 6 | 3 | 6 | 8 | 5 | 8 | 6 | 7 | 0 | 9 | 2 | 6 | 5 | 7 | 5 | 1 | 8 | 6 | 6 | 8 | 5 | 5 | 1 | 2 |
| −/− | 7 | 4 | 3 | 3 | 3 | 2 | 2 | 0 | 8 | 8 | 3 | 2 | 7 | 2 | 3 | 6 | 0 | 4 | 6 | 3 | 4 | 4 | 6 | 8 |
| Discordant | | | | | | | | | | | | | | | | | | | | | | | | |
| +/− | 3 | 6 | 3 | 1 | 4 | 1 | 1 | 2 | 9 | 0 | 7 | 3 | 4 | 2 | 4 | 8 | 1 | 3 | 3 | 1 | 4 | 4 | 8 | 7 |
| −/+ | 1 | 4 | 5 | 5 | 5 | 6 | 6 | 8 | 0 | 0 | 5 | 6 | 1 | 6 | 5 | 2 | 8 | 4 | 2 | 5 | 4 | 4 | 2 | 0 |
| Total discordant hybrids | 4 | 10 | 8 | 6 | 9 | 7 | 7 | 10 | 9 | 0 | 12 | 9 | 5 | 8 | 9 | 10 | 9 | 7 | 5 | 6 | 8 | 8 | 10 | 7 |
| Total Informative hybrids | 17 | 17 | 17 | 17 | 17 | 17 | 17 | 17 | 17 | 17 | 17 | 17 | 17 | 17 | 17 | 17 | 17 | 17 | 17 | 17 | 17 | 17 | 17 | 17 |

On the other hand, hybridization of a Southern blot from the same hybrids using the synaptic vesicle amine transporters cDNA as probe gave ambiguous results, perhaps as a result of cross-hybridization to other sequences in the human genomic DNA.

In situ hybridization with a $^3$H-labeled cDNA probe confirmed the localization of the CGAT gene on human chromosome 8. For in situ hybridization, peripheral blood from normal donors was cultured for three days in RPMI 1640 supplemented with 20% fetal calf serum and 3% phytohemagglutinin, then synchronized with 0.1 μM methotrexate overnight, washed twice in unsupplemented RPMI and incubated in 30 μg/ml bromodeoxyuridine for seven hours. The cells were then arrested in metaphase with 0.5 μg/ml colchicine, lysed in 0.075M KCl for fifteen minutes at 37° C., sedimented, fixed with Carnoy's mixture (methanol: acetic acid, 3:1), spread onto glass slides and dried.

For standard in situ hybridization with $^3$H-labeled probes, the purified insert from the CGAT cDNA was labeled by random priming with [$^3$H]dNTPs to a specific activity of approximately 3×10$^8$ cpm/μg and the hybridization performed according to the method of Harper & Saunders,

*Chromosoma* 83:431–439 (1981) as modified by Cannizzaro & Emanuel, *Cytogenet. & Cell Genet.* 38:308–309 (1984). The slides were dipped in photographic emulsion, exposed for one week and all silver grains on or touching chromosomes were scored.

Figure 24:
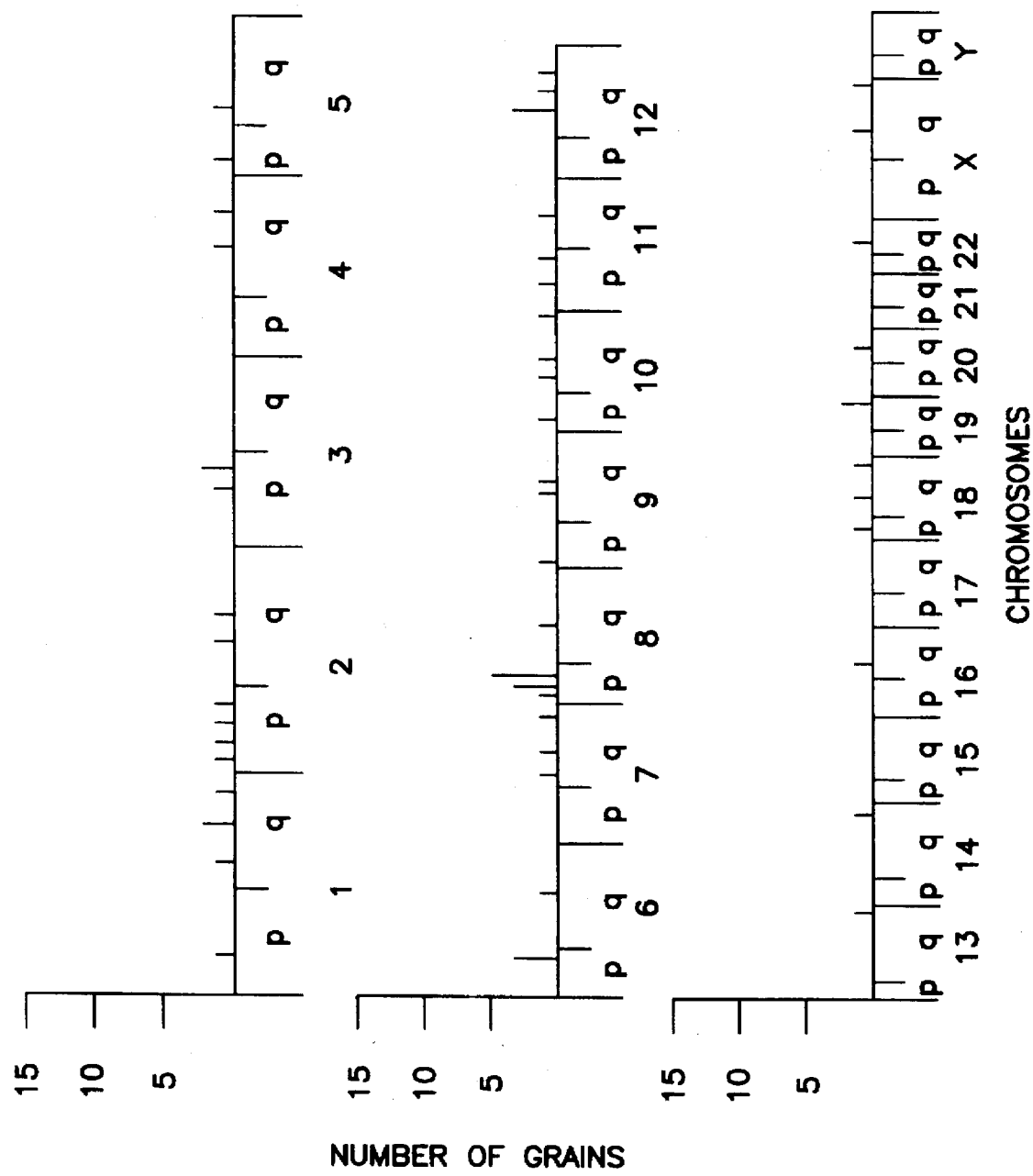
FIG. 24 is an diagram based on autoradiographic data showing the results of in situ hybridization localizing the human CGAT gene to chromosome 8p, indicated by the distribution of silver grains.

The results are shown in FIG. 24. The grain counts on nine chromosome spreads showed regional localization to 8p21.3 (Harnden & Klinger, "An International System for Human Cytogenetic Nomenclature," Karger, Basel (1985)).

Localization of human CGAT at 8p21.3 occurs relatively close to the genes for lipoprotein lipase at 8p22 (R. S. Sparkes et al., *Genomics* 1:138–144 (1987)), glutathione reductase at 8p21.1 (P. K. A. Jensen et al., *Ann. Genet.* 25:207–211 (1982)) and the light neurofilament chain at 8p21 (J. Hurst et al., *Cytogenet. Cell Genet.* 45: 30–31 (1987); M. J. Summerville et al., *Genome* 30: 499–500 (1988)). Deletions have similarly localized the genes for erythrocyte ankyrin (S. E. Lux et al., *Nature* 345: 736–739 (1990)), luteinizing hormone releasing hormone (T. L. Yang-Feng et al., *Cytogenet. Cell Genet.* 42: 7016 (1991)) and an alpha-one-like adrenergic receptor (D. A. Schwinn et al., *J. Biol. Chem.* 265:8183–8189 (1990); Yang-Feng et al. (1991), supra) to this general vicinity. Several disease loci occur in this region but none with a prominent autonomic phenotype to suggest a disturbance of monoamine synaptic transmission.

Hereditary spherocytosis usually affects red blood cells relatively selectively and does not show gross chromosomal abnormalities. However, recent reports describe hereditary spherocytosis due to a deletion of chromosome 8 from 8p11 to 8p21 (F. F. Costa et al., *New Engl. J. Med.* 323:1046–1050 (1990); Lux et al. (1990), supra). These patients have a more serious disorder affecting a wide range of systems in addition to the hematopoietic. The phenotype includes dysmorphic features, psychomotor retardation, and abnormal eye movements. Thus, the more serious phenotype presumably results from a monosomy for a variety of genes in addition to erythrocyte ankyrin that may include the gene for CGAT and so account for several of the associated abnormalities.

EXAMPLE 6

Determination of Chromosomal Location of Human Gene Encoding the Synaptic Vesicle Amine Transporter The regional localization of SVAT in the human genome was determined by fluorescent in situ hybridization using a biotinylated probe derived from the genomic phage clone that contained the large lumenal loop of SVAT. The entire phage DNA was labeled by nick translation with biotinylated dATP (BioNick, Gibco/BRL, Gaithersburg, Md.), hybridized for 48 hours at 37° C. (Hybrisol VII, Oncor, Gaithersburg, Md.), washed in 50% formamide-2× SSC for two minutes at 37° C., in 2× SSC for two minutes at 37° C. and the hybridized probe visualized (Chromosome In Situ Kit, Oncor) with avidin-fluorescein under epifluorescence with a Leitz Orthoplan microscope after counterstaining with propidium diiodide. To determine the specific region and to confirm the identification of the chromosome, the spreads were sequentially T-G banded (Cannizzaro & Emanuel (1984), supra).

Figure 25:
FIG. 25 is a photograph showing the results of fluorescent in situ hybridization localizing the human SVAT gene to chromosome 10q, the single positively hybridizing chromosome indicated by the arrow.

The results of in situ hybridization are shown in FIG. 25. The twin florescent spots seen on 27 metaphase spreads confirm the presence of the human SVAT gene on chromosome 10 and indicated specific localization to the 10q25 region.

Figure 26:
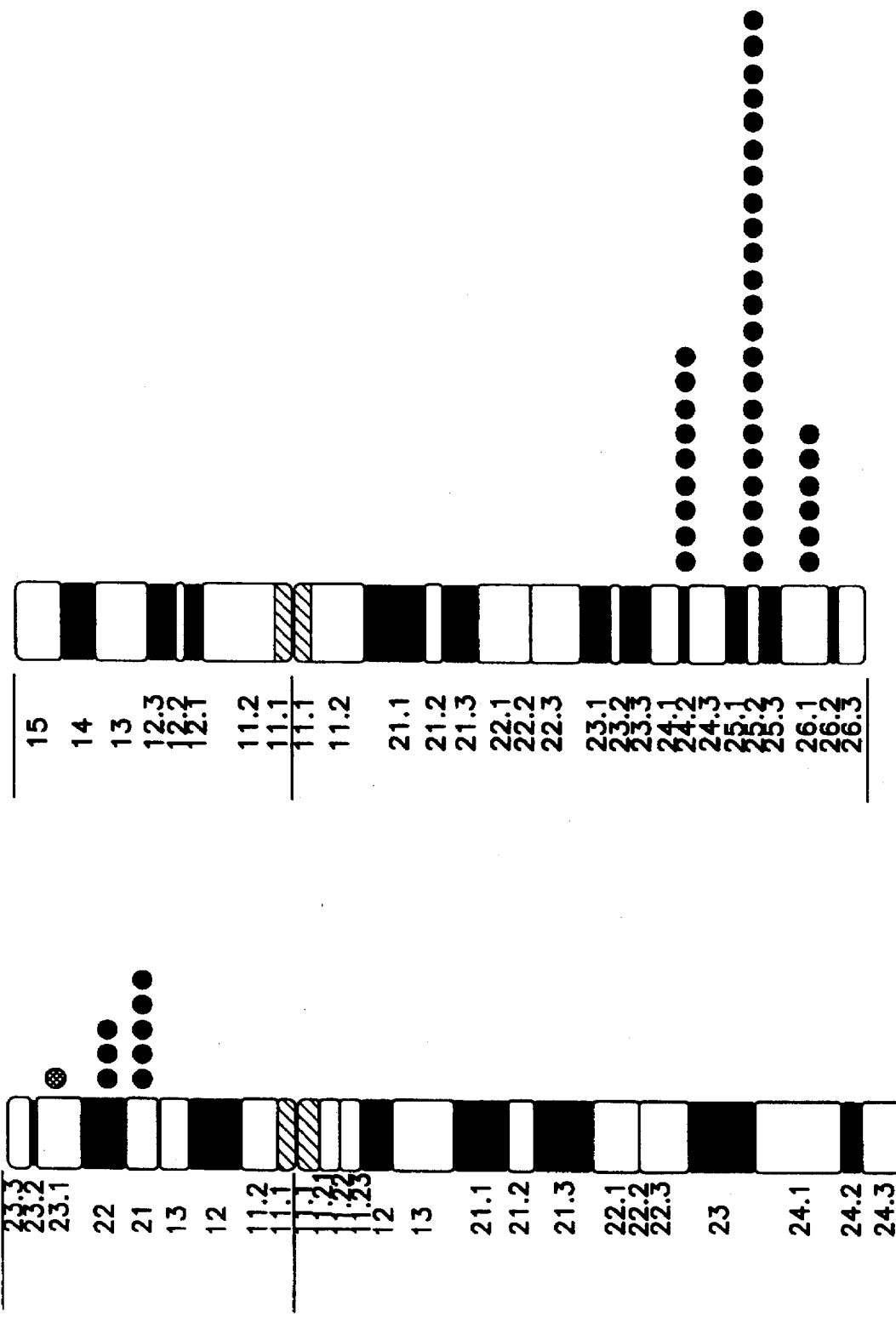
FIG. 26 is a diagram showing the results of sequential T-G banding to demonstrate localization of grain counts for in situ hybridization to chromosome 8p21.3 for human CGAT, and chromosome 10g25 for human CGAT.

FIG. 26 shows the results of the analysis of sequentially T-G-banded chromosome spreads in order to verify both the chromosomal and regional localizations for both CGAT and SVAT. This indicates that the human CGAT gene is localized at chromosome 8p21.3, and the human SVAT gene is localized at chromosome 10q25. The latter result is based on the analysis of 19 chromosome spreads.

A number of previously characterized genes surround the human gene for SVAT on the long arm of chromosome 10. These include the genes from metabolic enzymes such as phosphoglycerate mutase, glutamate oxaloacetate transaminase (C. Junien et al., *Ann. Genet. (Paris)* 25:25–27 (1982)) and uroporphyrinogen III synthase (K. H. Astrin et al., *Hum. Genet.* 87:18–22 (1991)) as well as the gene for the insulin-degrading enzyme (J. A. Affholter et al., *Mol. Endocrinol.* 4:1125–1135 (1990)). Interestingly, the genes encoding two receptors from monoamines, the beta-1 adrenergic receptor and the alpha-1 adrenergic receptor (Yang-Feng et al. (1991), supra) also occur in this region. Although no inherited diseases with a simple behavioral phenotype show genetic linkage to this region, deletions from 10q25 and 10q26 to the end of the chromosome have appeared in the literature (R. C. J. Lewandowski et al., *Hum. Genet.* 42:339–343 (1978); R. F. Wegner et al., *Clin. Genet.* 19:130–133 (1981); M. Mulcahy et al., *Clin. Genet.* 21:33–35 (1982); G Evans-Jones et al., *Clin. Genet.* 24:216–219 (1983)). The phenotype associated with this deletion as well as with a trisomy for the end of 10q (J. M. Klep-de-Pater et al., *Hum. Genet.* 46:29–40 (1979)) includes dysmorphic features and severe mental retardation, presumably resulting from a monosomy from multiple genes. SVAT almost certainly belongs to the genes lost in the deletion and so may have a significant role in the pathogenesis of the observed developmental delay and hypotonia. Monoamine cell populations project throughout the central nervous system and influence both cognitive processes and spinal reflexes.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

---

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
  ( A ) LENGTH: 2421 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Rattus rattus ( i x ) FEATURE:
  ( A ) NAME/KEY: CDS
  ( B ) LOCATION: 262..1824

( x i ) SEQUENCE DESCRIPTION: SEQ ID NO:1:

```
CCTCGAGATC CATTGTGCTC TAAAGTCAGC ACATCCACTT TCAGAGAACA GAGTCTCTGC          60

TGTCTTGCCA ACGGCTGCTC CTTCCTCTCT GAGTGCCTCA CATCAAGATA AGCTAGAAGT        120

GAGCTTCACT GGACCAGGCA GACTTCTTCT CCTATAAAGG TGACAGAAGA CCACATTTGT        180

CGAGGGGTCT TCCTAAGCCC TGGGAGGAGA AGCCCCCACC ATCTCACTCC CTACCCAGCC        240

CAGCCTCCTG CAGCCCTTGC C ATG CTC CAG GTT GTT CTG GGT GCT CCT CAG          291
                         Met Leu Gln Val Val Leu Gly Ala Pro Gln
                          1               5                  10

CGG TTG CTG AAG GAA GGA AGG CAG TCC CGC AAG CTG GTG CTG GTG GTG          339
Arg Leu Leu Lys Glu Gly Arg Gln Ser Arg Lys Leu Val Leu Val Val
             15                  20                  25

GTG TTC GTG GCT CTG CTT CTG GAC AAC ATG CTG CTC ACT GTG GTG GTG          387
Val Phe Val Ala Leu Leu Leu Asp Asn Met Leu Leu Thr Val Val Val
         30                  35                  40

CCC ATT GTG CCC ACC TTC CTG TAC GCG ACA GAG TTC AAA GAC AGC AAC          435
Pro Ile Val Pro Thr Phe Leu Tyr Ala Thr Glu Phe Lys Asp Ser Asn
             45                  50                  55

TCT TCT CTG CAT AGG GGT CCT TCT GTA AGC TCC CAG CAA GCT CTC ACC          483
Ser Ser Leu His Arg Gly Pro Ser Val Ser Ser Gln Gln Ala Leu Thr
         60                  65                  70

TCT CCT GCC TTC TCT ACC ATA TTC TCC TTC TTT GAC AAC ACC ACC ACG          531
Ser Pro Ala Phe Ser Thr Ile Phe Ser Phe Phe Asp Asn Thr Thr Thr
 75                  80                  85                  90

ACT GTA GAA GAA CAT GTA CCC TTC CGT GTA ACT TGG ACA AAT GGC ACC          579
Thr Val Glu Glu His Val Pro Phe Arg Val Thr Trp Thr Asn Gly Thr
                 95                 100                 105

ATC CCT CCT CCA GTC ACT GAA GCC AGC TCA GTA CCA AAA AAC AAC TGC          627
Ile Pro Pro Pro Val Thr Glu Ala Ser Ser Val Pro Lys Asn Asn Cys
             110                 115                 120

TTG CAA GGG ATA GAG TTC TTA GAA GAA GAA AAC GTT CGG ATT GGG ATT          675
Leu Gln Gly Ile Glu Phe Leu Glu Glu Glu Asn Val Arg Ile Gly Ile
             125                 130                 135

CTA TTT GCT TCA AAA GCT TTG ATG CAA CTT CTG GTC AAC CCA TTT GTA          723
Leu Phe Ala Ser Lys Ala Leu Met Gln Leu Leu Val Asn Pro Phe Val
         140                 145                 150

GGA CCT CTT ACT AAC AGG ATT GGC TAT CAC ATC CCC ATG TTT GTT GGC          771
Gly Pro Leu Thr Asn Arg Ile Gly Tyr His Ile Pro Met Phe Val Gly
155                 160                 165                 170

TTT ATG ATC ATG TTT CTC TCC ACA CTA ATG TTT GCT TTC TCT GGC ACC          819
Phe Met Ile Met Phe Leu Ser Thr Leu Met Phe Ala Phe Ser Gly Thr
                 175                 180                 185

TAT GCC CTG CTA TTT GTG GCC CGA ACT CTC CAA GGC ATT GGA TCT TCG          867
Tyr Ala Leu Leu Phe Val Ala Arg Thr Leu Gln Gly Ile Gly Ser Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 190 |     |     |     |     | 195 |     |     |     |     | 200 |     |     |      |
| TTT | TCA | TCT | GTT | GCA | GGA | CTT | GGG | ATG | CTG | GCC | AGT | GTC | TAT | ACT | GAC | 915  |
| Phe | Ser | Ser | Val | Ala | Gly | Leu | Gly | Met | Leu | Ala | Ser | Val | Tyr | Thr | Asp |      |
|     | 205 |     |     |     | 210 |     |     |     |     | 215 |     |     |     |     |     |      |
| AAC | TAT | GAG | AGA | GGG | AGA | GCC | ATG | GGA | ATT | GCT | TTG | GGG | GGC | CTG | GCC | 963  |
| Asn | Tyr | Glu | Arg | Gly | Arg | Ala | Met | Gly | Ile | Ala | Leu | Gly | Gly | Leu | Ala |      |
| 220 |     |     |     |     | 225 |     |     |     |     | 230 |     |     |     |     |     |      |
| TTG | GGA | CTT | CTG | GTG | GGA | GCA | CCT | TTC | GGA | AGT | GTG | ATG | TAT | GAA | TTT | 1011 |
| Leu | Gly | Leu | Leu | Val | Gly | Ala | Pro | Phe | Gly | Ser | Val | Met | Tyr | Glu | Phe |      |
| 235 |     |     |     | 240 |     |     |     |     | 245 |     |     |     |     | 250 |     |      |
| GTG | GGC | AAG | TCC | TCA | CCA | TTC | CTC | ATC | TTG | GCC | TTC | TTG | GCA | CTT | CTG | 1059 |
| Val | Gly | Lys | Ser | Ser | Pro | Phe | Leu | Ile | Leu | Ala | Phe | Leu | Ala | Leu | Leu |      |
|     |     |     |     | 255 |     |     |     | 260 |     |     |     |     | 265 |     |     |      |
| GAT | GGA | GCT | CTC | CAA | CTT | TGC | ATC | CTA | TGG | CCT | TCG | AAA | GTG | TCT | CCT | 1107 |
| Asp | Gly | Ala | Leu | Gln | Leu | Cys | Ile | Leu | Trp | Pro | Ser | Lys | Val | Ser | Pro |      |
|     |     |     | 270 |     |     |     |     | 275 |     |     |     |     | 280 |     |     |      |
| GAG | AGT | GCC | ATG | GGG | ACT | TCG | CTT | TTG | ACG | CTT | CTC | AAA | GAC | CCT | TAC | 1155 |
| Glu | Ser | Ala | Met | Gly | Thr | Ser | Leu | Leu | Thr | Leu | Leu | Lys | Asp | Pro | Tyr |      |
|     |     | 285 |     |     |     |     | 290 |     |     |     |     | 295 |     |     |     |      |
| ATC | CTG | GTA | GCA | GCA | GGT | TCC | ATC | TGC | TTG | GCC | AAC | ATG | GGA | GTC | GCC | 1203 |
| Ile | Leu | Val | Ala | Ala | Gly | Ser | Ile | Cys | Leu | Ala | Asn | Met | Gly | Val | Ala |      |
|     |     | 300 |     |     |     | 305 |     |     |     |     | 310 |     |     |     |     |      |
| ATA | CTA | GAG | CCC | ACG | CTG | CCC | ATC | TGG | ATG | ATG | CAG | ACC | ATG | TGC | TCC | 1251 |
| Ile | Leu | Glu | Pro | Thr | Leu | Pro | Ile | Trp | Met | Met | Gln | Thr | Met | Cys | Ser |      |
| 315 |     |     |     |     | 320 |     |     |     | 325 |     |     |     |     |     | 330 |      |
| CCC | GAG | TGG | CAG | CTA | GGT | CTG | GCT | TTC | TTG | CCT | GCT | AGT | GTG | GCC | TAC | 1299 |
| Pro | Glu | Trp | Gln | Leu | Gly | Leu | Ala | Phe | Leu | Pro | Ala | Ser | Val | Ala | Tyr |      |
|     |     |     |     | 335 |     |     |     |     | 340 |     |     |     |     | 345 |     |      |
| CTC | ATT | GGC | ACG | AAC | CTC | TTT | GGT | GTG | TTG | GCT | AAC | AAG | ATG | GGT | CGG | 1347 |
| Leu | Ile | Gly | Thr | Asn | Leu | Phe | Gly | Val | Leu | Ala | Asn | Lys | Met | Gly | Arg |      |
|     |     |     | 350 |     |     |     |     | 355 |     |     |     |     | 360 |     |     |      |
| TGG | CTG | TGC | TCC | CTT | GTT | GGG | ATG | GTG | GCA | GTA | GGT | ATC | AGC | TTG | CTC | 1395 |
| Trp | Leu | Cys | Ser | Leu | Val | Gly | Met | Val | Ala | Val | Gly | Ile | Ser | Leu | Leu |      |
|     |     | 365 |     |     |     |     | 370 |     |     |     |     | 375 |     |     |     |      |
| TGT | GTA | CCT | CTG | GCT | CAC | AAT | ATT | TTT | GGT | CTT | ATT | GGC | CCC | AAT | GCA | 1443 |
| Cys | Val | Pro | Leu | Ala | His | Asn | Ile | Phe | Gly | Leu | Ile | Gly | Pro | Asn | Ala |      |
|     | 380 |     |     |     |     | 385 |     |     |     |     | 390 |     |     |     |     |      |
| GGC | CTT | GGC | TTT | GCC | ATA | GGA | ATG | GTG | GAT | TCC | TCT | CTG | ATG | CCC | ATC | 1491 |
| Gly | Leu | Gly | Phe | Ala | Ile | Gly | Met | Val | Asp | Ser | Ser | Leu | Met | Pro | Ile |      |
| 395 |     |     |     |     | 400 |     |     |     | 405 |     |     |     |     |     | 410 |      |
| ATG | GGA | TAC | CTG | GTG | GAC | TTA | CGC | CAC | ACC | TCT | GTG | TAT | GGG | AGT | GTC | 1539 |
| Met | Gly | Tyr | Leu | Val | Asp | Leu | Arg | His | Thr | Ser | Val | Tyr | Gly | Ser | Val |      |
|     |     |     |     | 415 |     |     |     |     | 420 |     |     |     |     | 425 |     |      |
| TAT | GCC | ATC | GCC | GAT | GTG | GCC | TTT | TGT | GTG | GGC | TTT | GCT | ATT | GGC | CCA | 1587 |
| Tyr | Ala | Ile | Ala | Asp | Val | Ala | Phe | Cys | Val | Gly | Phe | Ala | Ile | Gly | Pro |      |
|     |     |     | 430 |     |     |     |     | 435 |     |     |     |     | 440 |     |     |      |
| TCT | ACT | GGG | GGT | GTT | ATC | GTA | CAG | GTC | ATT | GGC | TTT | CCT | TGG | CTC | ATG | 1635 |
| Ser | Thr | Gly | Gly | Val | Ile | Val | Gln | Val | Ile | Gly | Phe | Pro | Trp | Leu | Met |      |
|     |     | 445 |     |     |     |     | 450 |     |     |     |     | 455 |     |     |     |      |
| GTC | ATC | ATT | GGT | ACC | ATC | AAC | ATC | ATT | TAT | GCT | CCT | CTC | TGC | TGC | TTC | 1683 |
| Val | Ile | Ile | Gly | Thr | Ile | Asn | Ile | Ile | Tyr | Ala | Pro | Leu | Cys | Cys | Phe |      |
|     | 460 |     |     |     |     | 465 |     |     |     |     | 470 |     |     |     |     |      |
| CTG | CAG | AAC | CCG | CCA | GCT | AAG | GAG | GAG | AAG | CGT | GCA | ATT | CTG | AGC | CAG | 1731 |
| Leu | Gln | Asn | Pro | Pro | Ala | Lys | Glu | Glu | Lys | Arg | Ala | Ile | Leu | Ser | Gln |      |
| 475 |     |     |     |     | 480 |     |     |     |     | 485 |     |     |     |     | 490 |      |
| GAA | TGC | CCC | ACA | GAG | ACC | CAG | ATG | TAC | ACA | TTC | CAG | AAG | CCC | ACA | AAG | 1779 |
| Glu | Cys | Pro | Thr | Glu | Thr | Gln | Met | Tyr | Thr | Phe | Gln | Lys | Pro | Thr | Lys |      |
|     |     |     |     | 495 |     |     |     | 500 |     |     |     |     | 505 |     |     |      |
| GCG | TTT | CCA | CTA | GGA | GAG | AAC | AGC | GAT | GAT | CCT | AGC | AGC | GGG | GAG |     | 1824 |
| Ala | Phe | Pro | Leu | Gly | Glu | Asn | Ser | Asp | Asp | Pro | Ser | Ser | Gly | Glu |     |      |

-continued

```
              510                 515                 520
TAACTGCGGA  GGGCGATATC  TGAGCCTCAC  ATCTACAGGG  ACCAGTCTAC  TACAGATTCA    1884
ATAATTTTCA  CTTTCCTCTC  CTCCAGGCCA  CTGCCTTCCT  CCCTTCTTAT  TGATACCTTT    1944
CCTTTACTCA  CCTGTAAGTG  CAACCCACCA  CTCTCCCTCT  GTGCTTTGAC  ACCACCCATG    2004
GCCCACTTTT  TGTGGGAGGA  CAGTGCTATT  TCCTGCCAGG  CCAAAGCGAA  GCTGATTAAA    2064
GCTGAGTTGT  GACAAGTTCT  GCAAGGGGTG  ACTCACTTCC  TGCAGGCAGG  ACTGAACAAT    2124
GTGCCTGCGA  AATCAGGGGG  ACAAATGACA  AGCCTGCCTT  TCTTCTCTGA  TTGTTTTTTT    2184
TTTTTTTTTG  ACATATTACC  AATATGTCCT  AAAATTTGAC  TTGTGTCCTG  TGAAATGCTT    2244
TCCCCTTATT  TTTTCCAGTT  TAGCTTCTAT  ACATACGGGT  TTTTGCTTAT  TTTATGTGCT    2304
AAAATTGTTT  ACCTTCATTA  AGTGAGGCCT  TCCTACTTTC  TTCATCGCCC  AATTGAGAGG    2364
AAATAAACAA  CTTTCTTAGG  CTTGAAAAAA  AACTTTAGAG  CACAATGGAT  CTCGAGG      2421
```

( 2 ) INFORMATION FOR SEQ ID NO:2:

( i ) SEQUENCE CHARACTERISTICS:
        ( A ) LENGTH: 521 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Gln  Val  Val  Leu  Gly  Ala  Pro  Gln  Arg  Leu  Leu  Lys  Glu  Gly
 1                 5                        10                      15

Arg  Gln  Ser  Arg  Lys  Leu  Val  Leu  Val  Val  Phe  Val  Ala  Leu  Leu
                20                   25                  30

Leu  Asp  Asn  Met  Leu  Leu  Thr  Val  Val  Pro  Ile  Val  Pro  Thr  Phe
           35                   40                  45

Leu  Tyr  Ala  Thr  Glu  Phe  Lys  Asp  Ser  Asn  Ser  Ser  Leu  His  Arg  Gly
     50                        55                       60

Pro  Ser  Val  Ser  Ser  Gln  Gln  Ala  Leu  Thr  Ser  Pro  Ala  Phe  Ser  Thr
 65                      70                       75                      80

Ile  Phe  Ser  Phe  Phe  Asp  Asn  Thr  Thr  Thr  Val  Glu  Glu  His  Val
                     85                   90                  95

Pro  Phe  Arg  Val  Thr  Trp  Thr  Asn  Gly  Thr  Ile  Pro  Pro  Val  Thr
               100                  105                 110

Glu  Ala  Ser  Ser  Val  Pro  Lys  Asn  Asn  Cys  Leu  Gln  Gly  Ile  Glu  Phe
               115                  120                 125

Leu  Glu  Glu  Glu  Asn  Val  Arg  Ile  Gly  Ile  Leu  Phe  Ala  Ser  Lys  Ala
     130                       135                      140

Leu  Met  Gln  Leu  Leu  Val  Asn  Pro  Phe  Val  Gly  Pro  Leu  Thr  Asn  Arg
145                      150                      155                     160

Ile  Gly  Tyr  His  Ile  Pro  Met  Phe  Val  Gly  Phe  Met  Ile  Met  Phe  Leu
               165                  170                 175

Ser  Thr  Leu  Met  Phe  Ala  Phe  Ser  Gly  Thr  Tyr  Ala  Leu  Leu  Phe  Val
               180                  185                 190

Ala  Arg  Thr  Leu  Gln  Gly  Ile  Gly  Ser  Ser  Phe  Ser  Ser  Val  Ala  Gly
          195                  200                  205

Leu  Gly  Met  Leu  Ala  Ser  Val  Tyr  Thr  Asp  Asn  Tyr  Glu  Arg  Gly  Arg
     210                       215                      220

Ala  Met  Gly  Ile  Ala  Leu  Gly  Gly  Leu  Ala  Leu  Gly  Leu  Leu  Val  Gly
225                      230                      235                     240

Ala  Pro  Phe  Gly  Ser  Val  Met  Tyr  Glu  Phe  Val  Gly  Lys  Ser  Ser  Pro
```

|     |     |     |     |     | 245 |     |     |     | 250 |     |     |     | 255 |     |
|-----|-----|-----|-----|-----|-----|-----|-----|-----|-----|-----|-----|-----|-----|-----|
| Phe | Leu | Ile | Leu | Ala | Phe | Leu | Ala | Leu | Leu | Asp | Gly | Ala | Leu | Gln | Leu |
|     |     |     | 260 |     |     |     | 265 |     |     |     |     | 270 |     |     |
| Cys | Ile | Leu | Trp | Pro | Ser | Lys | Val | Ser | Pro | Glu | Ser | Ala | Met | Gly | Thr |
|     |     | 275 |     |     |     |     | 280 |     |     |     |     | 285 |     |     |
| Ser | Leu | Leu | Thr | Leu | Leu | Lys | Asp | Pro | Tyr | Ile | Leu | Val | Ala | Ala | Gly |
|     | 290 |     |     |     |     | 295 |     |     |     |     | 300 |     |     |     |
| Ser | Ile | Cys | Leu | Ala | Asn | Met | Gly | Val | Ala | Ile | Leu | Glu | Pro | Thr | Leu |
| 305 |     |     |     |     | 310 |     |     |     |     | 315 |     |     |     |     | 320 |
| Pro | Ile | Trp | Met | Met | Gln | Thr | Met | Cys | Ser | Pro | Glu | Trp | Gln | Leu | Gly |
|     |     |     |     | 325 |     |     |     |     | 330 |     |     |     |     | 335 |     |
| Leu | Ala | Phe | Leu | Pro | Ala | Ser | Val | Ala | Tyr | Leu | Ile | Gly | Thr | Asn | Leu |
|     |     |     | 340 |     |     |     |     | 345 |     |     |     | 350 |     |     |     |
| Phe | Gly | Val | Leu | Ala | Asn | Lys | Met | Gly | Arg | Trp | Leu | Cys | Ser | Leu | Val |
|     |     | 355 |     |     |     |     | 360 |     |     |     |     | 365 |     |     |     |
| Gly | Met | Val | Ala | Val | Gly | Ile | Ser | Leu | Leu | Cys | Val | Pro | Leu | Ala | His |
|     | 370 |     |     |     |     | 375 |     |     |     |     | 380 |     |     |     |     |
| Asn | Ile | Phe | Gly | Leu | Ile | Gly | Pro | Asn | Ala | Gly | Leu | Gly | Phe | Ala | Ile |
| 385 |     |     |     |     | 390 |     |     |     |     | 395 |     |     |     |     | 400 |
| Gly | Met | Val | Asp | Ser | Ser | Leu | Met | Pro | Ile | Met | Gly | Tyr | Leu | Val | Asp |
|     |     |     |     | 405 |     |     |     |     | 410 |     |     |     |     | 415 |     |
| Leu | Arg | His | Thr | Ser | Val | Tyr | Gly | Ser | Val | Tyr | Ala | Ile | Ala | Asp | Val |
|     |     |     | 420 |     |     |     |     | 425 |     |     |     | 430 |     |     |     |
| Ala | Phe | Cys | Val | Gly | Phe | Ala | Ile | Gly | Pro | Ser | Thr | Gly | Gly | Val | Ile |
|     |     | 435 |     |     |     |     | 440 |     |     |     |     | 445 |     |     |     |
| Val | Gln | Val | Ile | Gly | Phe | Pro | Trp | Leu | Met | Val | Ile | Ile | Gly | Thr | Ile |
|     | 450 |     |     |     |     | 455 |     |     |     |     | 460 |     |     |     |     |
| Asn | Ile | Ile | Tyr | Ala | Pro | Leu | Cys | Cys | Phe | Leu | Gln | Asn | Pro | Pro | Ala |
| 465 |     |     |     |     | 470 |     |     |     |     | 475 |     |     |     |     | 480 |
| Lys | Glu | Glu | Lys | Arg | Ala | Ile | Leu | Ser | Gln | Glu | Cys | Pro | Thr | Glu | Thr |
|     |     |     |     | 485 |     |     |     |     | 490 |     |     |     |     | 495 |     |
| Gln | Met | Tyr | Thr | Phe | Gln | Lys | Pro | Thr | Lys | Ala | Phe | Pro | Leu | Gly | Glu |
|     |     |     | 500 |     |     |     |     | 505 |     |     |     | 510 |     |     |     |
| Asn | Ser | Asp | Asp | Pro | Ser | Ser | Gly | Glu |     |     |     |     |     |     |     |
|     |     | 515 |     |     |     |     | 520 |     |     |     |     |     |     |     |     |

( 2 ) INFORMATION FOR SEQ ID NO:3:

( i ) SEQUENCE CHARACTERISTICS:
        ( A ) LENGTH: 1637 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Rattus rattus ( i x ) FEATURE:
        ( A ) NAME/KEY: CDS
        ( B ) LOCATION: 72..1619

( x i ) SEQUENCE DESCRIPTION: SEQ ID NO:3:

```
GGGCGCACGG ACAGAGACCC AGGCTGTGTG GCGCTATAAC CGCGCAGTCA CAGGCGAGCC            60

AGAGCAGAGC C ATG GCC CTG AGC GAT CTG GTG CTG CTG CGA TGG CTG CGG          110
```

```
            Met Ala Leu Ser Asp Leu Val Leu Leu Arg Trp Leu Arg
              1               5                   10

GAC AGC CGC CAC TCG CGC AAA CTG ATC CTG TTC ATC GTG TTC CTT GCG      158
Asp Ser Arg His Ser Arg Lys Leu Ile Leu Phe Ile Val Phe Leu Ala
     15              20                  25

CTG CTG CTG GAC AAC ATG CTG CTC ACC GTC GTG GTT CCC ATC ATC CCC      206
Leu Leu Leu Asp Asn Met Leu Leu Thr Val Val Val Pro Ile Ile Pro
 30              35                  40                      45

AGC TAT CTG TAC AGC ATT AAG CAT GAG AAA AAC TCT ACG GAA ATC CAG      254
Ser Tyr Leu Tyr Ser Ile Lys His Glu Lys Asn Ser Thr Glu Ile Gln
             50                  55                  60

ACC ACC AGA CCA GAG CTC GTG GTC TCC ACC TCC GAA AGC ATC TTC TCT      302
Thr Thr Arg Pro Glu Leu Val Val Ser Thr Ser Glu Ser Ile Phe Ser
         65              70                  75

TAC TAT AAC AAC TCT ACT GTG TTG ATC ACC GGG AAT GCC ACT GGG ACT      350
Tyr Tyr Asn Asn Ser Thr Val Leu Ile Thr Gly Asn Ala Thr Gly Thr
             80                  85                  90

CTT CCA GGA GGG CAG TCA CAC AAG GCT ACC AGC ACA CAG CAC ACT GTG      398
Leu Pro Gly Gly Gln Ser His Lys Ala Thr Ser Thr Gln His Thr Val
         95             100                 105

GCT AAC ACC ACT GTC CCT TCG GAC TGT CCC AGT GAA GAC AGA GAC CTT      446
Ala Asn Thr Thr Val Pro Ser Asp Cys Pro Ser Glu Asp Arg Asp Leu
110             115                 120                     125

CTG AAT GAG AAT GTG CAA GTT GGG CTG CTG TTT GCC TCC AAA GCC ACT      494
Leu Asn Glu Asn Val Gln Val Gly Leu Leu Phe Ala Ser Lys Ala Thr
                 130                 135                 140

GTC CAG CTC CTC ACT AAC CCA TTC ATA GGA CTT CTG ACC AAC AGA ATT      542
Val Gln Leu Leu Thr Asn Pro Phe Ile Gly Leu Leu Thr Asn Arg Ile
             145                 150                 155

GGC TAT CCA ATT CCC ATG TTT GCC GGC TTC TGC ATC ATG TTT ATC TCA      590
Gly Tyr Pro Ile Pro Met Phe Ala Gly Phe Cys Ile Met Phe Ile Ser
         160                 165                 170

ACA GTT ATG TTT GCC TTC TCC AGC AGC TAT GCC TTC CTG CTG ATC GCC      638
Thr Val Met Phe Ala Phe Ser Ser Ser Tyr Ala Phe Leu Leu Ile Ala
175                 180                 185

AGG TCC CTT CAG GGA ATT GGC TCC TCC TGC TCA TCC GTG GCT GGG ATG      686
Arg Ser Leu Gln Gly Ile Gly Ser Ser Cys Ser Ser Val Ala Gly Met
190                 195                 200                 205

GGT ATG CTG GCC AGC GTG TAC ACA GAT GAT GAG GAG AGG GGG AAG CCC      734
Gly Met Leu Ala Ser Val Tyr Thr Asp Asp Glu Glu Arg Gly Lys Pro
             210                 215                 220

ATG GGC ATT GCT TTG GGT GGC CTG GCC ATG GGA GTC TTA GTG GGA CCC      782
Met Gly Ile Ala Leu Gly Gly Leu Ala Met Gly Val Leu Val Gly Pro
             225                 230                 235

CCC TTC GGG AGT GTG CTC TAT GAG TTT GTG GGG AAG ACA GCT CCC TTC      830
Pro Phe Gly Ser Val Leu Tyr Glu Phe Val Gly Lys Thr Ala Pro Phe
         240                 245                 250

CTG GTG CTA GCT GCC TTG GTG CTC TTG GAT GGG GCT ATT CAG CTC TTT      878
Leu Val Leu Ala Ala Leu Val Leu Leu Asp Gly Ala Ile Gln Leu Phe
255                 260                 265

GTG CTC CAG CCG TCC CGA GTA CAG CCA GAG AGT CAG AAG GGG ACA CCT      926
Val Leu Gln Pro Ser Arg Val Gln Pro Glu Ser Gln Lys Gly Thr Pro
270                 275                 280                 285

CTA ACG ACC TTG CTG AAG GAT CCA TAC ATC CTC ATC GCT GCA GGC TCC      974
Leu Thr Thr Leu Leu Lys Asp Pro Tyr Ile Leu Ile Ala Ala Gly Ser
                 290                 295                 300

ATC TGC TTT GCA AAC ATG GGG ATA GCC ATG CTG GAG CCC GCC CTG CCC     1022
Ile Cys Phe Ala Asn Met Gly Ile Ala Met Leu Glu Pro Ala Leu Pro
             305                 310                 315
```

| | | | | | | | | | | | | | | | | |
|---|---|---|---|---|---|---|---|---|---|---|---|---|---|---|---|---|
| ATC | TGG | ATG | ATG | GAG | ACC | ATG | TGT | TCC | CGA | AAG | TGG | CAG | CTG | GGC | GTT | 1070 |
| Ile | Trp | Met 320 | Met | Glu | Thr | Met | Cys 325 | Ser | Arg | Lys | Trp | Gln 330 | Leu | Gly | Val | |
| GCT | TTC | CTC | CCG | GCG | AGC | ATC | TCT | TAT | CTC | ATT | GGA | ACC | AAT | ATT | TTT | 1118 |
| Ala | Phe 335 | Leu | Pro | Ala | Ser | Ile | Ser 340 | Tyr | Leu | Ile | Gly | Thr 345 | Asn | Ile | Phe | |
| GGG | ATA | CTT | GCA | CAC | AAA | ATG | GGA | AGG | TGG | CTA | TGT | GCT | CTT | CTG | GGA | 1166 |
| Gly 350 | Ile | Leu | Ala | His | Lys 355 | Met | Gly | Arg | Trp | Leu 360 | Cys | Ala | Leu | Leu | Gly 365 | |
| ATG | GTA | ATT | GTT | GGA | ATC | AGC | ATT | TTA | TGC | ATC | CCC | TTT | GCA | AAA | AAT | 1214 |
| Met | Val | Ile | Val | Gly 370 | Ile | Ser | Ile | Leu | Cys 375 | Ile | Pro | Phe | Ala | Lys 380 | Asn | |
| ATC | TAT | GGA | CTC | ATC | GCT | CCC | AAC | TTT | GGA | GTT | GGT | TTT | GCA | ATT | GGG | 1262 |
| Ile | Tyr | Gly | Leu 385 | Ile | Ala | Pro | Asn | Phe 390 | Gly | Val | Gly | Phe | Ala 395 | Ile | Gly | |
| ATG | GTG | GAC | TCC | TCT | ATG | ATG | CCT | ATC | ATG | GGC | TAC | CTG | GTT | GAC | CTG | 1310 |
| Met | Val | Asp 400 | Ser | Ser | Met | Met | Pro 405 | Ile | Met | Gly | Tyr | Leu 410 | Val | Asp | Leu | |
| CGG | CAT | GTG | TCT | GTC | TAT | GGG | AGT | GTT | TAT | GCC | ATT | GCA | GAC | GTG | GCC | 1358 |
| Arg | His | Val 415 | Ser | Val | Tyr | Gly | Ser 420 | Val | Tyr | Ala | Ile | Ala 425 | Asp | Val | Ala | |
| TTT | TGT | ATG | GGC | TAT | GCT | ATC | GGT | CCC | TCT | GCT | GGT | GGT | GCC | ATC | GCA | 1406 |
| Phe 430 | Cys | Met | Gly | Tyr | Ala 435 | Ile | Gly | Pro | Ser | Ala 440 | Gly | Gly | Ala | Ile | Ala 445 | |
| AAG | GCA | ATT | GGC | TTT | CCT | TGG | CTT | ATG | ACA | ATT | ATT | GGG | ATA | ATT | GAT | 1454 |
| Lys | Ala | Ile | Gly | Phe 450 | Pro | Trp | Leu | Met | Thr 455 | Ile | Ile | Gly | Ile | Ile 460 | Asp | |
| ATC | GCT | TTT | GCT | CCA | CTC | TGC | TTT | TTC | CTT | CGA | AGT | CCA | CCT | GCT | AAG | 1502 |
| Ile | Ala | Phe | Ala 465 | Pro | Leu | Cys | Phe | Phe 470 | Leu | Arg | Ser | Pro | Pro 475 | Ala | Lys | |
| GAG | GAA | AAA | ATG | GCT | ATC | CTC | ATG | GAC | CAC | AAC | TGT | CCC | ATT | AAA | AGA | 1550 |
| Glu | Glu | Lys 480 | Met | Ala | Ile | Leu | Met 485 | Asp | His | Asn | Cys | Pro 490 | Ile | Lys | Arg | |
| AAG | ATG | TAC | ACT | CAG | AAT | AAT | GTC | CAG | TCA | TAT | CCC | ATC | GGT | GAT | GAT | 1598 |
| Lys | Met | Tyr 495 | Thr | Gln | Asn | Asn | Val 500 | Gln | Ser | Tyr | Pro | Ile 505 | Gly | Asp | Asp | |
| GAA | GAA | TCT | GAA | AGT | GAC | TGAGACCCTC | TAACGTCGCC | C | | | | | | | | 1637 |
| Glu | Glu | Ser | Glu 510 | Ser | Asp 515 | | | | | | | | | | | |

( 2 ) INFORMATION FOR SEQ ID NO:4:

( i ) SEQUENCE CHARACTERISTICS:
        ( A ) LENGTH: 515 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met 1 | Ala | Leu | Ser | Asp 5 | Leu | Val | Leu | Leu | Arg 10 | Trp | Leu | Arg | Asp | Ser 15 | Arg |
| His | Ser | Arg | Lys 20 | Leu | Ile | Leu | Phe | Ile 25 | Val | Phe | Leu | Ala | Leu 30 | Leu | Leu |
| Asp | Asn | Met 35 | Leu | Leu | Thr | Val | Val 40 | Val | Pro | Ile | Ile | Pro 45 | Ser | Tyr | Leu |
| Tyr | Ser 50 | Ile | Lys | His | Glu | Lys 55 | Asn | Ser | Thr | Glu | Ile 60 | Gln | Thr | Thr | Arg |
| Pro 65 | Glu | Leu | Val | Val | Ser 70 | Thr | Ser | Glu | Ser | Ile 75 | Phe | Ser | Tyr | Tyr | Asn 80 |
| Asn | Ser | Thr | Val | Leu | Ile | Thr | Gly | Asn | Ala | Thr | Gly | Thr | Leu | Pro | Gly |

|   |   |   | 85 |   |   |   |   | 90 |   |   |   |   | 95 |   |
|---|---|---|---|---|---|---|---|---|---|---|---|---|---|---|

Gly Gln Ser His Lys Ala Thr Ser Thr Gln His Thr Val Ala Asn Thr
              100                     105                 110

Thr Val Pro Ser Asp Cys Pro Ser Glu Asp Arg Asp Leu Leu Asn Glu
            115                 120                 125

Asn Val Gln Val Gly Leu Leu Phe Ala Ser Lys Ala Thr Val Gln Leu
        130                 135                 140

Leu Thr Asn Pro Phe Ile Gly Leu Leu Thr Asn Arg Ile Gly Tyr Pro
145                     150                 155                 160

Ile Pro Met Phe Ala Gly Phe Cys Ile Met Phe Ile Ser Thr Val Met
                165                 170                 175

Phe Ala Phe Ser Ser Ser Tyr Ala Phe Leu Leu Ile Ala Arg Ser Leu
            180                 185                 190

Gln Gly Ile Gly Ser Ser Cys Ser Ser Val Ala Gly Met Gly Met Leu
        195                 200                 205

Ala Ser Val Tyr Thr Asp Asp Glu Glu Arg Gly Lys Pro Met Gly Ile
    210                 215                 220

Ala Leu Gly Gly Leu Ala Met Gly Val Leu Val Gly Pro Pro Phe Gly
225                 230                 235                 240

Ser Val Leu Tyr Glu Phe Val Gly Lys Thr Ala Pro Phe Leu Val Leu
            245                 250                 255

Ala Ala Leu Val Leu Leu Asp Gly Ala Ile Gln Leu Phe Val Leu Gln
            260                 265                 270

Pro Ser Arg Val Gln Pro Glu Ser Gln Lys Gly Thr Pro Leu Thr Thr
        275                 280                 285

Leu Leu Lys Asp Pro Tyr Ile Leu Ile Ala Ala Gly Ser Ile Cys Phe
    290                 295                 300

Ala Asn Met Gly Ile Ala Met Leu Glu Pro Ala Leu Pro Ile Trp Met
305                 310                 315                 320

Met Glu Thr Met Cys Ser Arg Lys Trp Gln Leu Gly Val Ala Phe Leu
                325                 330                 335

Pro Ala Ser Ile Ser Tyr Leu Ile Gly Thr Asn Ile Phe Gly Ile Leu
            340                 345                 350

Ala His Lys Met Gly Arg Trp Leu Cys Ala Leu Leu Gly Met Val Ile
        355                 360                 365

Val Gly Ile Ser Ile Leu Cys Ile Pro Phe Ala Lys Asn Ile Tyr Gly
    370                 375                 380

Leu Ile Ala Pro Asn Phe Gly Val Gly Phe Ala Ile Gly Met Val Asp
385                 390                 395                 400

Ser Ser Met Met Pro Ile Met Gly Tyr Leu Val Asp Leu Arg His Val
            405                 410                 415

Ser Val Tyr Gly Ser Val Tyr Ala Ile Ala Asp Val Ala Phe Cys Met
        420                 425                 430

Gly Tyr Ala Ile Gly Pro Ser Ala Gly Gly Ala Ile Ala Lys Ala Ile
    435                 440                 445

Gly Phe Pro Trp Leu Met Thr Ile Ile Gly Ile Ile Asp Ile Ala Phe
450                 455                 460

Ala Pro Leu Cys Phe Phe Leu Arg Ser Pro Pro Ala Lys Glu Glu Lys
465                 470                 475                 480

Met Ala Ile Leu Met Asp His Asn Cys Pro Ile Lys Arg Lys Met Tyr
            485                 490                 495

Thr Gln Asn Asn Val Gln Ser Tyr Pro Ile Gly Asp Asp Glu Glu Ser
        500                 505                 510

Glu Ser Asp
        515

(2) INFORMATION FOR SEQ ID NO:5:

(i) SEQUENCE CHARACTERISTICS:
        (A) LENGTH: 332 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:5:

| | | | | | |
|---|---|---|---|---|---|
| CAATGAGAAG | AATGCTACAG | AAATCCAGAC | GGCCTGGCCA | GTGCACACGG | CCTCCATCTC | 60 |
| AGACAGCTTC | CAGAGCATCT | TCTCCTATTA | TGATAACTCG | ACTATGGTCA | CCGGGAATGC | 120 |
| TACCAGAGAC | CTGACACTTC | ATCAGACCGC | CACACAGCAC | ATGGTGACCA | AGGCCTGCCG | 180 |
| TCTTCCTTCC | GACTGTCCCA | GTGAAGACAA | AGACCTCCTG | AATGAAAAGC | TGCAAGTTGG | 240 |
| TCTGTTGTTT | GCCTCGAAAG | CCACCGTCCA | GCTCATCACC | AACCCTTTCA | TAGGACTACT | 300 |
| GACCAACAGG | TAGGGCAGAC | TACTTTAGTC | AG | | | 332 |

(2) INFORMATION FOR SEQ ID NO:6:

(i) SEQUENCE CHARACTERISTICS:
        (A) LENGTH: 203 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Streptomyces plasmid (xi) SEQUENCE DESCRIPTION: SEQ ID NO:6:

Thr Ala Glu Val Pro Ala Gly Gly Arg Arg Asp Val Pro Ser Gly Val
 1               5                  10                  15

Lys Ile Thr Ala Leu Ala Thr Gly Phe Val Met Ala Thr Leu Asp Val
               20                  25                  30

Thr Val Val Asn Val Ala Gly Ala Thr Ile Gln Glu Ser Leu Asp Thr
             35                  40                  45

Thr Leu Thr Gln Leu Thr Trp Ile Val Asp Gly Tyr Val Leu Thr Phe
     50                  55                  60

Ala Ser Leu Leu Met Leu Ala Gly Gly Leu Ala Asn Arg Ile Gly Ala
 65                  70                  75                  80

Lys Thr Val Tyr Leu Trp Gly Met Gly Val Phe Phe Leu Ala Ser Leu
                 85                  90                  95

Ala Cys Ala Leu Ala Pro Thr Ala Glu Thr Leu Ile Ala Ala Arg Leu
             100                 105                 110

Val Gln Gly Ala Gly Ala Ala Leu Phe Met Pro Ser Ser Leu Ser Leu
         115                 120                 125

Leu Val Phe Ser Phe Pro Glu Lys Arg Gln Arg Thr Arg Met Leu Gly
     130                 135                 140

-continued

| Leu | Trp | Ser | Ala | Ile | Val | Ala | Thr | Ser | Ser | Gly | Leu | Gly | Pro | Thr | Val |
| --- | --- | --- | --- | --- | --- | --- | --- | --- | --- | --- | --- | --- | --- | --- | --- |
| 145 | | | | 150 | | | | | 155 | | | | | | 160 |

| Gly | Gly | Leu | Met | Val | Ser | Ala | Phe | Gly | Trp | Glu | Ser | Ile | Phe | Leu | Leu |
| --- | --- | --- | --- | --- | --- | --- | --- | --- | --- | --- | --- | --- | --- | --- | --- |
| | | | | 165 | | | | | 170 | | | | | 175 | |

| Asn | Leu | Pro | Ile | Gly | Ala | Ile | Gly | Met | Ala | Met | Thr | Tyr | Arg | Tyr | Ile |
| --- | --- | --- | --- | --- | --- | --- | --- | --- | --- | --- | --- | --- | --- | --- | --- |
| | | | 180 | | | | | 185 | | | | | 190 | | |

| Ala | Ala | Thr | Glu | Ser | Arg | Ala | Thr | Arg | Leu | Ala |
| --- | --- | --- | --- | --- | --- | --- | --- | --- | --- | --- |
| | | 195 | | | | | 200 | | | |

( 2 ) INFORMATION FOR SEQ ID NO:7:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Escherichia coli plasmid ( x i ) SEQUENCE DESCRIPTION: SEQ ID NO:7:

| Met | Lys | Ser | Asn | Asn | Ala | Leu | Ile | Val | Ile | Leu | Gly | Thr | Val | Thr | Leu |
| --- | --- | --- | --- | --- | --- | --- | --- | --- | --- | --- | --- | --- | --- | --- | --- |
| 1 | | | | 5 | | | | | 10 | | | | | 15 | |

| Asp | Ala | Val | Gly | Ile | Gly | Leu | Val | Met | Pro | Val | Leu | Pro | Gly | Leu | Leu |
| --- | --- | --- | --- | --- | --- | --- | --- | --- | --- | --- | --- | --- | --- | --- | --- |
| | | | 20 | | | | | 25 | | | | 30 | | | |

| Arg | Asp | Ile | Val | His | Ser | Asp | Ser | Ile | Ala | Ser | His | Tyr | Gly | Val | Leu |
| --- | --- | --- | --- | --- | --- | --- | --- | --- | --- | --- | --- | --- | --- | --- | --- |
| | | 35 | | | | 40 | | | | | 45 | | | | |

| Leu | Ala | Leu | Tyr | Ala | Leu | Met | Gln | Phe | Leu | Cys | Ala | Pro | Val | Leu | Gly |
| --- | --- | --- | --- | --- | --- | --- | --- | --- | --- | --- | --- | --- | --- | --- | --- |
| | 50 | | | | | 55 | | | | | 60 | | | | |

| Ala | Leu | Ser | Asp | Arg | Phe | Gly | Arg | Arg | Pro | Val | Leu | Leu | Ala | Ser | Leu |
| --- | --- | --- | --- | --- | --- | --- | --- | --- | --- | --- | --- | --- | --- | --- | --- |
| 65 | | | | | 70 | | | | 75 | | | | | | 80 |

| Leu | Gly | Ala | Thr | Ile | Asp | Tyr | Ala | Ile | Met | Ala | Thr | Thr | Pro | Val | Leu |
| --- | --- | --- | --- | --- | --- | --- | --- | --- | --- | --- | --- | --- | --- | --- | --- |
| | | | | 85 | | | | | 90 | | | | | 95 | |

| Trp | Ile | Leu | Tyr | Ala | Gly | Arg | Ile | Val | Ala | Gly | Ile | Thr | Gly | Ala | Thr |
| --- | --- | --- | --- | --- | --- | --- | --- | --- | --- | --- | --- | --- | --- | --- | --- |
| | | | 100 | | | | | 105 | | | | | 110 | | |

| Gly | Ala | Val | Ala | Gly | Ala | Tyr | Ile | Ala | Asp | Ile | Thr | Asp | Gly | Glu | Asp |
| --- | --- | --- | --- | --- | --- | --- | --- | --- | --- | --- | --- | --- | --- | --- | --- |
| | | 115 | | | | | 120 | | | | | 125 | | | |

| Arg | Ala | Arg | His | Phe | Gly | Leu | Met | Ser | Ala | Cys | Phe | Gly | Val | Gly | Met |
| --- | --- | --- | --- | --- | --- | --- | --- | --- | --- | --- | --- | --- | --- | --- | --- |
| | 130 | | | | | 135 | | | | | 140 | | | | |

| Val | Ala | Gly | Pro | Val | Ala | Gly | Gly | Leu | Leu | Gly | Ala | Ile | Ser | Leu | His |
| --- | --- | --- | --- | --- | --- | --- | --- | --- | --- | --- | --- | --- | --- | --- | --- |
| 145 | | | | | 150 | | | | | 155 | | | | | 160 |

| Ala | Pro | Phe | Leu | Ala | Ala | Ala | Val | Leu | Asn | Gly | Leu | Asn | Leu | Leu | Leu |
| --- | --- | --- | --- | --- | --- | --- | --- | --- | --- | --- | --- | --- | --- | --- | --- |
| | | | | 165 | | | | | 170 | | | | | 175 | |

| Gly | Cys | Phe | Leu | Met | Gln | Glu | Ser | His | Lys | Gly | Glu | Arg | Arg | Pro | Met |
| --- | --- | --- | --- | --- | --- | --- | --- | --- | --- | --- | --- | --- | --- | --- | --- |
| | | | 180 | | | | | 185 | | | | | 190 | | |

| Pro | Leu | Arg | Ala |
| --- | --- | --- | --- |
| | | 195 | |

( 2 ) INFORMATION FOR SEQ ID NO:8:

( i ) SEQUENCE CHARACTERISTICS:
        ( A ) LENGTH: 194 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Transposon 10

( x i ) SEQUENCE DESCRIPTION: SEQ ID NO:8:

```
Met Asn Ser Ser Thr Lys Ile Ala Leu Val Ile Thr Leu Leu Asp Ala
1               5                   10                  15

Met Gly Ile Gly Leu Ile Met Pro Val Leu Pro Thr Leu Leu Arg Glu
            20                  25                  30

Phe Ile Ala Ser Glu Asp Ile Ala Asn His Phe Gly Val Leu Leu Ala
        35                  40                  45

Leu Tyr Ala Leu Met Gln Val Ile Phe Ala Pro Trp Leu Gly Lys Met
    50                  55                  60

Ser Asp Arg Phe Gly Arg Arg Pro Val Leu Leu Ser Leu Ile Gly
65                  70                  75                  80

Ala Ser Leu Asp Tyr Leu Leu Leu Ala Phe Ser Ser Ala Leu Trp Met
                85                  90                  95

Leu Tyr Leu Gly Arg Leu Leu Ser Gly Ile Thr Gly Ala Thr Gly Ala
            100                 105                 110

Val Ala Ala Ser Val Ile Ala Asp Thr Thr Ser Ala Ser Gln Arg Val
            115                 120                 125

Lys Trp Phe Gly Trp Leu Gly Ala Ser Phe Gly Leu Gly Leu Ile Ala
        130                 135                 140

Gly Pro Ile Ile Gly Gly Phe Ala Gly Glu Ile Ser Pro His Ser Pro
145                 150                 155                 160

Phe Phe Ile Ala Ala Leu Leu Asn Ile Val Thr Phe Leu Val Val Met
                165                 170                 175

Phe Trp Phe Arg Glu Thr Lys Asn Thr Arg Asp Asn Thr Asp Thr Glu
            180                 185                 190

Val Gly
```

( 2 ) INFORMATION FOR SEQ ID NO:9:

( i ) SEQUENCE CHARACTERISTICS:
        ( A ) LENGTH: 195 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Bacillus subtilis plasmid ( x i ) SEQUENCE DESCRIPTION: SEQ ID NO:9:

```
Met Glu Lys Lys Asn Ile Thr Leu Thr Ile Leu Leu Thr Asn Leu Phe
1               5                   10                  15

Ile Ala Phe Leu Gly Ile Gly Leu Val Ile Pro Val Thr Pro Thr Ile
            20                  25                  30

Met Asn Glu Leu His Leu Ser Gly Thr Ala Val Gly Tyr Met Val Ala
        35                  40                  45

Cys Phe Ala Ile Thr Gln Leu Ile Val Ser Pro Ile Ala Gly Arg Trp
    50                  55                  60

Val Asp Arg Phe Gly Arg Lys Ile Met Ile Val Ile Gly Leu Leu Phe
```

```
              65                      70                      75                      80
Phe  Ser  Val  Ser  Glu  Phe  Leu  Phe  Gly  Ile  Gly  Lys  Thr  Val  Glu  Met
                    85                      90                      95

Leu  Phe  Ile  Thr  Arg  Met  Leu  Gly  Gly  Ile  Ser  Ala  Pro  Phe  Ile  Met
               100                     105                     110

Pro  Gly  Val  Thr  Ala  Phe  Ile  Ala  Asp  Ile  Thr  Thr  Ile  Lys  Thr  Arg
               115                     120                     125

Pro  Lys  Ala  Leu  Gly  Tyr  Met  Ser  Ala  Ala  Ile  Ser  Thr  Gly  Phe  Ile
          130                     135                     140

Ile  Gly  Pro  Gly  Ile  Gly  Gly  Phe  Leu  Ala  Glu  Val  His  Ser  Arg  Leu
145                      150                     155                          160

Pro  Phe  Phe  Phe  Ala  Ala  Ala  Phe  Ala  Leu  Leu  Ala  Ala  Ile  Leu  Ser
                    165                     170                     175

Ile  Leu  Thr  Leu  Arg  Glu  Pro  Glu  Arg  Asn  Pro  Glu  Asn  Gln  Glu  Ile
               180                     185                     190

Lys  Gly  Gln
          195
```

(2) INFORMATION FOR SEQ ID NO:10:

(i) SEQUENCE CHARACTERISTICS:
      (A) LENGTH: 220 amino acids
      (B) TYPE: amino acid
      (D) TOPOLOGY: linear (ii) MOLECULE TYPE: peptide (iii) HYPOTHETICAL: NO (v) FRAGMENT TYPE: internal (vi) ORIGINAL SOURCE:
      (A) ORGANISM: Rattus rattus (xi) SEQUENCE DESCRIPTION: SEQ ID NO:10:

```
Arg  Leu  Leu  Lys  Glu  Gly  Arg  Gln  Ser  Arg  Lys  Leu  Val  Leu  Val  Val
1                   5                       10                      15

Val  Phe  Val  Ala  Leu  Leu  Leu  Asp  Asn  Met  Leu  Leu  Thr  Val  Val
               20                      25                      30

Pro  Ile  Val  Pro  Thr  Phe  Leu  Tyr  Ala  Thr  Glu  Phe  Lys  Asp  Ser  Asn
               35                      40                      45

Ser  Ser  Leu  His  Arg  Gly  Pro  Ser  Val  Ser  Ser  Gln  Glu  Glu  Asn  Val
          50                      55                      60

Arg  Ile  Gly  Ile  Leu  Phe  Ala  Ser  Lys  Ala  Leu  Met  Gln  Leu  Leu  Val
65                      70                      75                           80

Asn  Pro  Phe  Val  Gly  Pro  Leu  Thr  Asn  Arg  Ile  Gly  Tyr  His  Ile  Pro
                    85                      90                      95

Met  Phe  Val  Gly  Phe  Met  Ile  Met  Phe  Leu  Ser  Thr  Leu  Met  Phe  Ala
               100                     105                     110

Phe  Ser  Gly  Thr  Tyr  Ala  Leu  Leu  Phe  Val  Ala  Arg  Thr  Leu  Gln  Gly
               115                     120                     125

Ile  Gly  Ser  Ser  Phe  Ser  Ser  Val  Ala  Gly  Leu  Gly  Met  Leu  Ala  Ser
          130                     135                     140

Val  Tyr  Thr  Asp  Asn  Tyr  Glu  Arg  Gly  Arg  Ala  Met  Gly  Leu  Ala  Leu
145                      150                     155                          160

Gly  Gly  Leu  Ala  Leu  Gly  Leu  Leu  Val  Gly  Ala  Pro  Phe  Gly  Ser  Val
                    165                     170                     175

Met  Tyr  Glu  Phe  Val  Gly  Lys  Ser  Ser  Pro  Phe  Leu  Ile  Leu  Ala  Phe
               180                     185                     190
```

```
           Leu  Ala  Leu  Leu  Asp  Gly  Ala  Leu  Gln  Leu  Cys  Ile  Leu  Trp  Pro  Ser
                     195                 200                           205

Lys  Val  Ser  Pro  Glu  Ser  Ala  Met  Gly  Thr  Ser  Leu
                     210                 215                 220
```

( 2 ) INFORMATION FOR SEQ ID NO:11:

( i ) SEQUENCE CHARACTERISTICS:
        ( A ) LENGTH: 220 amino acids
        ( B ) TYPE: amino acid
        ( D ) TOPOLOGY: linear ( i i ) MOLECULE TYPE: peptide ( i i i ) HYPOTHETICAL: YES ( v ) FRAGMENT TYPE: internal ( v i ) ORIGINAL SOURCE:
        ( A ) ORGANISM: Consensus sequence ( x i ) SEQUENCE DESCRIPTION: SEQ ID NO:11:

```
Xaa  Xaa  Xaa  Xaa  Xaa  Xaa  Xaa  Xaa  Xaa  Xaa  Asn  Xaa  Xaa  Leu  Xaa  Val
  1                  5                           10                      15

Xaa  Leu  Xaa  Xaa  Leu  Leu  Leu  Asp  Xaa  Met  Gly  Ile  Gly  Leu  Val  Val
          20                           25                      30

Pro  Val  Xaa  Pro  Thr  Leu  Leu  Xaa  Glu  Xaa  Xaa  Xaa  Ser  Asp  Xaa  Xaa
          35                      40                      45

Xaa  Xaa  Xaa  Xaa  Xaa  Xaa  Xaa  Xaa  Xaa  Xaa  Xaa  Xaa  Xaa  Xaa  Xaa  Xaa
          50                      55                      60

Xaa  Xaa  Gly  Val  Leu  Leu  Ala  Xaa  Tyr  Ala  Leu  Met  Gln  Leu  Xaa  Xaa
 65                      70                      75                          80

Xaa  Pro  Xaa  Xaa  Gly  Xaa  Leu  Xaa  Asp  Arg  Phe  Gly  Arg  Xaa  Xaa  Val
                    85                      90                          95

Leu  Leu  Xaa  Gly  Leu  Leu  Xaa  Xaa  Xaa  Leu  Xaa  Xaa  Leu  Leu  Phe  Ala
          100                      105                     110

Phe  Xaa  Xaa  Thr  Xaa  Xaa  Met  Leu  Xaa  Xaa  Xaa  Arg  Leu  Leu  Xaa  Gly
          115                      120                     125

Ile  Xaa  Xaa  Ala  Phe  Xaa  Xaa  Xaa  Ala  Xaa  Xaa  Xaa  Xaa  Leu  Ile  Ala
     130                      135                     140

Asp  Xaa  Thr  Asp  Xaa  Xaa  Xaa  Arg  Xaa  Arg  Xaa  Xaa  Gly  Xaa  Met  Ser
145                      150                     155                     160

Ala  Xaa  Phe  Xaa  Xaa  Gly  Leu  Ile  Xaa  Gly  Pro  Xaa  Ile  Gly  Gly  Xaa
                    165                     170                     175

Xaa  Xaa  Glu  Xaa  Xaa  Xaa  Xaa  Xaa  Pro  Phe  Xaa  Xaa  Ala  Ala  Leu
          180                      185                     190

Leu  Asn  Leu  Leu  Xaa  Xaa  Xaa  Leu  Xaa  Met  Phe  Xaa  Leu  Arg  Glu  Xaa
          195                      200                     205

Xaa  Xaa  Xaa  Xaa  Glu  Xaa  Xaa  Xaa  Xaa  Xaa  Xaa
          210                      215                     220
```

( 2 ) INFORMATION FOR SEQ ID NO:12:

( i ) SEQUENCE CHARACTERISTICS:
        ( A ) LENGTH: 1898 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO (iv) ANTI-SENSE: NO (vi) ORIGINAL SOURCE:
  (A) ORGANISM: Homo sapiens (ix) FEATURE:
  (A) NAME/KEY: CDS
  (B) LOCATION: 34..1575

(xi) SEQUENCE DESCRIPTION: SEQ ID NO:12:

```
GGCGAAGCG ACCCCGAGCG GAGCCCCGGA GCC ATG GCC CTG AGC GAG CTG GCG          54
                                    Met Ala Leu Ser Glu Leu Ala
                                     1               5

CTG GTC CGC TGG CTG CAG GAG AGC CGC CGC TCG CGG AAG CTC ATC CTG         102
Leu Val Arg Trp Leu Gln Glu Ser Arg Arg Ser Arg Lys Leu Ile Leu
         10                  15                  20

TTC ATC GTG TTC CTG GCG CTG CTG CTG GAC AAC ATG CTG CTC ACT GTC         150
Phe Ile Val Phe Leu Ala Leu Leu Leu Asp Asn Met Leu Leu Thr Val
     25                  30                  35

GTG GTC CCC ATC ATC CCA AGT TAT CTG TAC AGC ATT AAG CAT GAG AAG         198
Val Val Pro Ile Ile Pro Ser Tyr Leu Tyr Ser Ile Lys His Glu Lys
 40              45                  50                      55

AAT GCT ACA GAA ATC CAG ACG GCC AGG CCA GTG CAC ACT GCC TCC ATC         246
Asn Ala Thr Glu Ile Gln Thr Ala Arg Pro Val His Thr Ala Ser Ile
                 60                  65                  70

TCA GAC AGC TTC CAG AGC ATC TTC TCC TAT TAT GAT AAC TCG ACT ATG         294
Ser Asp Ser Phe Gln Ser Ile Phe Ser Tyr Tyr Asp Asn Ser Thr Met
             75                  80                  85

GTC ACC GGG AAT GCT ACC AGA GAC CTG ACA CTT CAT CAG ACC GCC ACA         342
Val Thr Gly Asn Ala Thr Arg Asp Leu Thr Leu His Gln Thr Ala Thr
         90                  95                 100

CAG CAC ATG GTG ACC AAC GCG TCC GCT GTT CCT TCC GAC TGT CCC AGT         390
Gln His Met Val Thr Asn Ala Ser Ala Val Pro Ser Asp Cys Pro Ser
    105                 110                 115

GAA GAC AAA GAC CTC CTG AAT GAA AAC GTG CAA GTT GGT CTG TTG TTT         438
Glu Asp Lys Asp Leu Leu Asn Glu Asn Val Gln Val Gly Leu Leu Phe
120                 125                 130                 135

GCC TCG AAA GCC ACC GTC CAG CTC ATC ACC AAC CCT TTC ATA GGA CTA         486
Ala Ser Lys Ala Thr Val Gln Leu Ile Thr Asn Pro Phe Ile Gly Leu
                140                 145                 150

CTG ACC AAC AGA ATT GGC TAT CCA ATT CCC ATA TTT GCG GGA TTC TGC         534
Leu Thr Asn Arg Ile Gly Tyr Pro Ile Pro Ile Phe Ala Gly Phe Cys
            155                 160                 165

ATC ATG TTT GTC TCA ACA ATT ATG TTT GCC TTC TCC AGC AGC TAT GCC         582
Ile Met Phe Val Ser Thr Ile Met Phe Ala Phe Ser Ser Ser Tyr Ala
        170                 175                 180

TTC CTG CTG ATT GCC AGG TCG CTG CAG GGC ATC GGC TCG TCC TGC TCC         630
Phe Leu Leu Ile Ala Arg Ser Leu Gln Gly Ile Gly Ser Ser Cys Ser
185                 190                 195

TCT GTG GCT GGG ATG GGC ATG CTT GCC AGT GTC TAC ACA GAT GAT GAA         678
Ser Val Ala Gly Met Gly Met Leu Ala Ser Val Tyr Thr Asp Asp Glu
200                 205                 210                 215

GAG AGA GGC AAC GTC ATG GGA ATC GCC TTG GGA GGC CTG GCC ATG GGG         726
Glu Arg Gly Asn Val Met Gly Ile Ala Leu Gly Gly Leu Ala Met Gly
            220                 225                 230

GTC TTA GTG GGC CCC CCC TTC GGG AGT GTG CTC TAT GAG TTT GTG GGG         774
Val Leu Val Gly Pro Pro Phe Gly Ser Val Leu Tyr Glu Phe Val Gly
        235                 240                 245

AAG ACG GCT CCG TTC CTG GTG CTG GCC GCC CTG GTA CTC TTG GAT GGA         822
Lys Thr Ala Pro Phe Leu Val Leu Ala Ala Leu Val Leu Leu Asp Gly
    250                 255                 260
```

```
GCT ATT CAG CTC TTT GTG CTC CAG CCG TCC CGG GTG CAG CCA GAG AGT    870
Ala Ile Gln Leu Phe Val Leu Gln Pro Ser Arg Val Gln Pro Glu Ser
    265                 270                 275

CAG AAG GGG ACA CCC CTA ACC ACG CTG CTG AAG GAC CCG TAC ATC CTC    918
Gln Lys Gly Thr Pro Leu Thr Thr Leu Leu Lys Asp Pro Tyr Ile Leu
280                 285                 290                 295

ATT GCT GCA GGC TCC ATC TGC TTT GCA AAC ATG GGC ATC GCC ATG CTG    966
Ile Ala Ala Gly Ser Ile Cys Phe Ala Asn Met Gly Ile Ala Met Leu
                    300                 305                 310

GAG CCA GCC CTG CCC ATC TGG ATG ATG GAG ACC ATG TGT TCC CGA AAG   1014
Glu Pro Ala Leu Pro Ile Trp Met Met Glu Thr Met Cys Ser Arg Lys
                315                 320                 325

TGG CAG CTG GGC GTT GCC TTC TTG CCA GCT AGT ATC TCT TAT CTC ATT   1062
Trp Gln Leu Gly Val Ala Phe Leu Pro Ala Ser Ile Ser Tyr Leu Ile
            330                 335                 340

GGA ACC AAT ATT TTT GGG ATA CTT GCA CAC AAA ATG GGG AGG TGG CTT   1110
Gly Thr Asn Ile Phe Gly Ile Leu Ala His Lys Met Gly Arg Trp Leu
        345                 350                 355

TGT GCT CTT CTG GGA ATG ATA ATT GTT GGA GTC AGC ATT TTA TGT ATT   1158
Cys Ala Leu Leu Gly Met Ile Ile Val Gly Val Ser Ile Leu Cys Ile
360                 365                 370                 375

CCA TTT GCA AAA AAC ATT TAT GGA CTC ATA GCT CCG AAC TTT GGA GTT   1206
Pro Phe Ala Lys Asn Ile Tyr Gly Leu Ile Ala Pro Asn Phe Gly Val
                    380                 385                 390

GGT TTT GCA ATT GGA ATG GTG GAT TCG TCA ATG ATG CCT ATC ATG GGC   1254
Gly Phe Ala Ile Gly Met Val Asp Ser Ser Met Met Pro Ile Met Gly
                395                 400                 405

TAC CTC GTA GAC CTG CGG CAC GTG TCC GTC TAT GGG AGT GTG TAC GCC   1302
Tyr Leu Val Asp Leu Arg His Val Ser Val Tyr Gly Ser Val Tyr Ala
            410                 415                 420

ATT GCG GAT GTG GCA TTT TGT ATG GGG TAT GCT ATA GGT CCT TCT GCT   1350
Ile Ala Asp Val Ala Phe Cys Met Gly Tyr Ala Ile Gly Pro Ser Ala
        425                 430                 435

GGT GGT GCT ATT GCA AAG GCA ATT GGA TTT CCA TGG CTC ATG ACA ATT   1398
Gly Gly Ala Ile Ala Lys Ala Ile Gly Phe Pro Trp Leu Met Thr Ile
440                 445                 450                 455

ATT GGG ATA ATT GAT ATT CTT TTT GCC CCT CTC TGC TTT TTT CTT CGA   1446
Ile Gly Ile Ile Asp Ile Leu Phe Ala Pro Leu Cys Phe Phe Leu Arg
                    460                 465                 470

AGT CCA CCT GCC AAA GAA GAA AAA ATG GCT ATT CTC ATG GAT CAC AAC   1494
Ser Pro Pro Ala Lys Glu Glu Lys Met Ala Ile Leu Met Asp His Asn
                475                 480                 485

TGC CCT ATT AAA ACA AAA ATG TAC ACT CAG AAT AAT ATC CAG TCA TAT   1542
Cys Pro Ile Lys Thr Lys Met Tyr Thr Gln Asn Asn Ile Gln Ser Tyr
            490                 495                 500

CCG ATA GGT GAA GAT GAA GAA TCT GAA AGT GAC TGAGATGAGA TCCTCAAAAA  1595
Pro Ile Gly Glu Asp Glu Glu Ser Glu Ser Asp
        505                 510

TCATCAAAGT GTTTAATTGT ATAAAACAGT GTTTCCAGTG ACACAACTCA TCCAGAACTG  1655

TCTTAGTCAT ACCATCCATC CCTGGTGAAA GAGTAAAACC AAAGGTTATT ATTTCCTTTC  1715

CATGGTTATG GTCGATTGCC AACAGCCTTA TAAAGAAAAA GAAGCTTTTC TAGGGGTTTG  1775

TATAAATAGT GTTGAAACTT TATTTTATGT ATTTAATTTT ATTAAATATC ATACAATATA  1835

TTTTGATGAA ATAGGTATTG TGTAAATCTA TAAATATTTG AATCCAAACC AAATATAATT  1895

TCC                                                                1898
```

( 2 ) INFORMATION FOR SEQ ID NO:13:

( i ) SEQUENCE CHARACTERISTICS:

( A ) LENGTH: 514 amino acids
( B ) TYPE: amino acid
( D ) TOPOLOGY: linear ( i i ) MOLECULE TYPE: protein ( x i ) SEQUENCE DESCRIPTION: SEQ ID NO:13:

| Met | Ala | Leu | Ser | Glu | Leu | Ala | Leu | Val | Arg | Trp | Leu | Gln | Glu | Ser | Arg |
|---|---|---|---|---|---|---|---|---|---|---|---|---|---|---|---|
| 1 | | | | 5 | | | | | 10 | | | | | 15 | |

| Arg | Ser | Arg | Lys | Leu | Ile | Leu | Phe | Ile | Val | Phe | Leu | Ala | Leu | Leu | Leu |
| | | | 20 | | | | 25 | | | | | 30 | | | |

| Asp | Asn | Met | Leu | Leu | Thr | Val | Val | Pro | Ile | Ile | Pro | Ser | Tyr | Leu |
| | | 35 | | | | 40 | | | | | 45 | | | |

Tyr Ser Ile Lys His Glu Lys Asn Ala Thr Glu Ile Gln Thr Ala Arg
    50              55                  60

Pro Val His Thr Ala Ser Ile Ser Asp Ser Phe Gln Ser Ile Phe Ser
65              70                  75                          80

Tyr Tyr Asp Asn Ser Thr Met Val Thr Gly Asn Ala Thr Arg Asp Leu
                85                  90                  95

Thr Leu His Gln Thr Ala Thr Gln His Met Val Thr Asn Ala Ser Ala
            100                 105                 110

Val Pro Ser Asp Cys Pro Ser Glu Asp Lys Asp Leu Leu Asn Glu Asn
        115                 120                 125

Val Gln Val Gly Leu Leu Phe Ala Ser Lys Ala Thr Val Gln Leu Ile
    130                 135                 140

Thr Asn Pro Phe Ile Gly Leu Leu Thr Asn Arg Ile Gly Tyr Pro Ile
145                 150                 155                 160

Pro Ile Phe Ala Gly Phe Cys Ile Met Phe Val Ser Thr Ile Met Phe
                165                 170                 175

Ala Phe Ser Ser Ser Tyr Ala Phe Leu Leu Ile Ala Arg Ser Leu Gln
            180                 185                 190

Gly Ile Gly Ser Ser Cys Ser Ser Val Ala Gly Met Gly Met Leu Ala
        195                 200                 205

Ser Val Tyr Thr Asp Asp Glu Glu Arg Gly Asn Val Met Gly Ile Ala
    210                 215                 220

Leu Gly Gly Leu Ala Met Gly Val Leu Val Gly Pro Pro Phe Gly Ser
225                 230                 235                 240

Val Leu Tyr Glu Phe Val Gly Lys Thr Ala Pro Phe Leu Val Leu Ala
                245                 250                 255

Ala Leu Val Leu Leu Asp Gly Ala Ile Gln Leu Phe Val Leu Gln Pro
            260                 265                 270

Ser Arg Val Gln Pro Glu Ser Gln Lys Gly Thr Pro Leu Thr Thr Leu
        275                 280                 285

Leu Lys Asp Pro Tyr Ile Leu Ile Ala Ala Gly Ser Ile Cys Phe Ala
    290                 295                 300

Asn Met Gly Ile Ala Met Leu Glu Pro Ala Leu Pro Ile Trp Met Met
305                 310                 315                 320

Glu Thr Met Cys Ser Arg Lys Trp Gln Leu Gly Val Ala Phe Leu Pro
                325                 330                 335

Ala Ser Ile Ser Tyr Leu Ile Gly Thr Asn Ile Phe Gly Ile Leu Ala
            340                 345                 350

His Lys Met Gly Arg Trp Leu Cys Ala Leu Leu Gly Met Ile Ile Val
        355                 360                 365

Gly Val Ser Ile Leu Cys Ile Pro Phe Ala Lys Asn Ile Tyr Gly Leu
    370                 375                 380

| | | | | | | | | | | | | | | | |
|---|---|---|---|---|---|---|---|---|---|---|---|---|---|---|---|
| Ile | Ala | Pro | Asn | Phe | Gly | Val | Gly | Phe | Ala | Ile | Gly | Met | Val | Asp | Ser |
| 385 | | | | 390 | | | | | 395 | | | | | | 400 |
| Ser | Met | Met | Pro | Ile | Met | Gly | Tyr | Leu | Val | Asp | Leu | Arg | His | Val | Ser |
| | | | | 405 | | | | | 410 | | | | | 415 | |
| Val | Tyr | Gly | Ser | Val | Tyr | Ala | Ile | Ala | Asp | Val | Ala | Phe | Cys | Met | Gly |
| | | | 420 | | | | | 425 | | | | | 430 | | |
| Tyr | Ala | Ile | Gly | Pro | Ser | Ala | Gly | Gly | Ala | Ile | Ala | Lys | Ala | Ile | Gly |
| | | | 435 | | | | | 440 | | | | | 445 | | |
| Phe | Pro | Trp | Leu | Met | Thr | Ile | Ile | Gly | Ile | Ile | Asp | Ile | Leu | Phe | Ala |
| | 450 | | | | | 455 | | | | | 460 | | | | |
| Pro | Leu | Cys | Phe | Phe | Leu | Arg | Ser | Pro | Pro | Ala | Lys | Glu | Glu | Lys | Met |
| 465 | | | | | 470 | | | | | 475 | | | | | 480 |
| Ala | Ile | Leu | Met | Asp | His | Asn | Cys | Pro | Ile | Lys | Thr | Lys | Met | Tyr | Thr |
| | | | | 485 | | | | | 490 | | | | | 495 | |
| Gln | Asn | Asn | Ile | Gln | Ser | Tyr | Pro | Ile | Gly | Glu | Asp | Glu | Glu | Ser | Glu |
| | | | 500 | | | | | 505 | | | | | 510 | | |
| Ser | Asp | | | | | | | | | | | | | | |

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic primer (xi) SEQUENCE DESCRIPTION: SEQ ID NO:14:

CTGACTAAAG TAGTCTGCC                19

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic primer (xi) SEQUENCE DESCRIPTION: SEQ ID NO:15:

TACAGAAATC CAGACGG                17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Synthetic primer (xi) SEQUENCE DESCRIPTION: SEQ ID NO:16:

CGTCTGGATT TCTGTAG     17

(2) INFORMATION FOR SEQ ID NO:17:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Synthetic primer (xi) SEQUENCE DESCRIPTION: SEQ ID NO:17:

GGCATGGTGC TTTCTAG     17

I claim:
1. An isolated DNA molecule encoding the amino acid sequence shown in FIG. 1 (SEQ ID NO: 2).

* * * * *

UNITED STATES PATENT AND TRADEMARK OFFICE
CERTIFICATE OF CORRECTION

PATENT NO. : 5,688,936

DATED : November 18, 1997

INVENTOR(S) : Edwards

It is certified that error appears in the above-identified patent and that said Letters Patent is hereby corrected as shown below:

Column 8, line 60 "10g25" should read --10q25--

Column 24, line 8 "FV" should read --Fv--

Column 28, line 42 "3500xfor" should read --3500 x g for--

Column 33, line 21 "18 hours Fig." should read --18 hours. Fig.--

Column 41, line 58 "0.5M M" should read --0.5M--

Column 41, line 63 "2xstandard" should read --2 X standard--

Column 1, line 18 "BNS 90-11993" should read --BNS 90-11883--

Signed and Sealed this

Fifteenth Day of June, 1999

Attest:

Attesting Officer

Q. TODD DICKINSON

Acting Commissioner of Patents and Trademarks